US011097034B2

(12) United States Patent
Alsberg et al.

(10) Patent No.: US 11,097,034 B2
(45) Date of Patent: Aug. 24, 2021

(54) COMPOSITIONS AND METHODS OF MODULATING ENDOCHONDRAL OSSIFICATION AND BONE FORMATION

(71) Applicants: CASE WESTERN RESERVE UNIVERISTY, Cleveland, OH (US); UNIVERSITY OF CALIFORNIA, SAN FRANCISCO, San Francisco, CA (US)

(72) Inventors: Eben Alsberg, Cleveland, OH (US); Oju Jeon, Cleveland, OH (US); Ralph Marcucio, San Francisco, CA (US); Chelsea Bahney, San Francisco, CA (US); Diane Hu, San Francisco, CA (US); Sarah Knox, San Francisco, CA (US)

(73) Assignees: CASE WESTERN RESERVE UNIVERSITY, Cleveland, OH (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 16/468,547

(22) PCT Filed: Dec. 11, 2017

(86) PCT No.: PCT/US2017/065588
§ 371 (c)(1),
(2) Date: Jun. 11, 2019

(87) PCT Pub. No.: WO2018/107157
PCT Pub. Date: Jun. 14, 2018

(65) Prior Publication Data
US 2019/0358364 A1 Nov. 28, 2019

Related U.S. Application Data

(60) Provisional application No. 62/432,580, filed on Dec. 11, 2016.

(51) Int. Cl.
| | |
|---|---|
| *A61K 31/221* | (2006.01) |
| *A61K 31/5578* | (2006.01) |
| *A61L 27/38* | (2006.01) |
| *A61K 35/28* | (2015.01) |
| *A61K 38/20* | (2006.01) |
| *A61K 35/32* | (2015.01) |
| *A61K 45/06* | (2006.01) |

(52) U.S. Cl.
CPC ........ *A61L 27/3847* (2013.01); *A61K 31/221* (2013.01); *A61K 31/5578* (2013.01); *A61K 35/28* (2013.01); *A61K 35/32* (2013.01); *A61K 38/204* (2013.01); *A61K 38/2093* (2013.01); *A61L 27/3817* (2013.01); *A61L 27/3852* (2013.01); *A61K 45/06* (2013.01); *A61L 2300/426* (2013.01); *A61L 2300/432* (2013.01); *A61L 2430/02* (2013.01); *A61L 2430/06* (2013.01)

(58) Field of Classification Search
CPC .. A61K 31/221; A61K 31/5578; A61K 35/28; A61K 35/32; A61K 38/20; A61L 27/38
See application file for complete search history.

(56) References Cited

U.S. PATENT DOCUMENTS

| | | | |
|---|---|---|---|
| 2005/0171015 A1* | 8/2005 | Crabtree | .............. A61K 38/465 514/9.4 |
| 2012/0301442 A1 | 11/2012 | Cool et al. | |

FOREIGN PATENT DOCUMENTS

| | | |
|---|---|---|
| WO | 90/10454 A1 | 9/1990 |
| WO | 2011/119507 A1 | 9/2011 |

OTHER PUBLICATIONS

Supplementary Partial European Search Report for Application No. 17879074, dated Dec. 12, 2019.
Chelsea S. Bahney, et al., "The Multifaceted Role of the Vasculature in Endochondral Fracture Repair", Fontiers in Endocrinology, vol. 6, Feb. 5, 2015 (Feb. 5, 2015), p. 4.
Chelsea S. Bahney, et al., "Stem Cell-Derived Endochondral Cartilage Stimulates Bone Healing by Tissue Transformation", Journal of Bone and Mineral Research, vol. 29, No. 5, Apr. 22, 2014, pp. 1269-1282.
Xin Zhou, et al., "Chondrocytes Transdifferentiate into Osteoblasts in Endochondral Bone during Development, Postnatal Growth and Fracture Healing in Mice", PLOS GENETICS, vol. 10, No. 12, Dec. 4, 2014.
L. Yang, et al., "Hypertrophic chondrocytes can become osteoblasts and osteocytes in endochondral bone formation", Proceedings of the National Academy of Sciences, vol. 111, No. 33, Aug. 19, 2014, pp. 12097-12102.
Dazai S, et al., "Leukemia inhibitory factor enhances bone formation in calvarial bone defect", The Journal of Craniofacial Surgery, Nov. 2000, vol. 11, No. 6, Nov. 2000, pp. 513-520.
Rozen, et al., "Fracture repair: Modulation of fracture-callus and mechanical properties by sequential application of IL-6 following PTH 1-34 or PTH 28-48", IL-6 following PTH 1-34 or PTH 28-48, BONE, Pergamon Press., Oxford, GB, vol. 41, No. 3, Aug. 8, 2007, pp. 437-445.
Rachelle W. Johnson, et al., "Glycoprotein130 (Gp130)/interleukin-6 (IL-6) signalling in osteoclasts promotes bone formation in periosteal and trabecular bone", BONE, vol. 81, Aug. 7, 2015, pp. 343-351.
Guihard P, et al., "Induction of osteogenesis in mesenchymal stem cells by activated monocytes/macrophages depends on Oncostatin M signaling", vol. 50, May 2012.

(Continued)

*Primary Examiner* — Zohreh A Fay
(74) *Attorney, Agent, or Firm* — Tarolli, Sundheim, Covell & Tummino LLP

(57) ABSTRACT

A method of modulating transdifferentiation of chondrocytes to osteoblast includes administering to the chondrocytes an agent that modulates GP130 receptor signaling and expression of at least one of Sox2, Oct4, or Nanog of the chondrocytes.

15 Claims, 27 Drawing Sheets

(56) References Cited

OTHER PUBLICATIONS

Italian Patent Office, Document No. 102011902009885A1, (BIONEST Ltd), Jul. 1, 2013 (Jul. 1, 2013).
Provisional Opinion for Application No. 17879074.7.
Applicant: Case Western Reserve University, et al; European Patent Application No. 17879074.7, Filing Date: Dec. 11, 2017; Communication pursuant to Article 94(3) EPC; dated Jul. 20, 2020; 10 pgs.
Eben Alsberg; U.S. Appl. No. 16/107,756, filed Aug. 21, 2018; NonFinal Office Action; dated Aug. 26, 2020; 16 pgs.
First Named Inventor: Eben Alsberg; U.S. Appl. No. 16/107,774, filed Aug. 21, 2018; NonFinal Office Action; dated Sep. 17, 2020; 16 pgs.
First Named Inventor: Eben Alsberg; U.S. Appl. No. 16/726,375, filed Dec. 24, 2019; NonFinal Office Action; dated Oct. 5, 2020.
Nakajima et al. "Interleukin-6 inhibits early differentiation of ATDC5 chondrogenic progenitor cells," Cytokine, Jun. 16, 2009, vol. 47, No. 2. pp. 91-97.
Huang et al. "Concurrent expression of Oct4 and Nanog maintains mesenchymal stem-like property of human dental pulp cells," Int J Mol Sci, Oct. 15, 2014 {Oct. 15, 2014}, vol. 15, No. 10, pp. 18623-18639.
Ling et al. "Distinct requirements of wls, wnt9a, wnt5b and gpc4 in regulating chondrocyte maturation and timing of endochondral ossification," Dev Biol, Nov. 29, 2016 (Nov. 29, 2016), vol. 421, No. 2, pp. 219-232.
Sato et al. "Functional role of acetylcholine and the expression of cholinergic receptors and components in osteoblasts," FEBS Lett, Jan. 12, 2010 (Jan. 12, 2010). vol. 584, No. 4, pp. 817-824.
Hu et al. "Cartilage to bone transformation during fracture healing is coordinated by the invading vasculature and induction of the core pluripotency genes," Development. Jan. 15, 2017 (Jan. 15, 2017), vol. 144, No. 2, pp. 221-234.
Zhou et al. Chondrocytes transdifferentiate into osteoblasts in endochondral bone during development, postnatal growth and fracture healing in mice; PLoS Genetics, Dec. 4, 2014 (Dec. 4, 2014), vol. 10, pp. 1-20.
Zou et al. "Effects of oncostatin M on cell proliferation and osteogenic differentiation in C3H10T1/2," J Musculoskelet Neuronal Interact, Dec. 14, 2016 (Dec. 14, 2016), vol. 16, No. 4, pp. 377-385.
Chelsea S. Bahney, et al., "The Multifaceted Role of the Vasculature in Endochondral Fracture Repair", Frontiers in Endocrinology, vol. 6, Feb. 5, 2015 (Feb. 5, 2015), p. 4.

* cited by examiner

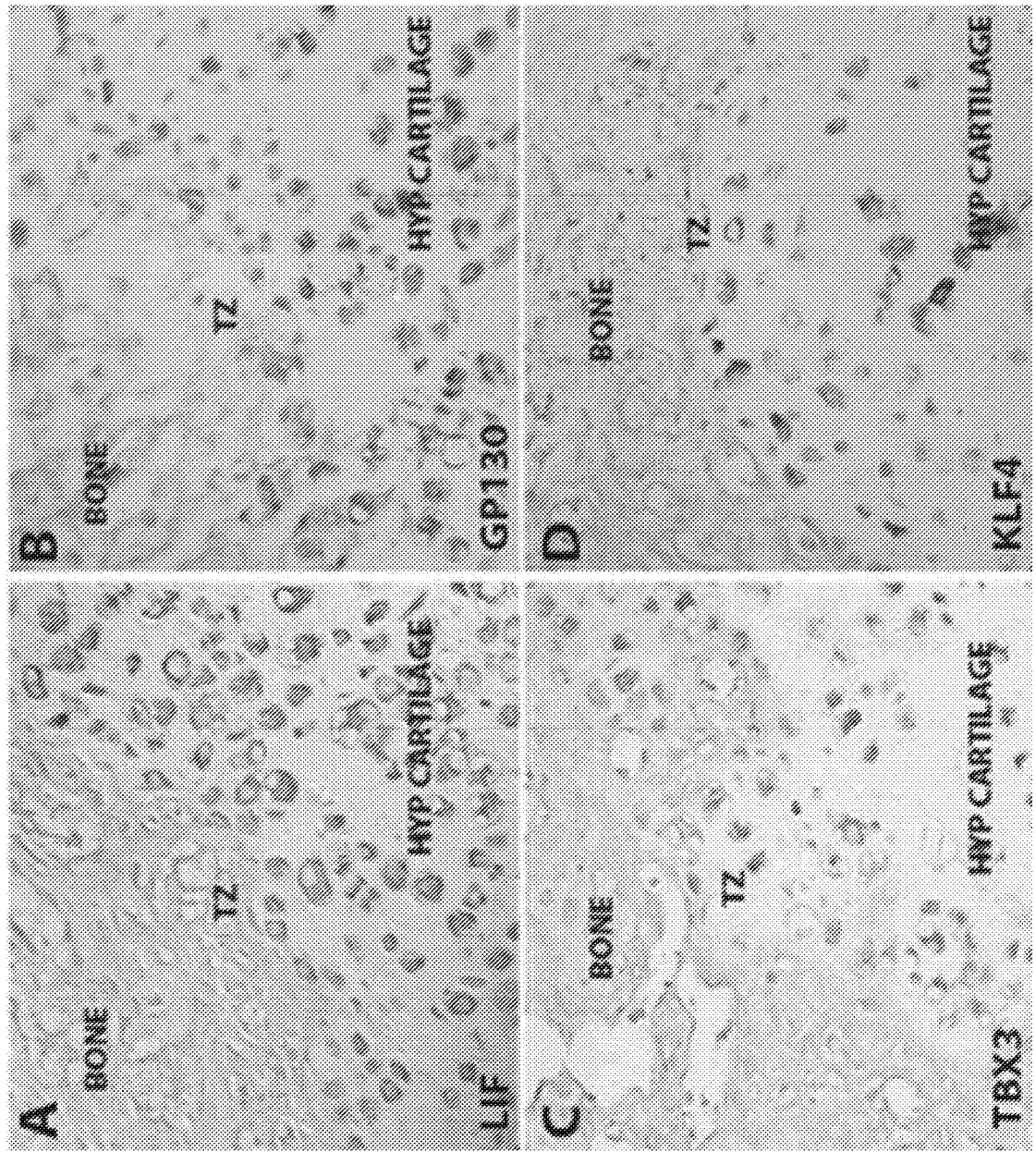
Figs. 13A-D

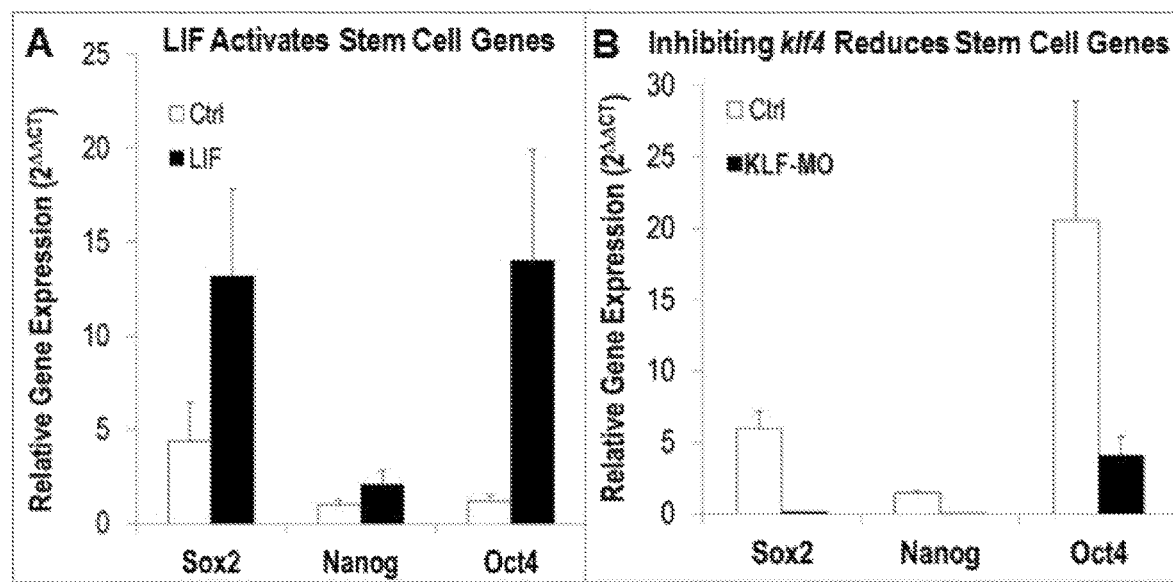
Figs. 14A-B
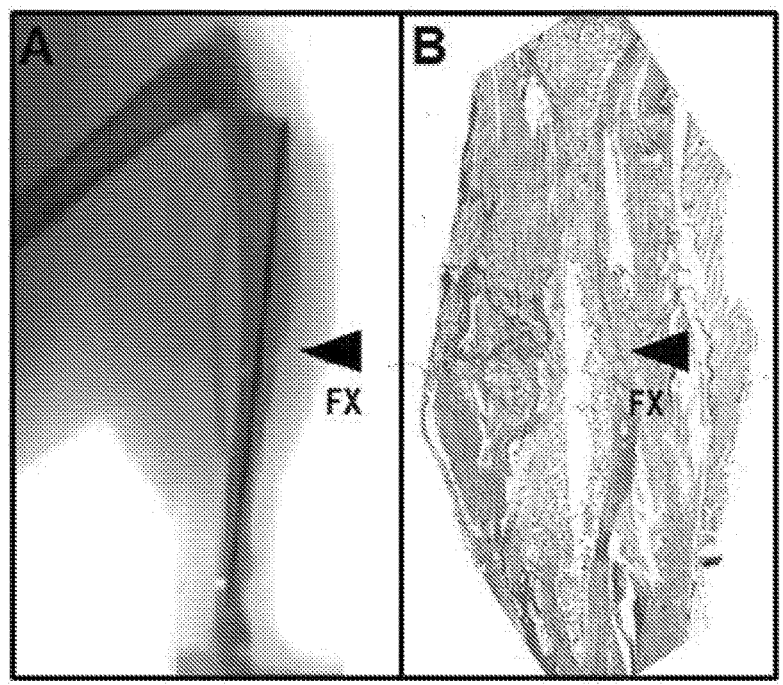
Figs. 15A-B

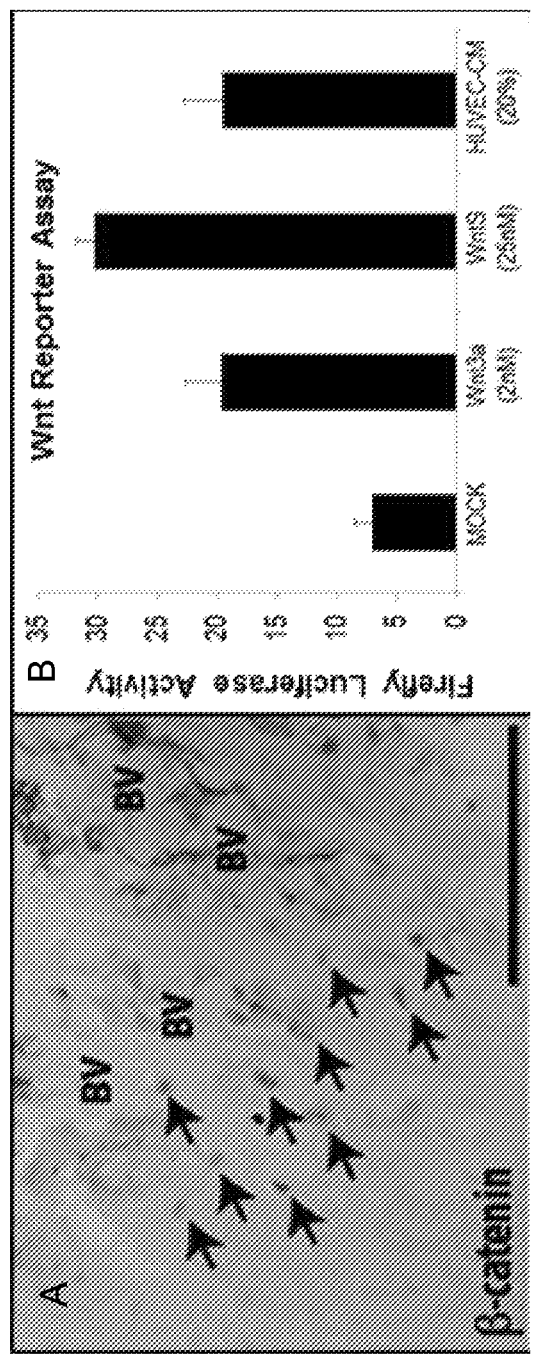
Figs. 16A-B

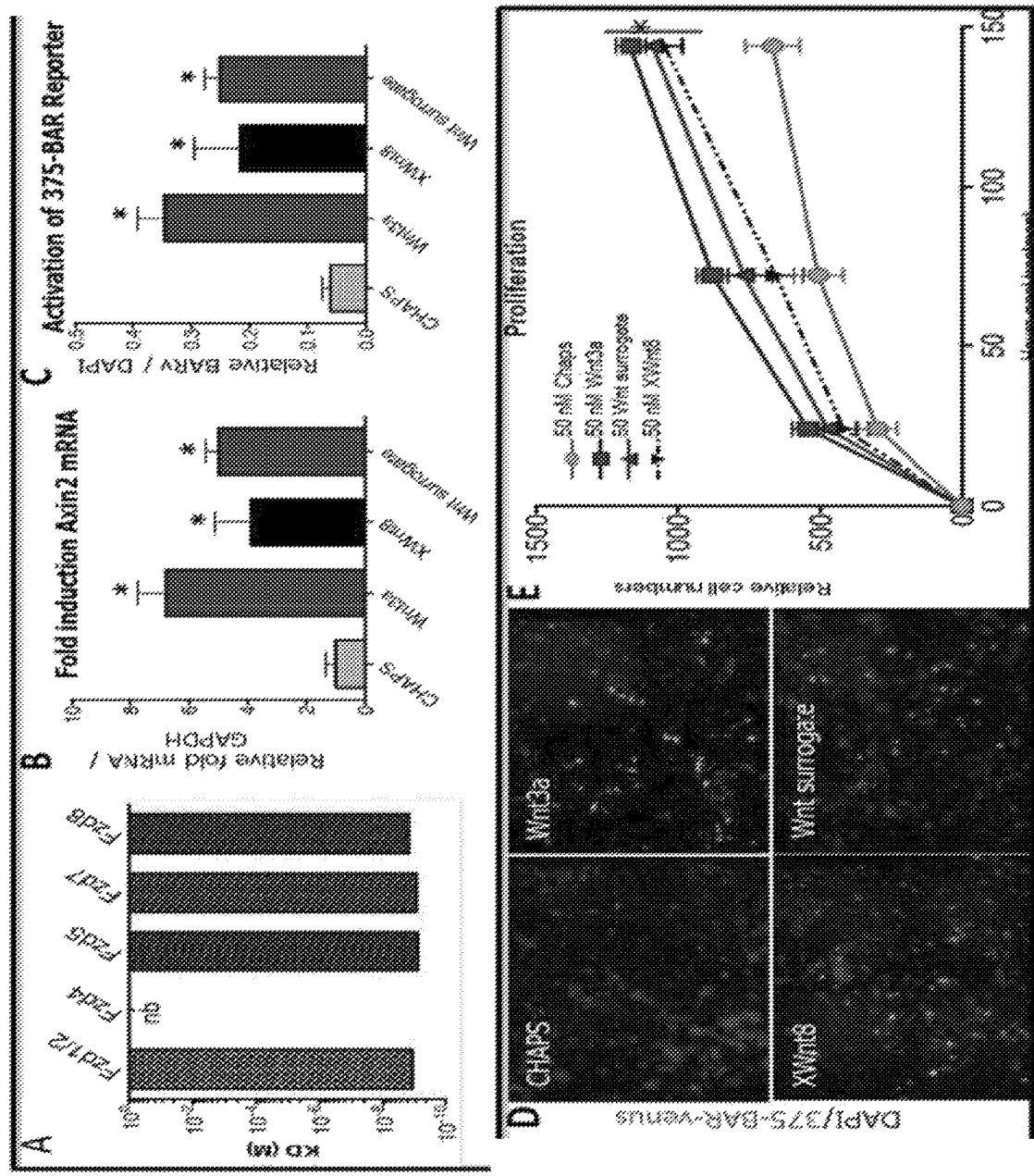
Figs. 17A-E

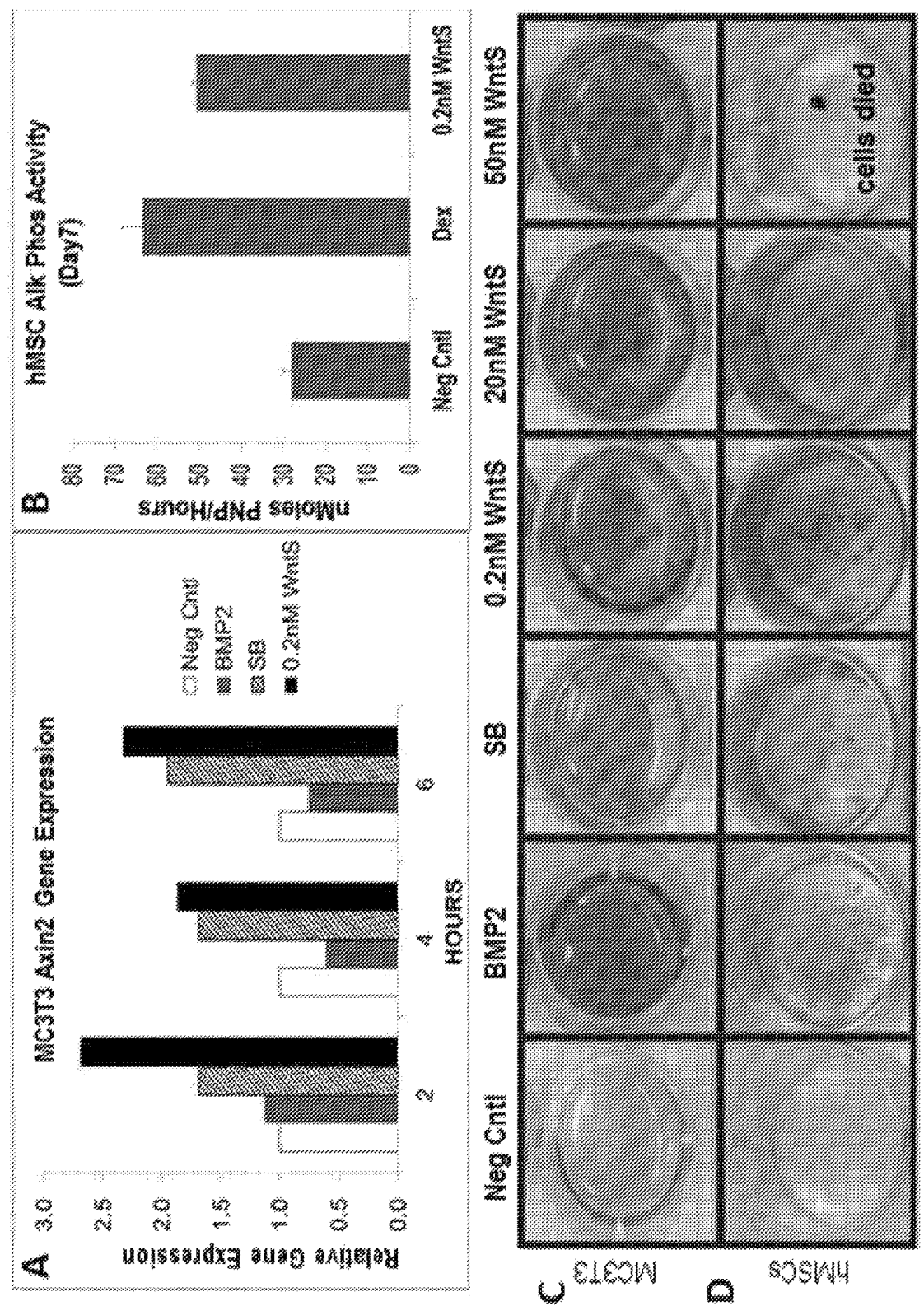
Figs. 18A-D

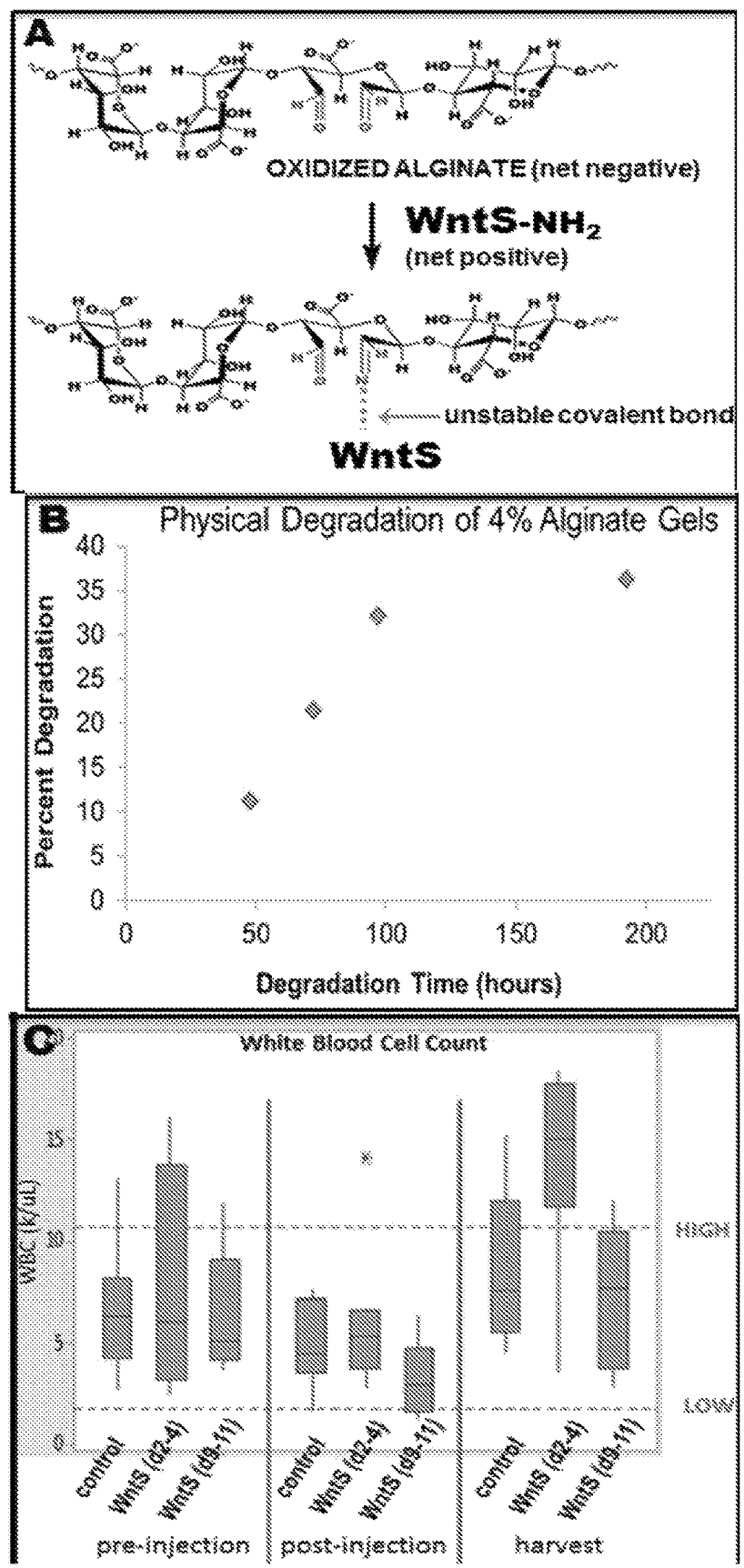
Figs. 20A-C

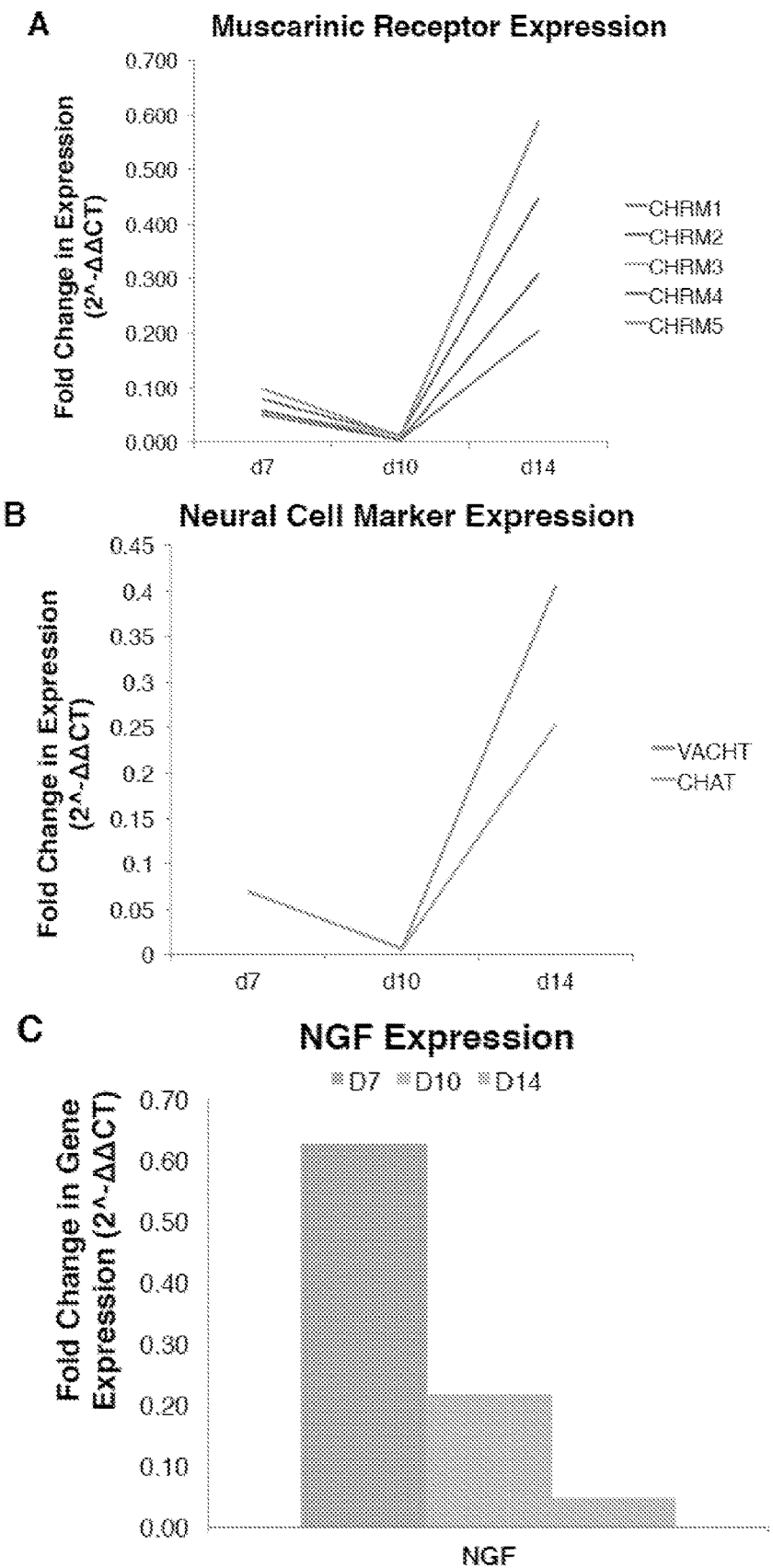
Figs. 21A-C

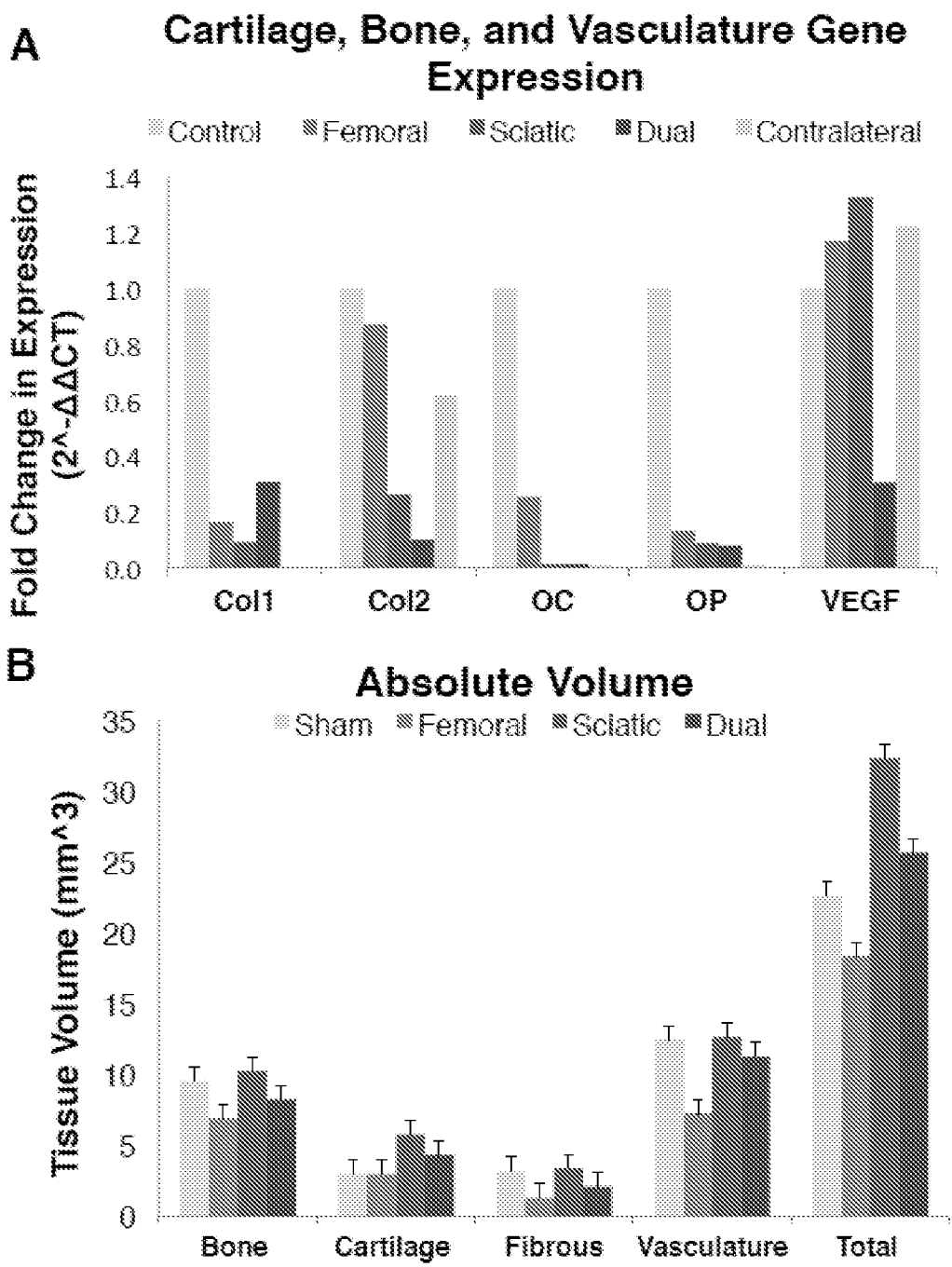
Figs. 22A-B

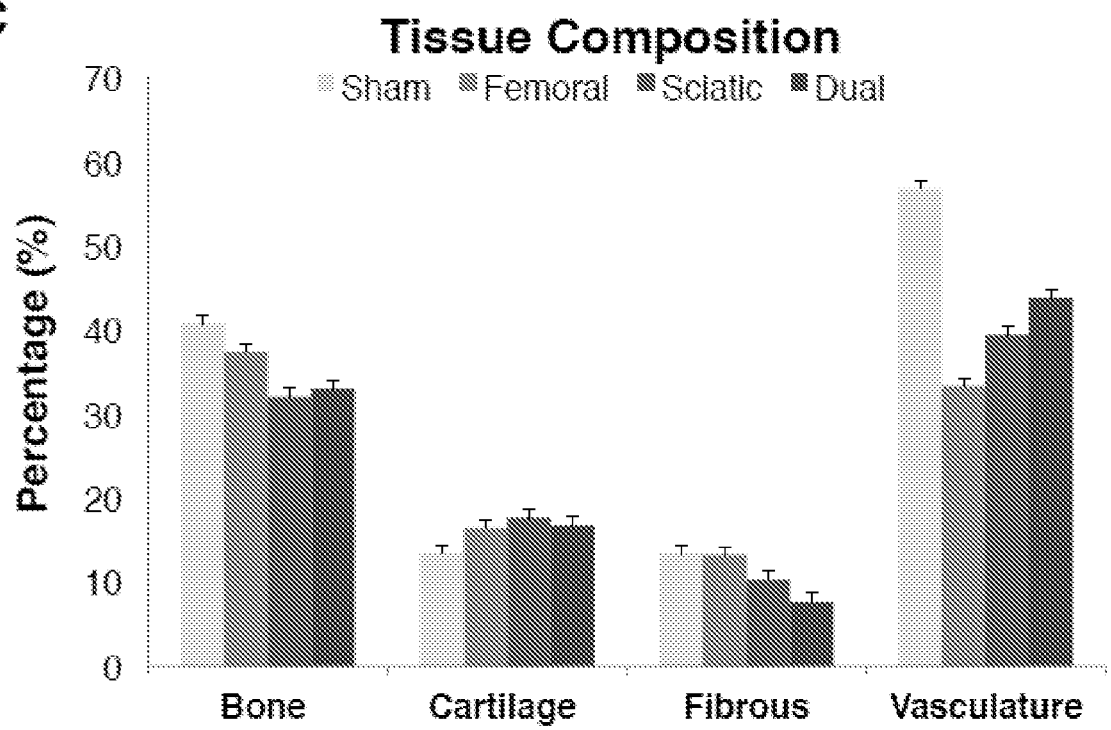
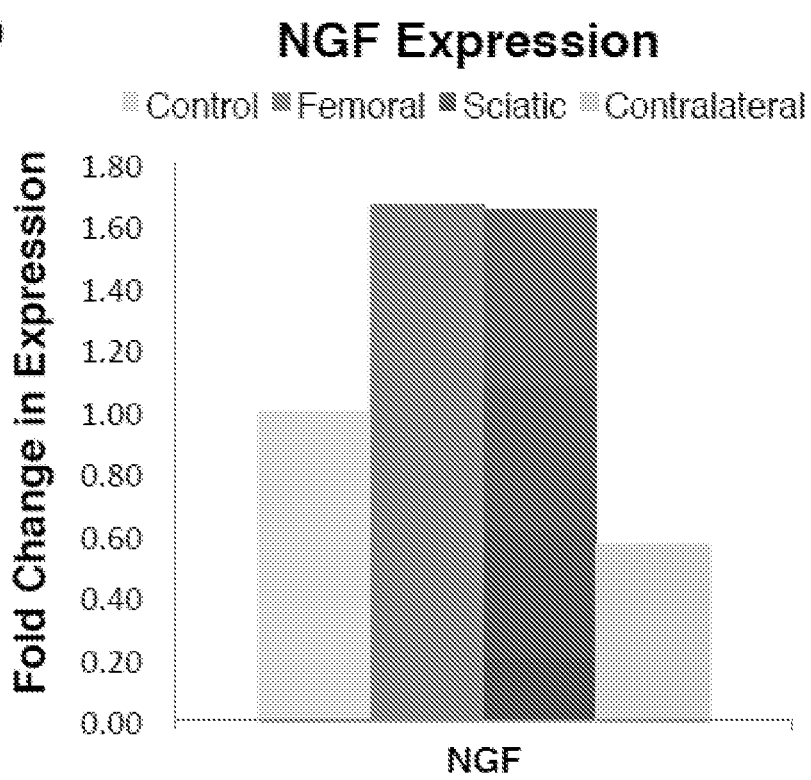
Figs. 22C-D

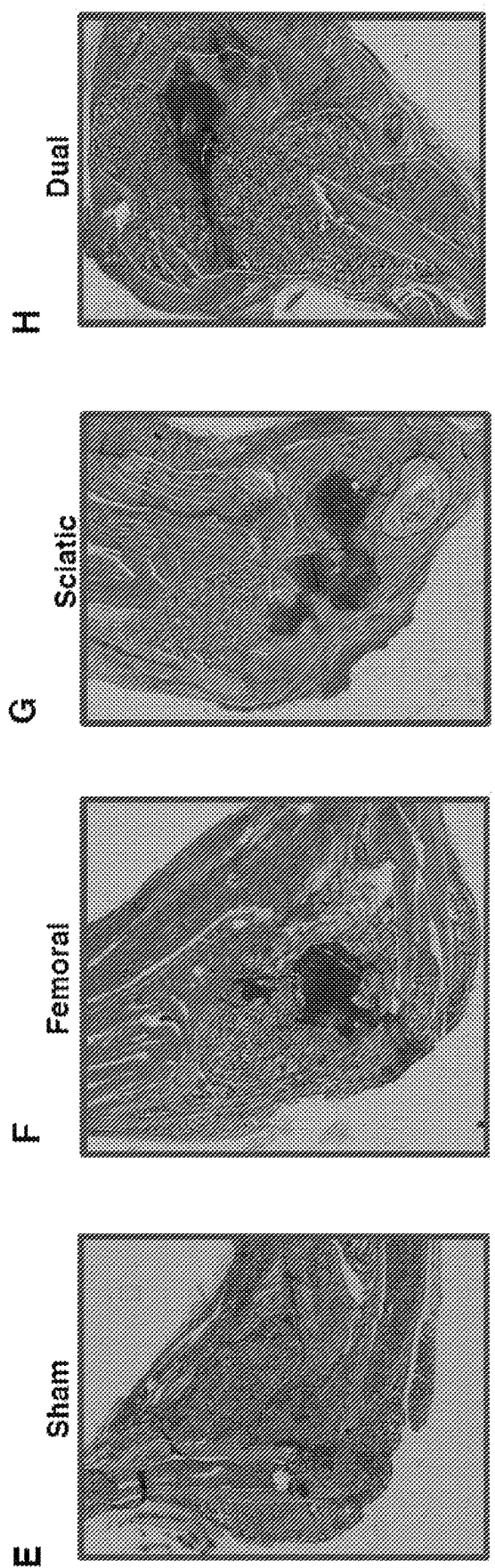
Figs. 22E-H

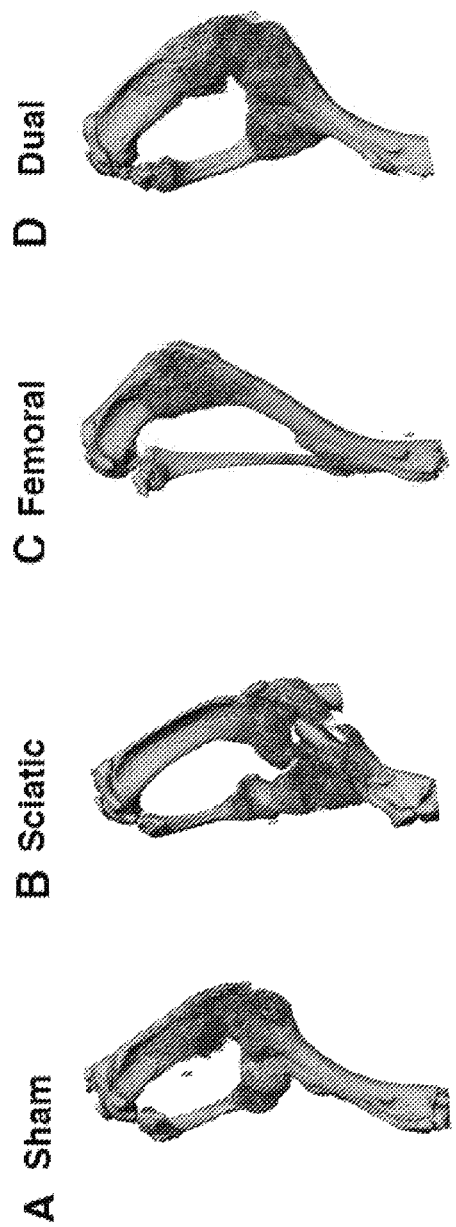
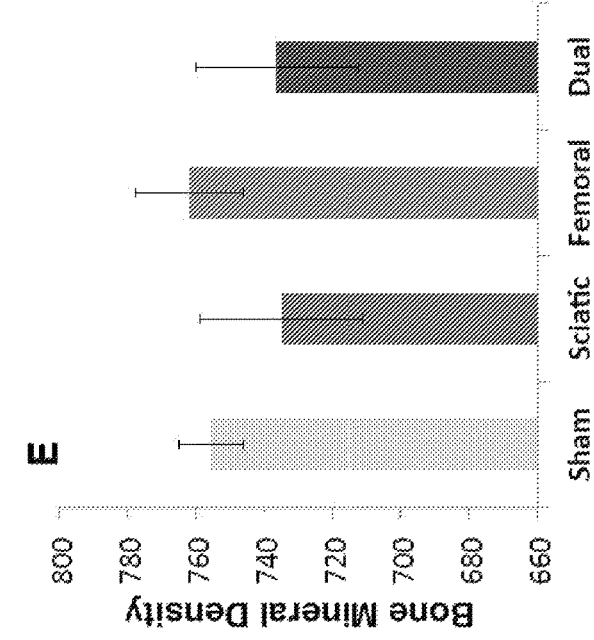
Figs. 23A-F

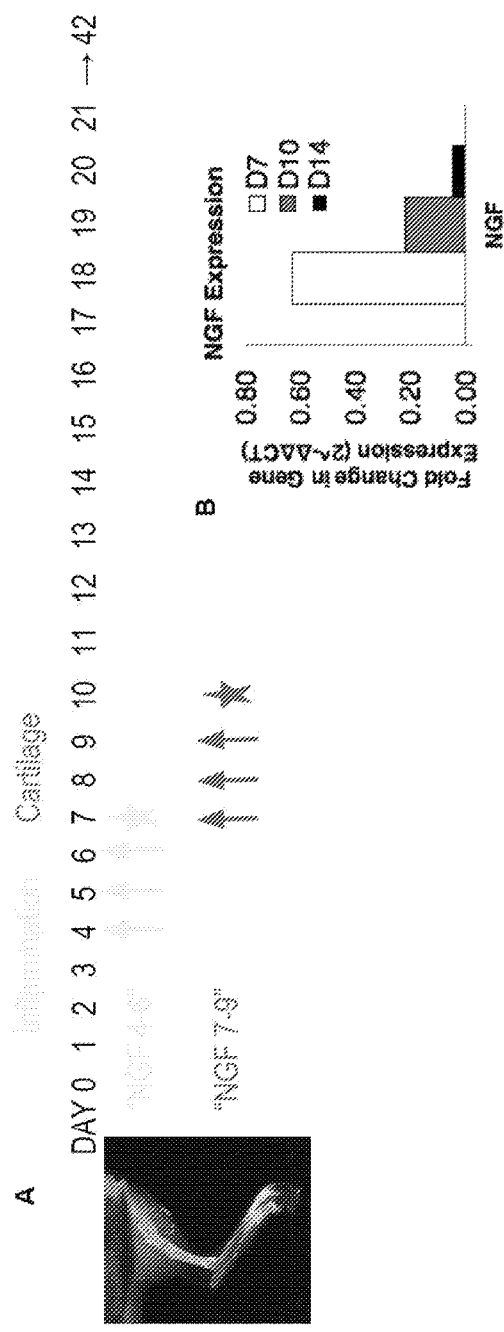
Figs. 24A-B
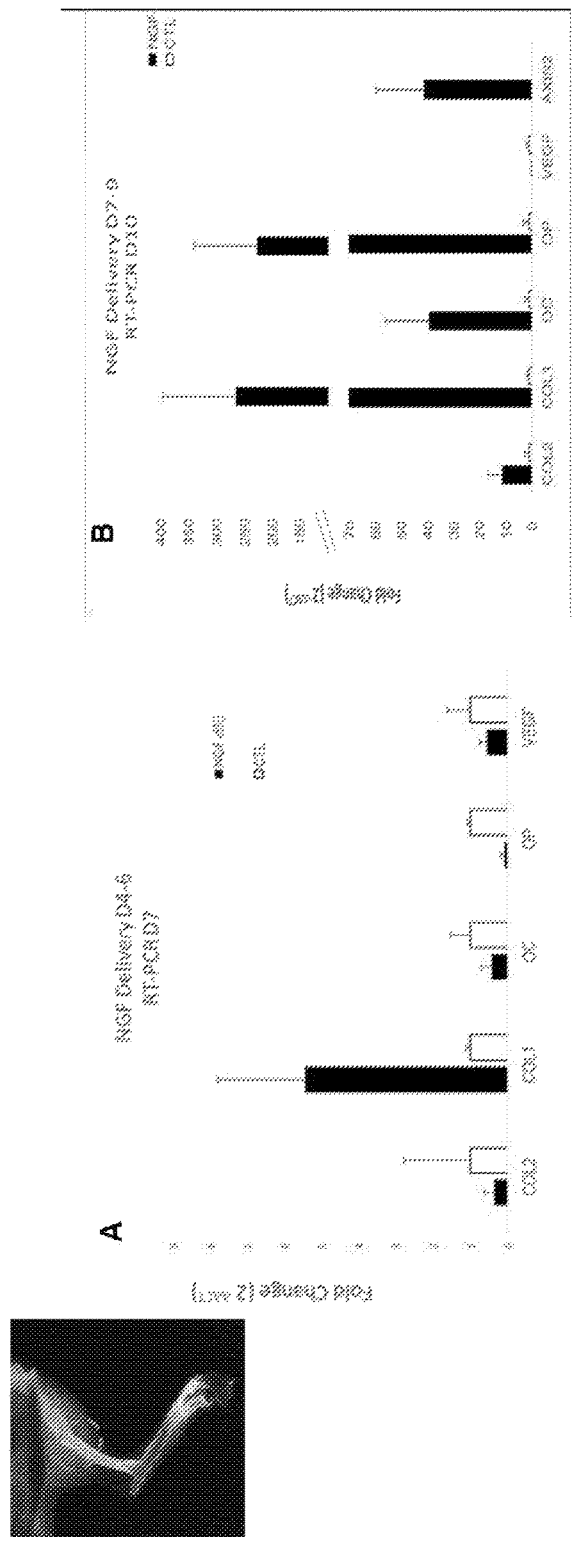
Figs. 25A-B

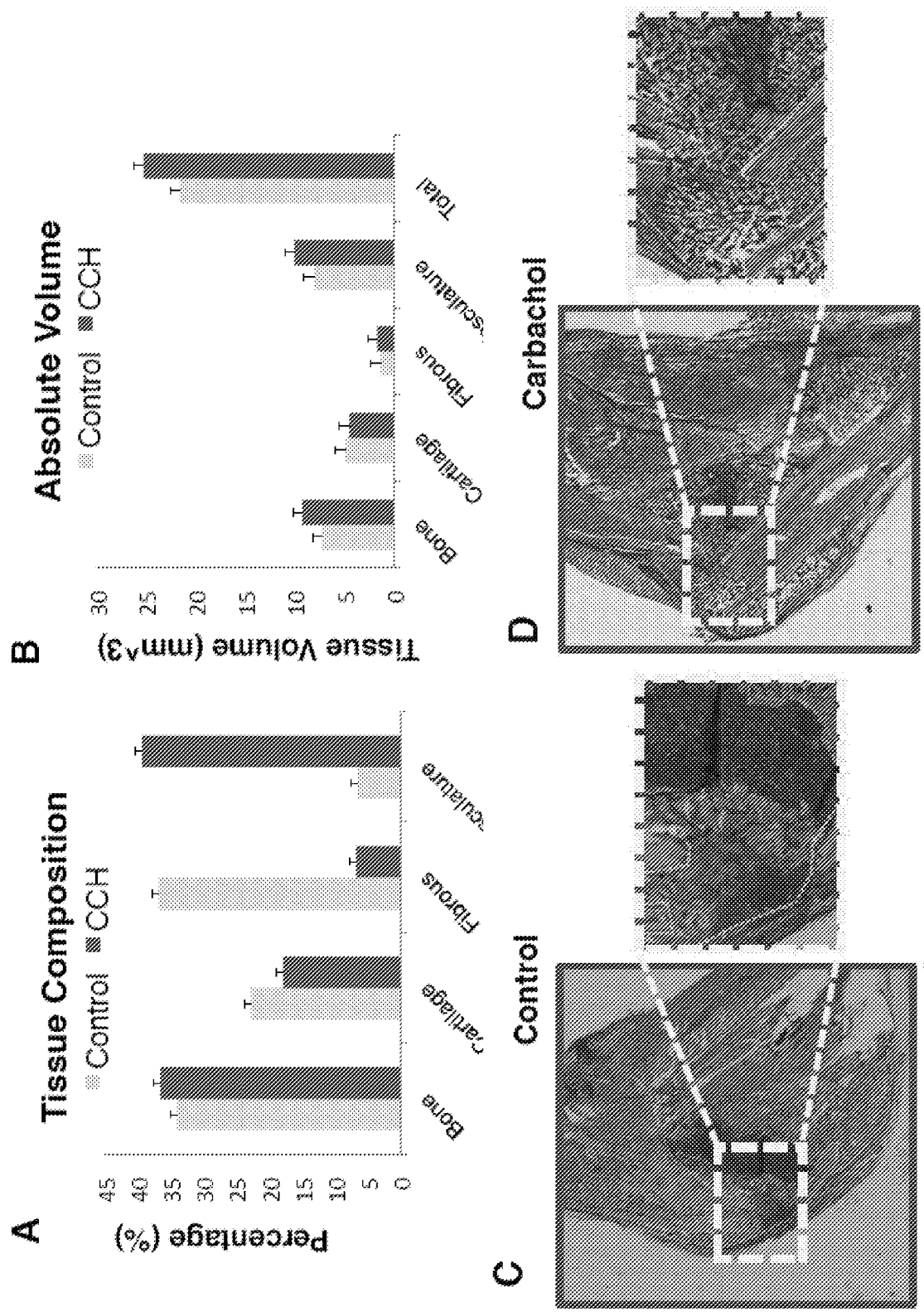
Figs. 26A-D

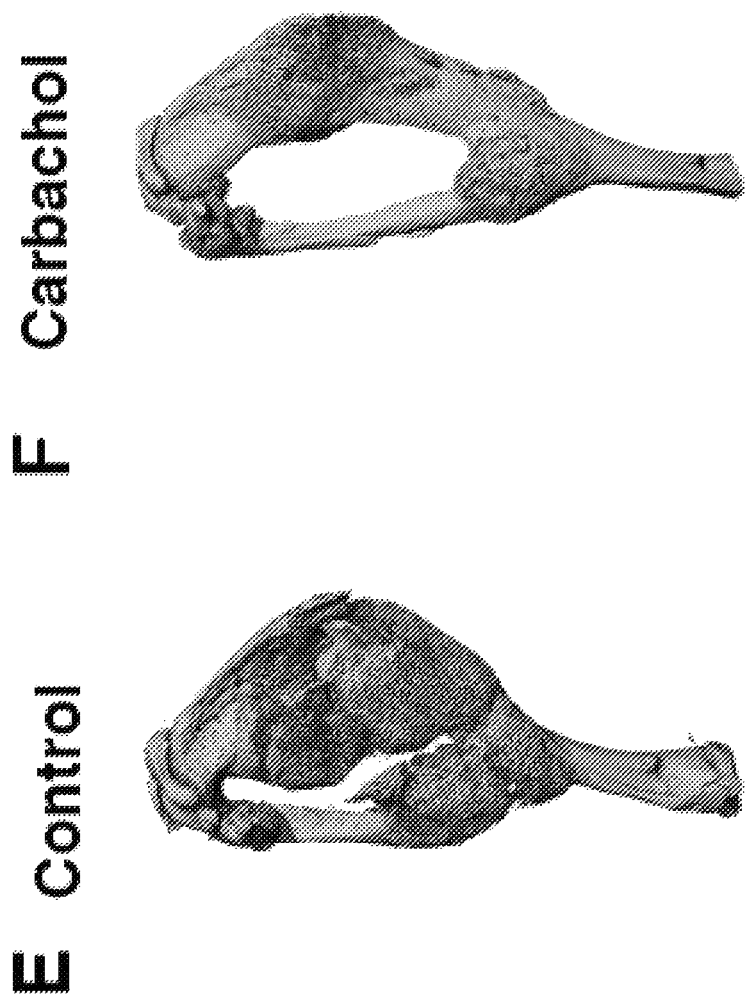
Figs. 26E-F

COMPOSITIONS AND METHODS OF MODULATING ENDOCHONDRAL OSSIFICATION AND BONE FORMATION

RELATED APPLICATION

This application claims priority from U.S. Provisional Application No. 62/432,580, filed Dec. 11, 2016, the subject matter of which is incorporated herein by reference in its entirety.

BACKGROUND

There are an estimated 15 million fractures annually in the United States. Under normal conditions, between 10-20% of fractures do not heal properly. However, a compromised vasculature, co-morbidities (diabetes, smoking, aging, obesity), trauma with extensive soft-tissue damage or segmental gaps larger than 2-3 cm can result in delayed- or non-union rates close to 50%. In situations of malunion, treatment can be delayed 3-6 months to confirm diagnosis, and then these fractures can be treated surgically to stimulate bone healing. Stimulation of bone healing depends on the classification of non-union, but (in the absence of infection) is typically attempted through supplementation with osteogenic substrates, such as bone grafts, improving blood supply, or increasing stabilization. Taken together fractures represent an estimated $45 billion cost burden on the healthcare system.

Fracture healing begins with an acute inflammatory response that produces a hematoma to isolate the damaged tissue, and then new bone arises by both intramembranous and endochondral ossification. Differentiation of progenitor cells into chondrocytes or osteoblasts depends on the local mechanical microenvironment. Along the periosteal and endosteal surfaces, progenitor cells undergo direct bone formation, or intramembranous ossification. In the fracture gap, where there is motion, the progenitors differentiate into chondrocytes and healing occurs through endochondral ossification. During healing, these chondrocytes undergo maturation towards hypertrophy and become highly angiogenic. The chondrocytes induce vascular invasion of the cartilage callus and this corresponds with mineralization of the cartilage matrix and formation of the trabecular bone. The newly formed bone is remodeled into cortical bone through coordinated actions of osteoblasts and osteoclasts.

The source of the osteoblasts that give rise to bone during endochondral ossification remains controversial. Two models have been proposed: one in which the hypertrophic chondrocytes undergo programmed cell death and the progenitor cells enter the cartilage callus with the invading vasculature, and replace the cartilage with bone. Alternatively, some hypertrophic chondrocytes do not undergo programmed cell death, and instead transdifferentiate into osteoblasts.

SUMMARY

Embodiments described herein relate to methods of modulating transdifferentiation of chondrocytes to osteoblasts, treating bone injuries, and/or promoting bone growth, bone healing, and/or bone regeneration. The methods described herein include administering to chondrocytes an agent that modulates GP130 receptor signaling and expression of at least one of Sox2, Oct4, or Nanog of the chondrocytes. The agent can activate GP130 receptor signaling to induce a pluripotency like state that primes the chondrocytes for differentiation to osteoblasts.

In some embodiments, the agent that activates GP130 receptor signaling to induce a pluripotency like state, which primes the chondrocytes for differentiation to osteoblasts, can include at least one of leukemia inhibitory factor (LIF), an LIF receptor agonist, a GP130 receptor agonist, or interleukin-6 cytokine.

The chondrocytes that are induced by the agent to a pluripotency like state can be in a subject at a site of bone fracture, bone disease, bone injury, or bone abnormality, such as a delayed union fracture, nonunion fracture, hypertrophic nonunion, or growth plate disorder. In some embodiments, the agent can be administered locally to soft cartilage callus at the site of the bone fracture, bone disease, bone injury, or bone abnormality. For example, at least one of LIF, an LIF receptor agonist, a GP130 receptor agonist, or interleukin-6 cytokine can be injected directly into soft cartilage callus at a bone fracture site.

In other embodiments, the chondrocytes can be provided in at least one of a cartilage graft or tissue engineered construct.

In some embodiments, an agent that activates canonical Wnt signaling in the chondrocytes can be administered to the chondrocytes following administration of the agent that activates GP130 receptor signaling in the chondrocytes. The agent that activates canonical Wnt signaling in the chondrocytes can promote differentiation of the activated or hypertrophic chondrocytes to osteoblasts.

In some embodiments, the agent that activates canonical Wnt signaling in the chondrocytes can include at least one of a Wnt ligand or agonist or an inhibitor of a negative regulator of Wnt signaling. The Wnt ligand or agonist can include at least one of a frizzled receptor agonist, Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, Wnt16, Norrin ligand, or R-spondin2. The inhibitor of a negative regulator of Wnt signaling can include at least one of a glycogen synthase kinase 3 (GSK-3) inhibitor, a PKA inhibitor, a PKC inhibitor, a MEK1/2 inhibitor, a MAPK inhibitor, a JNK inhibitor, a DKK inhibitor, or a sclerostin inhibitor. The ligand or agonist or an inhibitor of a negative regulator of Wnt signaling can be injected directly into soft cartilage callus at a bone fracture site to promote differentiation of the activated or hypertrophic chondrocytes to osteoblasts.

In other embodiments, at least one of a cholinergic agonist, muscarinic agonist, or nicotinic agonist can be administered to the chondrocytes to promote bone regeneration. The cholinergic agonist can be selected from the group consisting of acetylcholine, bethanechol, carbachol, methacholine, arecoline, nicotine, galantamine, cevimeline, levamisole, muscarine, pilocarpine, donepezil, edrophonium, neostigmine, physostigmine, pyridostigmine, rivastigmine, tacrine, caffeine, huperzine, echothiophate, isofluorophate, cisapride, droperidol, domperidone, metoclopramide, risperidone and paliperidone. In other embodiments, the cholinergic agonist can include at least one of acetylcholine or an acetylcholine analogue. For example, the acetylcholine analogue can include carbachol.

In some embodiments, the muscarinic agonist encompasses agonists that activate muscarinic acetylcholine receptors ("muscarinic receptors"). Muscarinic agonists can include but are not limited to pilocarpine, aceclidine, xanomeline, talsaclidine, sabcomeline, cevimeline, alvameline, arecoline, milameline, SDZ-210-086, YM-796, RS-86, CDD-0102A (5-[3-ethyl-1,2,4-oxasdiazol-5-yl]-1,4,5,6-tetrahydropyrimidine hydrocholoride), N-arylurea-substituted 3-morpholine arecolines, VUO255-035 (N-[3-oxo-3-[4-(4-pyridinyl)-1-piperazinyl]propyl]-2,1,3-benzothiadiazole-4-sulfonamide), benzylquinolone carboxylic acid (BQCA), WAY-132983, AFB267B (NGX267), AC-42, AC-260584, chloropyrazines including but not limited to L-687, 306, L-689-660, 77-LH-28-1, LY593039, and any quiniclidine ring with one or more carbon substitutions particularly that include an ester, sulfur, or 5 or 6 carbon ring structure including with substituted nitrogen(s) and or oxygen(s), or any pharmaceutically acceptable salts, esters, analogues, prodrugs or derivatives thereof.

In some embodiments, the nicotinic agonist can include nicotine, nicotine metabolites, decamethonium bromide, epibatidine, lobeline, varenicline, epiboxidine, epiquinamide; ABT 418, i.e., (S)-3-methyl-5-(1-methyl-2-pyrrolidinyl) isoxazole, an isoxazole analog of (−)-nicotine that is an α4β2 nAChR agonist; ABT-594, an azetidine derivative of epibatidine; ABT-894; DMXB-A, i.e., 3-(2,4-dimethoxybenzylidene)-anabaseine (also known as GTS-21), an α7-nAChR selective agonist; SIB-1508 (altinicline); and RJR 2403 (metanicotine), and pharmaceutically acceptable salts and isomers thereof. Examples of active nicotine metabolites contemplated include cotinine, nomicotine, norcotinine, nicotine N-oxide, cotinine N-oxide, 3-hydroxycotinine, 5-hydroxy-cotinine and pharmaceutically acceptable salts thereof.

Other embodiments describe herein relate to a method of inducing bone formation, bone repair, and/or bone regeneration in a subject in need thereof. The method can include administering to chondrocytes of the subject a therapeutically effective amount of at least one, two, or three or more of: (i) an agent activates GP130 receptor signaling (GP130 receptor signaling activator) to induce transdifferentiation of the chondrocytes to osteoblasts; (ii) an agent that activates canonical Wnt signaling (Wnt signaling activator) in the chondrocytes; or (iii) at least one of a cholinergic agonist, muscarinic agonist, or nicotinic agonist.

In some embodiments, the GP130 receptor signaling activator induces a pluripotency like state that primes the chondrocytes for differentiation to osteoblasts, the Wnt signaling activator can promote differentiation of the chondrocytes to osteoblasts, and the cholinergic agonist, muscarinic agonist, or nicotinic agonist can mimic neuronal signaling and promote mineralization and healing of bone as well as activate SOX2 in the chondrocytes.

In some embodiment, the GP130 receptor signaling activator; the Wnt signaling activator, the cholinergic agonist, the muscarinic agonist, and/or nicotinic agonist can be administered to chondrocytes in a subject at a site of bone fracture, bone disease, bone injury, or bone abnormality.

In some embodiments, the GP130 receptor signaling activator, the Wnt signaling activator, cholinergic agonist, muscarinic agonist, and/or nicotinic agonist can be administered locally by, for example, direct injection into soft cartilage callus at the site of bone fracture, bone disease, bone injury, or bone abnormality.

In some embodiments, the bone injury includes at least one of a delayed union fracture, nonunion fracture, hypertrophic nonunion, or growth plate disorder.

In other embodiments, the chondrocytes to which the GP130 receptor signaling activator, the Wnt signaling activator, cholinergic agonist, muscarinic agonist, and/or nicotinic agonist can be administered are provided in at least one of a cartilage graft or tissue engineered construct.

Still other embodiments relate to a method of treating at least one of a delayed union bone fracture, nonunion bone fracture, or hypertrophic bone nonunion in a subject in need thereof. The method includes administering to soft cartilage callus at a site of the bone fracture or bone nonunion a therapeutically effective amount of at least one, two, or three or more of: (i) an agent activates GP130 receptor signaling (GP130 receptor signaling activator) to induce transdifferentiation of the chondrocytes to osteoblasts; (ii) an agent that activates canonical Wnt signaling (Wnt signaling activator) in the chondrocytes; or (iii) at least one of a cholinergic agonist, muscarinic agonist, or nicotinic agonist.

In some embodiments, the GP130 receptor signaling activator, the Wnt signaling activator, cholinergic agonist, muscarinic agonist, and/or nicotinic agonist can be administered locally by, for example, direct injection into soft cartilage callus at the site of bone fracture, bone disease, bone injury, or bone abnormality.

In other embodiments, the chondrocytes to which the GP130 receptor signaling activator, the Wnt signaling activator, cholinergic agonist, muscarinic agonist, and/or nicotinic agonist can be administered are provided in at least one of a cartilage graft or tissue engineered construct. In other embodiments, at least one of a cartilage graft or tissue engineered construct can be administered in combination with the GP130 receptor signaling activator, the Wnt signaling activator, cholinergic agonist, muscarinic agonist, and/or nicotinic agonist to the site of the bone fracture or bone nonunion.

Still other embodiments relate to a composition for treatment of a tissue injury. The composition can include a carrier material that comprises a polymeric macro- or micro-scaffold and/or a plurality of biocompatible and biodegradable nanoparticles and/or microparticles, at least one bioactive agent provided on or in the polymeric macro- or micro-scaffold and/or a plurality of biocompatible and biodegradable nanoparticles and/or microparticles, and optionally osteochondrogenic cells. The bioactive agent can include at least one of an agent activates GP130 receptor signaling (GP130 receptor signaling activator) to induce transdifferentiation of chondrocytes to osteoblasts, an agent that activates canonical Wnt signaling (Wnt signaling activator) in the chondrocytes, or at least one of a cholinergic agonist, muscarinic agonist, or nicotinic agonist.

Other embodiments relate to a method of inhibiting transdifferentiation of chondrocytes to osteoblasts by administration to the chondrocytes an agent that inhibits GP130 receptor signaling. The agent can include, for example, at least one of a LIF antagonist, a LIF receptor antagonist, a GP130 receptor antagonist, or an IL-6 antagonist. For example, the agent can include at least one of an IL-6R antibody or IL-27p28.

In some embodiments, the agent that inhibits GP130 receptor signaling to inhibit transdifferentiation of the chondrocytes can be administered to a subject having or at risk of heterotopic ossification.

In other embodiments, the agent that inhibits GP130 receptor signaling to inhibit transdifferentiation of the chondrocytes can be administered to a subject having, during, or following a traumatic injury or surgery.

BRIEF DESCRIPTION OF THE DRAWINGS

FIGS. 13(A-D) illustrate images showing the expression of IL-6 family pathway. Immunohistochemistry on a day 14 fracture to (A) the LIF ligand, (B) LIF receptor GP130, and downstream effectors (C) Tbx3 and (D) Klf4 in transition zone indicate pathway is active.

FIGS. 14(A-B) illustrate graphs showing LIF-pathway mediates expression pluripotency genes (A) LIF induces Sox2 and Oct4 expression in fracture callus explants cultured. (B) Klf4 specific antisense morpholino knocks down expression of Sox2, Nanog, and Oct4 in fracture explants.

FIGS. 15(A-B) illustrate images showing Pin-stabilized fractures promote robust endochondral healing. (A) Intramedullary insect pin is in the tibia immediately post-operatively. (B) HBQ histology (bone stains red) of tibia shows that bone heals completely by 28-days.

FIGS. 16(A-B) illustrate an image and graph showing Wnt signaling in chondroctyes at transition zone. (A) Immunohistochemistry for nuclear β-catenin shows that chondrocytes in transition zone, but not other chondrocytes, have active Wnt signaling. (B) Luciferase activity on 293 cells transfected with Super TopFlash from HUVEC-CM compared to Wnt3a and WntS.

FIGS. 17(A-E) illustrate graphs and images showing Wnt Surrogate activates canonical Wnt (A) Binding to Frizzled Receptors 2, 4, 5, 7, 8. (B) Induces downstream axin2 expression, (C) activates 375-BAR Wnt reporter cells, (D) leads to nuclear localization of b-catenin, and (E) activates cell proliferation.

FIGS. 18(A-D) illustrate graphs and images showing WntS promotes intramembranous bone formation (A) Axin2 gene expression on MC3T3 cells compared to positive control GSK inhibitor SB216763, (B) 7-day alkaline phosphatase activity for WntS on hMSCs compared to positive osteogenic control (dexamethasone), (C-D) 2 wk alizarin red staining for mineralization for 3 concentrations of WntS compared to BMP for (C) MC3T3 and (D) hMSCs.

FIGS. 20(A-C) illustrate a schematic and plots showing alginate hydrogels for controlled release of WntS. (A) Schematic diagram of affinity and aldehyde mediated interaction between oxidized alginate and WntS to mediate controlled release, (B) Physical degradation of a 4 wt % calcium alginate hydrogel with 5% oxidation (C) Positive chondrocytes in the TZ (red arrows), (C) White blood cell count following WntS injection in to fracture either 2-4 or 9-11 days post-fracture shows that delayed delivery to fracture does not activate systemic immune response.

FIG. 21 illustrates changes to muscarinic receptor, neural cell marker and nerve growth factor expression during endochondral fracture repair.

FIGS. 22(A-H) illustrate graphs and images showing nerve resection leads to changes in gene expression and fracture callus composition.

FIGS. 23(A-F) illustrates images and graphs showing lower bone mineral density and volume in sciatic and dual nerve resection groups assessed by μCT.

FIGS. 24(A-B) illustrate plots showing the temporal therapeutic delivery of NGF to improve bone fracture healing in mice. (A) Timeline of experimental delivery of NGF to bone fracture site for two different post-fracture time ranges. (B) NGF expression decreases over time post-fracture.

FIG. 25 illustrates a plot showing a more delayed therapeutic delivery of NGF was more effective in activating bone healing. Compared to delayed NGF delivery at 4-6 days following fracture induction, delayed NGF delivery at 7-9 days post-fracture showed more robust activation of selected bone healing markers.

FIGS. 26(A-F) illustrate graphs and images showing the therapeutic effect of cholinergic agonists on fracture healing.

DETAILED DESCRIPTION

Figure 1:
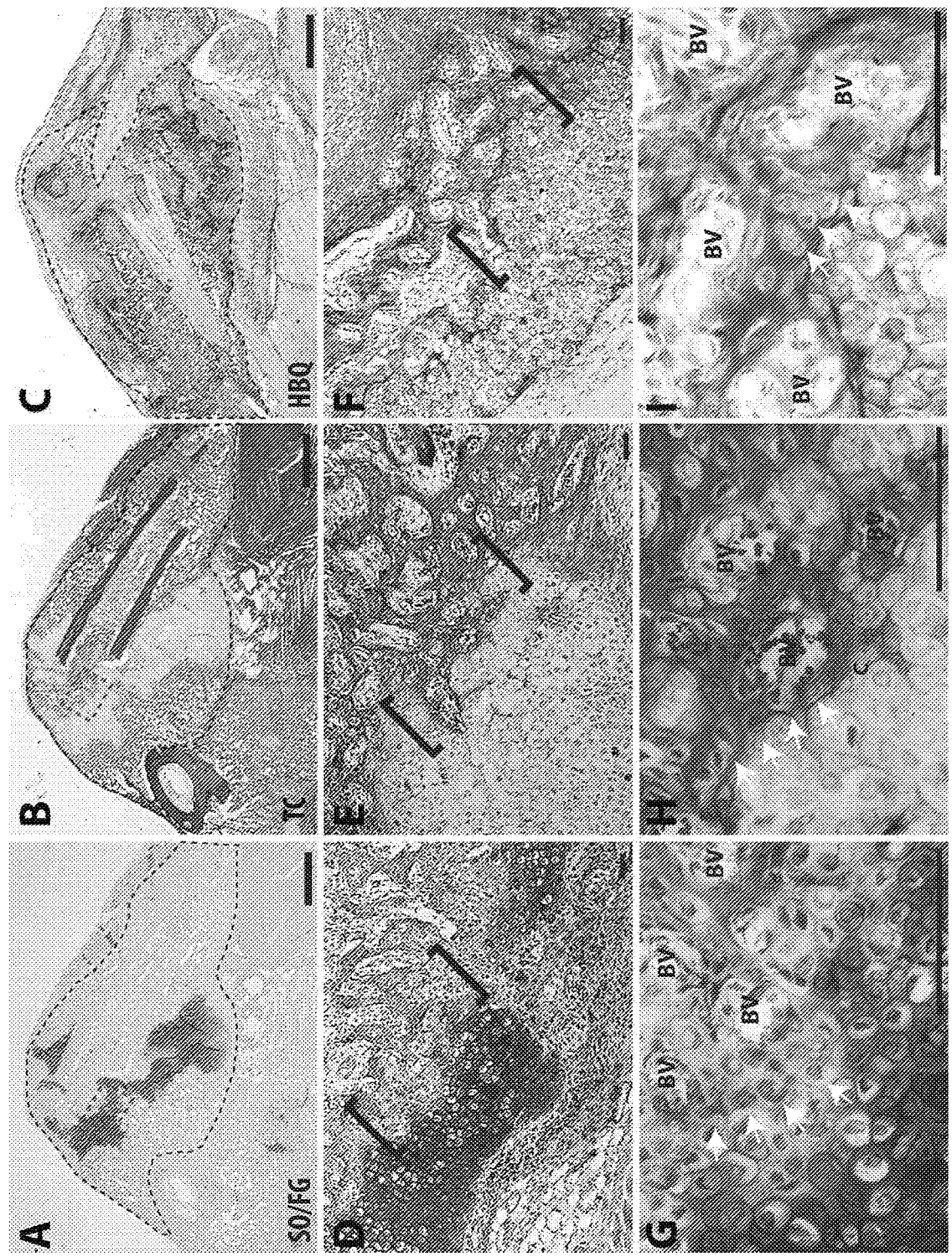
FIGS. 1(A-H) illustrate images showing chondro-osseous transition zone in a fracture callus. (A-C) Low magnification of a murine fracture callus, outlined with black dashed line, stained with (A) Safranin-O/Fast Green (SO/FG), (B) Modified Milligan's Trichrome (TC) or (C) Hall and Brunt Quadruple Stain (HBQ). (D-F) A magnified region of cartilage and bone from the fracture callus, outlined with a box (A-C), with the TZ indicated by black brackets. (G-I) High magnification images of the TZ show the invading vasculature and the chondro-osseous junction. BV, blood vessel. Scale bars: 1 mm (A-C) and 100 μm (D-I).

The terms used herein have the meanings recognized and known to those of skill in the art, however, for convenience and completeness, particular terms and their meanings are set forth below.

The term "agent" refers to all materials that may be used to prepare pharmaceutical and diagnostic compositions, or that may be compounds such as small synthetic or naturally derived organic compounds, nucleic acids, polypeptides, antibodies, fragments, isoforms, variants, or other materials that may be used independently for such purposes, all in accordance with the present invention.

The term "agonist" refers to a substance that binds to a specific receptor and triggers a response in a cell. It mimics the action of an endogenous ligand (such as hormone or neurotransmitter) that binds to the same receptor. A "full agonist" binds (has affinity for) and activates a receptor, displaying full efficacy at that receptor. One example of a drug that acts as a full agonist is isoproterenol, which mimics the action of acetylcholine at β adrenoreceptors. A "partial agonist" (such as buspirone, aripiprazole, buprenorphine, or norclozapine) also binds and activates a given receptor, but has only partial efficacy at the receptor relative to a full agonist. A "partial agonist" may also be considered a ligand that displays both agonistic and antagonistic effects—when both a full agonist and partial agonist are present, the partial agonist actually acts as a competitive antagonist, competing with the full agonist for receptor occupancy and producing a net decrease in the receptor activation observed with the full agonist alone. A "co-agonist" works with other co-agonists to produce the desired effect together. An antagonist blocks a receptor from activation by agonists. Receptors can be activated or inactivated either by endogenous (such as hormones and neurotransmitters) or exogenous (such as drugs) agonists and antagonists, resulting in stimulating or inhibiting a biological response. A ligand can concurrently behave as agonist and antagonist at the same receptor, depending on effector pathways.

The potency of an agonist is usually defined by its $EC_{50}$ value. This can be calculated for a given agonist by determining the concentration of agonist needed to elicit half of the maximum biological response of the agonist. Elucidating an $EC_{50}$ value is useful for comparing the potency of drugs with similar efficacies producing physiologically similar effects. The lower the $EC_{50}$, the greater the potency of the agonist, and the lower the concentration of drug that is required to elicit a maximum biological response.

The term "antagonist" refers to an agent that down-regulates (e.g., suppresses or inhibits) at least one bioactivity of a protein. An "antagonist" or an agent that "antagonizes" may be a compound which inhibits or decreases the interaction between a protein and another molecule, e.g., a target peptide or enzyme substrate. An antagonist may also be a compound that down-regulates expression of a gene or which reduces the amount of expressed protein present. Methods for assessing the ability of an agent to "antagonize" or "inhibit" a receptor are known to those skilled in the art.

The terms "differentiate", "differentiation", "transdifferentiate", or "transdifferentiation" as used herein, generally refers to the process by which precursor or progenitor cells differentiate into specific cell types. In the present invention, the term refers to the process by which chondrocytes or osteochondrogenic cells, such as mesenchymal stem cells, become osteoblasts. Differentiated cells can be identified by their patterns of gene expression and cell surface protein expression. As used herein, the term "differentiate" refers to having a different character or function from the original type of tissues or cells. Thus, "differentiation" is the process or act of differentiating.

The terms "modulation" or "modulates" or "modulating" refers to up regulation (i.e., activation or stimulation), down regulation (i.e., inhibition or suppression) of a response, or the two in combination or apart, such as the ability to alter by either up-regulating or down-regulating the activity of a protein, nucleic acid encoding a protein, a pathway (e.g., the Wnt pathway), a protein within a pathway and the like.

The terms "treatment" or "treating" refers to therapy, prevention and prophylaxis and particularly refers to administering medicine or performing medical procedures on a patient, for either prophylaxis (prevention) or to cure or reduce the extent of or likelihood of occurrence of the infirmity or malady or condition or event. The treatments using the agents described herein may be provided to stimulate or promote bone regeneration, and/or treat bone injuries.

The terms "subject" or "patient" refers to a mammal, preferably a human, in need of treatment for a condition, disorder or disease.

An "effective amount" or a "therapeutically effective amount" is an amount sufficient to stimulate or promote bone regeneration or bone formation. For example, an "effective amount" for therapeutic uses is the amount of the composition comprising an active compound herein required to provide repair of nonunion bone fracture. Such effective amounts may be determined using routine optimization techniques and are dependent on the particular condition to be treated, the condition of the subject, the route of administration, the formulation, and the judgment of the practitioner and other factors evident to those skilled in the art. The dosage required for the compounds described herein is that which induces a statistically significant difference in bone formation. This difference in bone formation may be seen, for example, as at least 1-2%, or any clinically significant increase in bone mass in the treatment group.

The phrase "pharmaceutically acceptable" refers to molecular entities and compositions that are physiologically tolerable and do not typically produce an allergic or similar untoward reaction, such as gastric upset, dizziness and the like, when administered to a human Preferably, as used herein, the term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

Embodiments described herein relate to methods of modulating transdifferentiation of chondrocytes to osteoblasts, treating bone injuries, and/or promoting bone growth, bone healing, and/or bone regeneration. Fractures heal predominantly through the process of endochondral ossification. The classic model of endochondral ossification holds that hypertrophic chondrocytes are a transient cell population that undergo programmed cell death, and that new bone is formed by osteoprogenitors invading the cartilage matrix. We found, however, that chondrocytes themselves become osteoblasts during bone regeneration. The transformation of cartilage to bone is a multistep process that requires chondrocytes to acquire a stem cell like state by activating pluripotency programs (e.g., SOX2) and stimulation of vascularization, innnervation, and mineralization to facilitate osteoblastic conversion.

Accordingly, the following embodiments describe methods of modulating transdifferentiation of chondrocytes to osteoblasts to treat bone injuries and/or promote bone growth, bone healing, and/or bone regeneration by administering to chondrocytes an agent that promotes or inhibits a stem cell like state and/or an agent that promotes or inhibits osteoblastic conversion. In some embodiments, the method includes administering to chondrocytes an agent that modulates GP130 receptor signaling and expression of at least one of Sox2, Oct4, or Nanog of the chondrocytes. Administration of an agent, which can activate GP130 receptor signaling, can induce a pluripotency like state that primes the chondrocytes for differentiation to osteoblasts. The pluripotency state can be identified by enhanced expression of at least one of Sox2, Oct4, or Nanog by the hypertrophic chondrocytes compared to untreated chondrocytes.

In some embodiments, the agent that activates GP130 receptor signaling to induce a pluripotency like state, which primes the chondrocytes for differentiation to osteoblasts can include at least one of leukemia inhibitory factor (LIF), an LIF receptor agonist, a GP130 receptor agonist, or interleukin-6 cytokine.

The chondrocytes that are induced by the agent to osteoblasts can be in a subject at a site of bone fracture, bone disease, bone injury, or bone abnormality, such as a delayed union fracture, nonunion fracture, hypertrophic nonunion, or growth plate disorder. The agent can be administered locally to soft cartilage callus at the site of the bone fracture, bone disease, bone injury, or bone abnormality. For example, at least one of LIF, an LIF receptor agonist, a GP130 receptor agonist, or interleukin-6 cytokine can be injected directly into soft cartilage callus at a bone fracture site.

In other embodiments, the chondrocytes can be provided in at least one of a cartilage graft or tissue engineered construct that can be administered to a subject. By way of example, the tissue engineered construct can include a polymeric macro- or micro-scaffold, a plurality of chondrocytes dispersed within or on the polymeric macro- or micro-scaffold, and at least one carrier material incorporated on or within the polymeric macro- or micro-scaffold. The at least one carrier material can include a material capable of carrying and differentially and/or controllably releasing at least one bioactive agent, such as leukemia inhibitory factor (LIF), an LIF receptor agonist, a GP130 receptor agonist, or interleukin-6 cytokine to the chondrocytes.

In other embodiments, following administration of LIF, an LIF receptor agonist, a GP130 receptor agonist, or interleukin-6 cytokine to the chondrocytes to activate GP130 receptor signaling and induce a temporary stem cell like state to the chondrocytes, an agent that activates canonical Wnt signaling in the chondrocytes can be administered to the chondrocytes to promote differentiation of the activated chondrocytes (e.g., chondrocytes in a temporary stem cell like state) to osteoblasts.

In some embodiments, the agent that activates canonical Wnt signaling can include at least one of a Wnt ligand or agonist or an inhibitor of a negative regulator of Wnt signaling. For example, the Wnt ligand or agonist can include at least one of a frizzled receptor agonist, Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, Wnt16, Norrin ligand, or R-spondin2. Such Wnt ligands, as well as their accession numbers, are described in U.S. Pat. No. 8,460,928, which is herein incorporated by reference.

Wnt ligands may be obtained from R&D Systems (Minnesota, USA) and from PeproTech, Inc (New Jersey, USA).

In some embodiments, the Wnt ligand comprises Wnt1 or Wnt3A, such as Wnt3A. The Wnt ligand may comprise Human WNT1 (PAL1) (ATCC 57198/57199), Human WNT1 (MGC 30915522), Human WNT3 (pHP1) (ATCC MBA-174), Mouse Wnt3 (ATCC MBA-175) or Mouse Wnt3A (ATCC MBA-176).

In addition, the Norrin ligand (Xu et al., 2004, Cell 116(6):883-95), which binds to Frizzled with high affinity, may be used to activate the Wnt signalling pathway. The R-spondin2 protein (Kazanskaya et al (2004) Dev Cell. 7(4):525-34 and Kim et al., (2005) Science 309(5738):1256-9) also binds to the Frizzled receptors and may similarly be used in the methods and compositions described here.

The inhibitor of a negative regulator of Wnt signaling can include at least one of a glycogen synthase kinase 3 (GSK-3) inhibitor, a PKA inhibitor, a PKC inhibitor, a MEK1/2 inhibitor, a MAPK inhibitor, a JNK inhibitor, a DKK inhibitor, or a sclerostin inhibitor.

For example, pharmacological inhibitors of GSK-3 can be used as direct intracellular activators of the canonical Wnt pathway. The stability of beta-catenin, the operative molecule of the canonical Wnt pathway, is controlled by glycogen synthase kinase 3 (GSK-3) via phosphorylation and subsequent degradation. Upon Wnt pathway activation, GSK-3 is inhibited, and the non-phosphorylated beta-catenin is stabilized and enters the nucleus to activate transcription of Wnt-regulated genes. (See Gregorieff et al., (2005) Genes Dev. 19, 877-890). GSK-3 inhibitors (also referred to herein as GSK-3β inhibitors) include, but are not limited to, commercially available GSK-3 inhibitors, for example, those inhibitors available through EMD Biosciences, Madison, Wis., including 1-Azakepaullone, Aloisine, Alsterpaullone, FRATtide (188-225 amino acids of FRAT1), GSK-3 Inhibitor No. IX, X, XIII, XIV, XV, and GSK-3beta Inhibitor I, II, III, VI, VII, VIII, IX, XI, XII, Peptide Inhibitor (Cat. 361545 and 361546), Indirubin-3'-monoxime, Indirubin-3'-monoxime 5-Iodo, Indirubin-3'-monoxime-5-sulfonic Acid, and Kenpaullone and functional derivatives thereof. Other known GSK-3 inhibitors include small molecules, such as lithium, bivalent zinc, beryllium, aloisines, hymenialdisine, indirubins, maleimides, muscarinic agonists, pyridazinone derivatives, e.g., pyrazolo[3,4-b]quinoxalines, 5-aryl-pyrazolo[3,4-b]pyridazines, and functional derivatives thereof.

Similar to the agent that activates GP130 receptor signaling, the agent that activates canonical Wnt signaling can be administered locally to soft cartilage callus at the site of the bone fracture, bone disease, bone injury, or bone abnormality as well as to chondrocytes provided in at least one of a cartilage graft or tissue engineered construct that can be administered to a subject. For example, the agent that activates canonical Wnt signaling can be injected directly into soft cartilage callus at a bone fracture site.

In other embodiments, an agent that mimics neuronal signaling can be administered to the chondrocytes to promote bone regeneration. It was found that innervation of bone fractures facilitates conversion of cartilage to bone during endochondral bone repair and that activation of neuronal receptors by an agent that mimics neuronal signaling can, for example, promote mineralization and healing of bone as well as activate SOX2. Agents that mimic neuronal signaling can be administered alone to the chondrocytes and/or in combination with the agent that activates GP130 receptor signaling and/or the agent that activates canonical Wnt signaling.

In some embodiments, the agent that mimics neuronal signaling to promote bone regeneration can include at least one of a cholinergic agonist, muscarinic agonist, or nicotinic agonist as well as nerve growth factor.

In some embodiments, the cholinergic agonist can be selected from the group consisting of acetylcholine, bethanechol, carbachol, methacholine, arecoline, nicotine, galantamine, cevimeline, levamisole, muscarine, pilocarpine, donepezil, edrophonium, neostigmine, physostigmine, pyridostigmine, rivastigmine, tacrine, caffeine, huperzine, echothiophate, isoflurophate, cisapride, droperidol, domperidone, metoclopramide, risperidone and paliperidone. In other embodiments, the cholinergic agonist can include at least one of acetylcholine or an acetylcholine analogue. For example, the acetylcholine analogue can include carbachol.

In some embodiments, the muscarinic agonist can include agonists that activate muscarinic acetylcholine receptors ("muscarinic receptors"). Muscarinic receptors are divided into five subtypes named M1-M5. Muscarinic agonists can include but are not limited to pilocarpine, aceclidine, xanomeline, talsaclidine, sabcomeline, cevimeline, alvameline, arecoline, milameline, SDZ-210-086, YM-796, RS-86, CDD-0102A (5-[3-ethyl-1,2,4-oxasdiazol-5-yl]-1,4,5,6-tetrahydropyrimidine hydrocholoride), N-arylurea-substituted 3-morpholine arecolines, VUO255-035 (N-[3-oxo-3-[4-(4-pyridinyl)-1-piperazinyl]propyl]-2,1,3-benzothiadiazole-4-sulfonamide), benzylquinolone carboxylic acid (BQCA), WAY-132983, AFB267B (NGX267), AC-42, AC-260584, chloropyrazines including but not limited to L-687, 306, L-689-660, 77-LH-28-1, LY593039, and any quiniclidine ring with one or more carbon substitutions particularly that include an ester, sulfur, or 5 or 6 carbon ring structure including with substituted nitrogen(s) and or oxygen(s), or any pharmaceutically acceptable salts, esters, analogues, prodrugs or derivatives thereof.

In some embodiments, the nicotinic agonist can include nicotine, nicotine metabolites, decamethonium bromide, epibatidine, lobeline, varenicline, epiboxidine, epiquinamide; ABT 418, i.e., (S)-3-methyl-5-(1-methyl-2-pyrrolidinyl) isoxazole, an isoxazole analog of (−)-nicotine that is an α4β2 nAChR agonist; ABT-594, an azetidine derivative of epibatidine; ABT-894; DMXB-A, i.e., 3-(2,4-dimethoxybenzylidene)-anabaseine (also known as GTS-21), an α7-nAChR selective agonist; SIB-1508 (altinicline); and RJR 2403 (metanicotine), and pharmaceutically acceptable salts and isomers thereof. Examples of active nicotine metabolites contemplated include cotinine, nomicotine, norcotinine, nicotine N-oxide, cotinine N-oxide, 3-hydroxy-cotinine, 5-hydroxy-cotinine and pharmaceutically acceptable salts thereof. Examples of nicotine salts include nicotine citrate and nicotine maleate. In a preferred embodiment, the nicotinic agonist is nicotine or a pharmaceutically acceptable salt or N-oxide thereof.

Similar to the agent that activates GP130 receptor signaling and the agent that activates canonical Wnt signaling, the agent that mimics neuronal signaling can be administered locally to soft cartilage callus at the site of the bone fracture, bone disease, bone injury, or bone abnormality as well as to chondrocytes provided in at least one of a cartilage graft or tissue engineered construct that can be administered to a subject. For example, agent that mimics neuronal signaling can be injected directly into soft cartilage callus at a bone fracture site.

In some embodiments, a method of inducing bone formation, bone repair, and/or bone regeneration in a subject in need thereof can include administering to chondrocytes of the subject a therapeutically effective amount of at least one, two, or three or more of: (i) an agent activates GP130 receptor signaling (GP130 receptor signaling activator) to induce transdifferentiation of the chondrocytes to osteoblasts; (ii) an agent that activates canonical Wnt signaling (Wnt signaling activator) in the chondrocytes; or (iii) at least one of a cholinergic agonist, muscarinic agonist, or nicotinic agonist.

In some embodiments, the GP130 receptor signaling activator induces a pluripotency like state that primes the chondrocytes for differentiation to osteoblasts. The GP130 receptor signaling activator can include, for example, at least one of leukemia inhibitory factor (LIF), an LIF receptor agonist, a GP130 receptor agonist, or interleukin-6 cytokine.

In other embodiments, the Wnt signaling activator can promote differentiation of the chondrocytes to osteoblasts. The Wnt signaling activator can include at least one of a Wnt ligand or agonist or an inhibitor of a negative regulator of Wnt signaling. For example, the Wnt ligand or agonist can include at least one of a frizzled receptor agonist, Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, Wnt16, Norrin ligand, or R-spondin2.

The inhibitor of a negative regulator of Wnt signaling can include at least one of a glycogen synthase kinase 3 (GSK-3) inhibitor, a PKA inhibitor, a PKC inhibitor, a MEK1/2 inhibitor, a MAPK inhibitor, a JNK inhibitor, a DKK inhibitor, or a sclerostin inhibitor.

The cholinergic agonist, muscarinic agonist, or nicotinic agonist can mimic neuronal signaling and promote mineralization and healing of bone as well as activate SOX2 in the chondrocytes.

In some embodiment, the GP130 receptor signaling activator; the Wnt signaling activator, the cholinergic agonist, the muscarinic agonist, and/or nicotinic agonist can be administered to chondrocytes in a subject at a site of bone fracture, bone disease, bone injury, or bone abnormality, such as a delayed union fracture, nonunion fracture, hypertrophic nonunion, or growth plate disorder, by, for example, direct injection into soft cartilage callus at the site of bone fracture, bone disease, bone injury, or bone abnormality.

In other embodiments, the chondrocytes to which the GP130 receptor signaling activator, the Wnt signaling activator, cholinergic agonist, muscarinic agonist, and/or nicotinic agonist can be administered are provided in at least one of a cartilage graft or tissue engineered construct.

Still other embodiments relate to a method of treating at least one of a delayed union bone fracture, nonunion bone fracture, or hypertrophic bone nonunion in a subject in need thereof. The method includes administering to soft cartilage callus at a site of the bone fracture or bone nonunion a therapeutically effective amount of at least one, two, or three or more of: (i) an agent activates GP130 receptor signaling (GP130 receptor signaling activator) to induce transdifferentiation of the chondrocytes to osteoblasts; (ii) an agent that activates canonical Wnt signaling (Wnt signaling activator) in the chondrocytes; or (iii) at least one of a cholinergic agonist, muscarinic agonist, or nicotinic agonist.

In other embodiments, the chondrocytes to which the GP130 receptor signaling activator, the Wnt signaling activator, cholinergic agonist, muscarinic agonist, and/or nicotinic agonist can be administered are provided in at least one of a cartilage graft or tissue engineered construct. In other embodiments, at least one of a cartilage graft or tissue engineered construct can be administered in combination with the GP130 receptor signaling activator, the Wnt signaling activator, cholinergic agonist, muscarinic agonist, and/or nicotinic agonist to the site of the bone fracture or bone nonunion.

The GP130 receptor signaling activator, the Wnt signaling activator, cholinergic agonist, muscarinic agonist, and/or nicotinic agonist described herein can be provided in a pharmaceutical composition. A pharmaceutical composition containing the GP130 receptor signaling activator, the Wnt signaling activator, cholinergic agonist, muscarinic agonist, and/or nicotinic agonist described herein as an active ingredient may be manufactured by mixing the GP130 receptor signaling activator, the Wnt signaling activator, cholinergic agonist, muscarinic agonist, and/or nicotinic agonist described herein with a pharmaceutically acceptable carrier(s) or an excipient(s) or diluting the GP130 receptor signaling activator, the Wnt signaling activator, cholinergic agonist, muscarinic agonist, and/or nicotinic agonist described herein with a diluent in accordance with conventional methods. The pharmaceutical composition may further contain fillers, anti-cohesives, lubricants, wetting agents, flavoring agents, emulsifying agents, preservatives and the like. The pharmaceutical composition may be formulated into a suitable formulation in accordance with the methods known to those skilled in the art so that it can provide an immediate, controlled, sustained, or delayed release of the GP130 receptor signaling activator, the Wnt signaling activator, cholinergic agonist, muscarinic agonist, and/or nicotinic agonist described herein after being administered into a mammal.

The pharmaceutical composition may be formulated into various dosage forms as discussed above and then administered through various routes including local, transdermal, subcutaneous, intravenous or intramuscular route. The dosage can be a pharmaceutically or therapeutically effective amount.

Therapeutically effective dosage amounts of the GP130 receptor signaling activator, the Wnt signaling activator, cholinergic agonist, muscarinic agonist, and/or nicotinic agonist described herein may be present in varying amounts in various embodiments. For example, in some embodiments, a therapeutically effective amount of the GP130 receptor signaling activator, the Wnt signaling activator, cholinergic agonist, muscarinic agonist, and/or nicotinic agonist may be an amount ranging from about 10-1000 mg (e.g., about 20 mg-1,000 mg, 30 mg-1,000 mg, 40 mg-1,000 mg, 50 mg-1,000 mg, 60 mg-1,000 mg, 70 mg-1,000 mg, 80 mg-1,000 mg, 90 mg-1,000 mg, about 10-900 mg, 10-800 mg, 10-700 mg, 10-600 mg, 10-500 mg, 100-1000 mg, 100-900 mg, 100-800 mg, 100-700 mg, 100-600 mg, 100-500 mg, 100-400 mg, 100-300 mg, 200-1000 mg, 200-900 mg, 200-800 mg, 200-700 mg, 200-600 mg, 200-500 mg, 200-400 mg, 300-1000 mg, 300-900 mg, 300-800 mg, 300-700 mg, 300-600 mg, 300-500 mg, 400 mg-1,000 mg, 500 mg-1,000 mg, 100 mg-900 mg, 200 mg-800 mg, 300 mg-700 mg, 400 mg-700 mg, and 500 mg-600 mg). In some embodiments, the 15-PGDH inhibitor is present in an amount of or greater than about 10 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg. In some embodiments, the 15-PGDH inhibitor is present in an amount of or less than about 1000 mg, 950 mg, 900 mg, 850 mg, 800 mg, 750 mg, 700 mg, 650 mg, 600 mg, 550 mg, 500 mg, 450 mg, 400 mg, 350 mg, 300 mg, 250 mg, 200 mg, 150 mg, or 100 mg.

In other embodiments, a therapeutically effective dosage amount of the GP130 receptor signaling activator, the Wnt signaling activator, cholinergic agonist, muscarinic agonist, and/or nicotinic agonist may be, for example, about 0.001 mg/kg weight to 500 mg/kg weight, e.g., from about 0.001 mg/kg weight to 400 mg/kg weight, from about 0.001 mg/kg weight to 300 mg/kg weight, from about 0.001 mg/kg weight to 200 mg/kg weight, from about 0.001 mg/kg weight to 100 mg/kg weight, from about 0.001 mg/kg weight to 90 mg/kg weight, from about 0.001 mg/kg weight to 80 mg/kg weight, from about 0.001 mg/kg weight to 70 mg/kg weight, from about 0.001 mg/kg weight to 60 mg/kg weight, from about 0.001 mg/kg weight to 50 mg/kg weight, from about 0.001 mg/kg weight to 40 mg/kg weight, from about 0.001 mg/kg weight to 30 mg/kg weight, from about 0.001 mg/kg weight to 25 mg/kg weight, from about 0.001 mg/kg weight to 20 mg/kg weight, from about 0.001 mg/kg weight to 15 mg/kg weight, from about 0.001 mg/kg weight to 10 mg/kg weight.

In still other embodiments, a therapeutically effective dosage amount of the GP130 receptor signaling activator, the Wnt signaling activator, cholinergic agonist, muscarinic agonist, and/or nicotinic agonist may be, for example, about 0.0001 mg/kg weight to 0.1 mg/kg weight, e.g. from about 0.0001 mg/kg weight to 0.09 mg/kg weight, from about 0.0001 mg/kg weight to 0.08 mg/kg weight, from about 0.0001 mg/kg weight to 0.07 mg/kg weight, from about 0.0001 mg/kg weight to 0.06 mg/kg weight, from about 0.0001 mg/kg weight to 0.05 mg/kg weight, from about 0.0001 mg/kg weight to about 0.04 mg/kg weight, from about 0.0001 mg/kg weight to 0.03 mg/kg weight, from about 0.0001 mg/kg weight to 0.02 mg/kg weight, from about 0.0001 mg/kg weight to 0.019 mg/kg weight, from about 0.0001 mg/kg weight to 0.018 mg/kg weight, from about 0.0001 mg/kg weight to 0.017 mg/kg weight, from about 0.0001 mg/kg weight to 0.016 mg/kg weight, from about 0.0001 mg/kg weight to 0.015 mg/kg weight, from about 0.0001 mg/kg weight to 0.014 mg/kg weight, from about 0.0001 mg/kg weight to 0.013 mg/kg weight, from about 0.0001 mg/kg weight to 0.012 mg/kg weight, from about 0.0001 mg/kg weight to 0.011 mg/kg weight, from about 0.0001 mg/kg weight to 0.01 mg/kg weight, from about 0.0001 mg/kg weight to 0.009 mg/kg weight, from about 0.0001 mg/kg weight to 0.008 mg/kg weight, from about 0.0001 mg/kg weight to 0.007 mg/kg weight, from about 0.0001 mg/kg weight to 0.006 mg/kg weight, from about 0.0001 mg/kg weight to 0.005 mg/kg weight, from about 0.0001 mg/kg weight to 0.004 mg/kg weight, from about 0.0001 mg/kg weight to 0.003 mg/kg weight, from about 0.0001 mg/kg weight to 0.002 mg/kg weight. In some embodiments, the therapeutically effective dose may be 0.0001 mg/kg weight, 0.0002 mg/kg weight, 0.0003 mg/kg weight, 0.0004 mg/kg weight, 0.0005 mg/kg weight, 0.0006 mg/kg weight, 0.0007 mg/kg weight, 0.0008 mg/kg weight, 0.0009 mg/kg weight, 0.001 mg/kg weight, 0.002 mg/kg weight, 0.003 mg/kg weight, 0.004 mg/kg weight, 0.005 mg/kg weight, 0.006 mg/kg weight, 0.007 mg/kg weight, 0.008 mg/kg weight, 0.009 mg/kg weight, 0.01 mg/kg weight, 0.02 mg/kg weight, 0.03 mg/kg weight, 0.04 mg/kg weight, 0.05 mg/kg weight, 0.06 mg/kg weight, 0.07 mg/kg weight, 0.08 mg/kg weight, 0.09 mg/kg weight, or 0.1 mg/kg weight. The effective dose for a particular individual can be varied (e.g., increased or decreased) over time, depending on the needs of the individual.

In some embodiments, a therapeutically effective dosage of the GP130 receptor signaling activator, the Wnt signaling activator, cholinergic agonist, muscarinic agonist, and/or nicotinic agonist may be a dosage of 10 µg/kg/day, 50 µg/kg/day, 100 µg/kg/day, 250 µg/kg/day, 500 µg/kg/day, 1000 µg/kg/day or more. In various embodiments, the amount of the GP130 receptor signaling activator, the Wnt signaling activator, cholinergic agonist, muscarinic agonist, and/or nicotinic agonist is sufficient to provide a dosage to a patient of between 0.01 µg/kg and 10 µg/kg; 0.1 µg/kg and 5 µg/kg; 0.1 µg/kg and 1000 µg/kg; 0.1 µg/kg and 900 µg/kg; 0.1 µg/kg and 900 µg/kg; 0.1 µg/kg and 800 µg/kg; 0.1 µg/kg and 700 µg/kg; 0.1 µg/kg and 600 µg/kg; 0.1 µg/kg and 500 µg/kg; or 0.1 µg/kg and 400 µg/kg.

Various embodiments may include differing dosing regimens. In some embodiments, the GP130 receptor signaling activator, the Wnt signaling activator, cholinergic agonist, muscarinic agonist, and/or nicotinic agonist can be administered bimonthly, monthly, twice monthly, triweekly, biweekly, weekly, twice weekly, thrice weekly, daily, twice daily, or on another clinically desirable dosing schedule. The dosing regimen for a single subject need not be at a fixed interval, but can be varied over time, depending on the needs of the subject.

For use in treating animal subjects, compositions including the agents described herein can be formulated as pharmaceutical or veterinary compositions. Depending on the subject to be treated, the mode of administration, and the type of treatment desired, e.g., prevention, prophylaxis, therapy; the compositions are formulated in ways consonant with these parameters. A summary of such techniques is found in Remington's Pharmaceutical Sciences, latest edition, Mack Publishing Co., Easton, Pa.

The preparation of therapeutic compositions containing small organic molecules polypeptides, analogs or active fragments as active ingredients is well understood in the art. The compositions of the present invention may be administered parenterally, topically, or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Formulations may be prepared in a manner suitable for systemic administration or for topical or local administration. Systemic formulations include, but are not limited to those designed for injection (e.g., intramuscular, intravenous or subcutaneous injection) or may be prepared for transdermal, transmucosal, nasal, or oral administration. Such compositions may be prepared as injectables, either as liquid solutions or suspensions, however, solid forms suitable for solution in, or suspension in, liquid prior to injection can also be prepared. The preparation can also be emulsified. The active therapeutic ingredient is often mixed with excipients, which are pharmaceutically acceptable and compatible with the active ingredient. Suitable excipients are, for example, water, saline, dextrose, glycerol, ethanol, or the like and combinations thereof. The formulation will generally include a diluent as well as, in some cases, adjuvants, buffers, preservatives and the like. In addition, if desired, the composition can contain minor amounts of auxiliary substances such as wetting or emulsifying agents, pH buffering agents, which enhance the effectiveness of the active ingredient.

The compositions may also be administered locally to sites in subjects using a variety of techniques known to those skilled in the art. For example, these may include sprays, lotions, gels or other vehicles, such as alcohols, polyglycols, esters, oils and silicones. The administration of the compositions described herein may be pharmacokinetically and pharmacodynamically controlled by calibrating various parameters of administration, including the frequency, dosage, duration mode and route of administration. Variations in the dosage, duration and mode of administration may also be manipulated to produce the activity required. The therapeutic compositions are conventionally administered in the form of a unit dose, for instance intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions can be administered in a manner compatible with the agent selected for treating the subject, the dosage formulation, and in a therapeutically effective amount. If one desires to achieve the desired effect in vitro, the effective amounts may range from about 0.1 nM to about 10 M, more preferably about 0.1 nM to about 5 M, and most preferably from about 0.1 nM to about 1 M. The desired effect refers to the effect of the agent on inducing chondrocyte differentiation, inhibiting chondrocyte differentiation, and/or treating the bone injury. Precise amounts of active ingredient required to be administered depend on the judgment of the practitioner and are peculiar to each individual.

It will be understood that the appropriate dosage of the agent should suitably be assessed by performing animal model tests, where the effective dose level (e.g., $ED_{50}$) and the toxic dose level (e.g., $TD_{50}$) as well as the lethal dose level (e.g., $LD_{50}$ or $LD_{10}$) are established in suitable and acceptable animal models. Further, if a substance has proven efficient in such animal tests, controlled clinical trials should be performed.

The agents described herein may be modified or formulated for administration at the site of pathology. Such modification may include, for instance, formulations, which facilitate or prolong the half-life of the compound or composition, particularly in the environment. Additionally, such modification may include the formulation of a compound or composition to include a targeting protein or sequence, which facilitates or enhances the uptake of the compound/composition to bone or bone precursor cells. In a particular embodiment, such modification results in the preferential targeting of the compound to bone or bone precursor cells versus other locations or cells.

Sterile injectable forms of the compositions may be aqueous or oleaginous suspensions. The suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents, which are commonly, used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Parenteral formulations may be a single bolus dose, an infusion or a loading bolus dose followed with a maintenance dose. These compositions may be administered once a day or on an "as needed" basis. The pharmaceutical compositions may be orally administered in any orally acceptable dosage form including, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added. Alternatively, the pharmaceutical compositions may be administered in the form of suppositories for rectal administration. These can be prepared by mixing the agent with a suitable non-irritating excipient, which is solid at room temperature but liquid at rectal temperature and therefore will melt in the rectum to release the drug. Such materials include cocoa butter, beeswax and polyethylene glycols. The pharmaceutical compositions of this invention may also be administered topically. Topical application can be effected in a rectal suppository formulation (see above) or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of this invention include, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

In some embodiments, the GP130 receptor signaling activator, the Wnt signaling activator, cholinergic agonist, muscarinic agonist, and/or nicotinic agonist can be formulated to provide controlled release of the GP130 receptor signaling activator, the Wnt signaling activator, cholinergic agonist, muscarinic agonist, and/or nicotinic agonist to the osteochondrogenic cells. The controlled release can include at least one of a delayed, sustained, gradient, temporal, patterned, or spatial release. Delayed, sustained, gradient, temporal, patterned, or spatial release is a mechanism used in medicine to allow release to the active ingredient over time. The advantages of controlled release formulations are that they delivered less frequently and in defined release patterns than immediate-release formulations of the same active compound.

A controlled release formulation can be designed to release the active agents at a predetermined rate so as to maintain a constant agent level for a specified, extended period of time, such as up to about 1 hour, about 12 hours, about 24 hours, about 2 days, about 3 days, about 1 week or more following administration or following a lag period associated with delayed-release of the agent.

In certain preferred embodiments, the active agents are released over a time interval of between about 1 hour to about 1 week or more. Alternatively, the active agents may be released over about 1 hour, about 12 hours, about 24 hours, about 2 days, about 3 days, 1 week or more. In yet other embodiments, the active agents are released over a time period between about 1 hour to about 1 week or more following administration.

In some embodiments, the GP130 receptor signaling activator can administered to the chondrocytes prior to administration of the Wnt signaling activator, cholinergic agonist, muscarinic agonist, and/or nicotinic agonist and/or concurrently with the Wnt signaling activator, cholinergic agonist, muscarinic agonist, and/or nicotinic agonist. In other embodiments, the GP130 receptor signaling activator can administered in conjunction with cholinergic agonist, muscarinic agonist, and/or nicotinic agonist and without Wnt signaling activator. In still other embodiments, the cholinergic agonist, muscarinic agonist, and/or nicotinic agonist can be administered to chondrocytes after upregulation or enhanced expression of nerve growth factor receptors and/or cholinergic, muscarinic, and/or nicotinic receptors.

In some embodiments, the GP130 receptor signaling activator can administered to a site of the bone fracture, bone disease, bone injury, or bone abnormality prior to administration of the Wnt signaling activator, cholinergic agonist, muscarinic agonist, and/or nicotinic agonist and/or concurrently with the Wnt signaling activator, cholinergic agonist, muscarinic agonist, and/or nicotinic agonist. In other embodiments, the GP130 receptor signaling activator can administered in conjunction with cholinergic agonist, muscarinic agonist, and/or nicotinic agonist and without Wnt signaling activator to a site of the bone fracture, bone disease, bone injury, or bone abnormality. In still other embodiments, cholinergic agonist, muscarinic agonist, and/or nicotinic agonist can be administered to chondrocytes after upregulation or enhance expression of nerve growth factor receptors and/or cholinergic, muscarinic, and/or nicotinic receptor, for example, from about days 4 to about days 12, or about days 4 to about days 10, post-fracture or injury.

In other embodiments, the GP130 receptor signaling activator, the Wnt signaling activator, cholinergic agonist, muscarinic agonist, and/or nicotinic agonist can be provided in a carrier, matrix, or scaffold material to provided controlled release of the active agent to the chondrocytes.

The carrier, matrix or scaffold may be of any material that will allow the GP130 receptor signaling activator, the Wnt signaling activator, cholinergic agonist, muscarinic agonist, and/or nicotinic agonist to be incorporated and will be compatible with the addition of cells or in the presence of cells. Preferably, the carrier matrix or scaffold is predominantly non-immunogenic and is biodegradable. Examples of biodegradable materials include, but are not limited to, polyglycolic acid (PGA), polylactic acid (PLA), hyaluronic acid, catgut suture material, gelatin, cellulose, nitrocellulose, collagen, albumin, fibrin, alginate, cotton, or other naturally occurring biodegradable materials. It may be preferable to sterilize the matrix or scaffold material prior to administration or implantation, e.g., by treating it with ethylene oxide or by gamma irradiation or irradiation with an electron beam. In addition, a number of other materials may be used to form the scaffold or framework structure, including but not limited to: nylon (polyamides), dacron (polyesters), polystyrene, polypropylene, polyacrylates, polyvinyl compounds (e.g., polyvinylchloride), polycarbonate (PVC), polytetrafluorethylene (PTFE, teflon), thermanox (TPX), polymers of hydroxy acids such as polylactic acid (PLA), polyglycolic acid (PGA), and polylactic acid-glycolic acid (PLGA), polyorthoesters, polyanhydrides, polyphosphazenes, and a variety of polyhydroxyalkanoates, and combinations thereof.

Matrices suitable include a polymeric mesh or sponge and a polymeric hydrogel. A hydrogel is defined as a substance formed when an organic polymer (natural or synthetic) is cross-linked via covalent, ionic, or hydrogen bonds to create a three-dimensional open-lattice structure, which entraps water molecules to form a gel. In general, these polymers are at least partially soluble in aqueous solutions, such as water, buffered salt solutions, or aqueous alcohol solutions that have charged side groups, or a monovalent ionic salt thereof.

In the some embodiments, the matrix is biodegradable over a time period of less than a year, more preferably less than six months, most preferably over two to ten weeks. The polymer composition, as well as method of manufacture, can be used to determine the rate of degradation. For example, mixing increasing amounts of polylactic acid with polyglycolic acid decreases the degradation time. Meshes of polyglycolic acid that can be used can be obtained commercially, for instance, from surgical supply companies (e.g., Ethicon, N.J.).

Still other embodiments relate to a composition for treatment of a tissue injury. The composition includes a carrier material that includes a polymeric macro- or micro-scaffold and/or a plurality of biocompatible and biodegradable nanoparticles and/or microparticle. At least one bioactive agent is provided on or in the polymeric macro- or micro-scaffold and/or a plurality of biocompatible and biodegradable nanoparticles and/or microparticles. The bioactive agent includes at least one, two, three or more of: (i) an agent activates GP130 receptor signaling (GP130 receptor signaling activator) to induce transdifferentiation of chondrocytes to osteoblasts; (ii) an agent that activates canonical Wnt signaling (Wnt signaling activator) in the chondrocytes; or (iii) at least one of a cholinergic agonist, muscarinic agonist, or nicotinic agonist. Optionally, the composition includes osteochondrogenic cells.

In some embodiments, the GP130 receptor signaling activator induces a pluripotency like state that primes the chondrocytes for differentiation to osteoblasts. The GP130 receptor signaling activator can include at least one of leukemia inhibitory factor (LIF), an LIF receptor agonist, a GP130 receptor agonist, or interleukin-6 cytokine.

In other embodiments, the Wnt signaling activator can promote differentiation of the chondrocytes to osteoblasts. The Wnt signaling activator can include at least one of a Wnt ligand or agonist or an inhibitor of a negative regulator of Wnt signaling. For example, the Wnt ligand or agonist can include at least one of a frizzled receptor agonist, Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, Wnt16, Norrin ligand, or R-spondin2.

The inhibitor of a negative regulator of Wnt signaling can include at least one of a glycogen synthase kinase 3 (GSK-3)

inhibitor, a PKA inhibitor, a PKC inhibitor, a MEK1/2 inhibitor, a MAPK inhibitor, a JNK inhibitor, a DKK inhibitor, or a sclerostin inhibitor.

The cholinergic agonist can include at least one of acetylcholine or an acetylcholine analogue, such as carbachol.

Other embodiments described herein relate to the inhibition of transdifferentiation of chondrocytes to osteoblasts by administration to the chondrocytes an agent that inhibits GP130 receptor signaling to inhibit transdifferentiation of the chondrocytes to osteoblasts. The agent can include, for example, at least one of a LIF antagonist, a LIF receptor antagonist, a GP130 receptor antagonist, or an IL-6 antagonist. For example, the agent can include at least one of an IL-6R antibody or IL-27p28.

In some embodiments, the agent that inhibits GP130 receptor signaling to inhibit transdifferentiation of the chondrocytes can be administered to a subject having or at risk of heterotopic ossification.

In other embodiments, the agent that inhibits GP130 receptor signaling to inhibit transdifferentiation of the chondrocytes can be administered to a subject having, during, or following a traumatic injury or surgery.

EXAMPLE 1

In this Example, we examined the cellular and molecular properties of the cells located at the chondro-osseous junction of the fracture callus to understand the mechanism(s) by which chondrocytes become osteoblasts during fracture healing.
Materials and Methods
Fractures Adult (10-14 weeks) male mice were anesthetized, and closed non-stable fractures were made mid-diaphysis of the tibia via three-point bending. Fractures were not stabilized to promote robust endochondral repair. Animals were provided with post-operative analgesics and allowed to ambulate freely.

For lineage tracing, induction of Cre recombination was achieved by intraperitoneal administration of tamoxifen (75 mg tamoxifen/kg), daily from days 6-10 post-fracture. For Sox2 knockout, tamoxifen was administered on days 4-7, 10 and 12. Tibiae (n≥5) were harvested 14 days post-fracture for analysis.
Bone Tissue Embedding and Histology Fractured tibiae were fixed in 4% paraformaldehyde (PFA, pH 7.2-7.4) for 24 h, then decalcified in 19% EDTA (pH 7.4) for 14 days at 4° C. Unless otherwise noted, mice were processed for paraffin histology. Tissues from mice crossed to R26R or Ai9 reporter strains were embedded in OCT and sectioned using a cryostat. Serial sections were cut at 8-10 μm for histological and immunohistochemical analysis or 3-5 μm for cell tracing analysis. Standard histological protocols to visualize bone and cartilage were used: Modified Milligan's Trichrome (bone stains blue), Safranin O/Fast Green (cartilage stains red) or Hall and Brunt Quadruple stain (HBQ, bone stains red, cartilage stains blue).
Immunohistochemistry on Fracture Callus In R26R transgenic tissues, detection of β-galactosidase activity was performed on frozen sections post-fixed in 0.2% glutaraldehyde for 15 min and then exposed to X-gal staining solution with 50 mg/ml 5-Bromo-4-chloro-3-indolyl β-D-galactoside (Sigma, B4252) overnight at 37° C. Immunohistochemistry (IHC) was performed on paraffin sections from fractured tibiae of wild-type mice (>12 mice per antibody) 10 days postfracture unless otherwise indicated. The basic protocol included antigen retrieval in 10 mM sodium citrate buffer (20 min, 100° C.), endogenous peroxidase blocking in 3% $H_2O_2$ in phosphate buffered saline (PBS) (30 min) and non-specific epitope blocking with 5% bovine serum albumin (BSA, 1 h). Primary antibodies were applied to the sections overnight at 4° C. (full antibody). Species-specific secondary antibodies (1:500 in PBS with 1% BSA for 1 h at room temperature) were detected using the VectaStain ABC Kit (Vector, PK-4000) and 3,3'-diaminobenzidine (DAB) colorimetric reaction, or by immunofluorescence using species-specific Alexa-Fluor-488 or -594 secondary antibodies.
In Situ Hybridization In situ hybridization was performed on paraffin wax embedded sections as previously described (Hu and Marcucio, 2009; Rumballe et al., 2008). Subclones of mouse collagen II (Col2a1), collagen X (Col10a1), collagen I (Col1a1) and osteopontin (Opn) were linearized for transcription of DIG-labeled anti-sense riboprobes.
Cell Proliferation Detection Bromodeoxyurindine (BrdU, 5 mg) was diluted in PBS and delivered by an intraperitoneal injection 2 h prior to euthanasia. Positive cells were detected by an anti-BrdU staining kit (Invitrogen, 93-3943). To quantify BrdU+ cells, a central section representative of the largest cross-section of the fracture callus of 4 mice, was evaluated using an Olympus CAST system and software by Visiopharm. Tissues of interest (C, HC, TZ, NB) were outlined using low magnification (20×), and cell counting was performed under high magnification (200×) using a count frame probe that covered 50% of the area within a field of view. Following stereology counting frame rules, a minimum of 200 cells for each tissue were acquired using uniform random sampling. The percentage of BrdU+ versus BrdU− cells was estimated by applying the fractionator method (Howard and Reed, 1998). Graphs represent mean±s.d. from four biological replicates. Statistical analysis was completed using JMP v.12.1.0 software to perform an ANOVA followed by a post hoc comparison of all pairs using Tukey—Kramer HSD, $P<0.05$ was considered significant (*$P<0.05$, $P<0.005$, *$P<0.0005$).
Tunel The Roche In Situ Cell Death Detection Kit (Roach, 116847959) was used according to the manufactures protocol. Sections were deparaffinized, treated with proteinase K (20 μg/ml in 10 mM Tris-HCl, pH 8, 15 min), and then reacted with the kit for 1 h at 37° C. in the dark. Positive controls were treated with DNase I prior to TUNEL reaction, while negative controls were not treated with the TUNEL reaction mixture. Slides were mounted in VectaShield with DAPI (Vector, H-1200) and visualized using an epifluorescence microscope.
In Vitro Cartilage Explant Culture Cartilage explants were isolated from the central portion of the day 7 fracture callus using a dissecting microscope to remove any adherent noncartilaginous tissues and the perichondrium. This method reliably yields tissue that is highly cartilaginous, with no evidence of bone or stem cell markers. Explants were grown in vitro for1 week in serum-free chondrogenic medium to promote hypertrophic maturation [high glucose DMEM, 1% penicillin-streptomycin, 1% ITS+ Premix (BD Biosciences Cat #354352), 1 mM sodium pyruvate, 100 ng/ml ascorbate-2-phosphate and 10-7 M dexamethasone]. Explants were kept in chondrogenic medium, or transferred into either osteogenic medium or a human vascular endothelial cell conditioned medium (HUVEC-CM) for an additional week. Osteogenic medium is chondrogenic medium plus 10 nM bone morphogenetic protein 2 (BMP2) and 10 mM β-glycerol phosphate. HUVEC-CM was collected from confluent plates of early passage HUVEC cells, without addition of growth factors (Bahney et al., 2014).

Transfection of Pluripotent Genes

An OCT4-SOX2 specific construct was generated from the commercially available pEP4-E02S-EN2L (Addgene, 20922) by excising NANOG and LIN28 with BamHI. These genes were transfected into the fracture callus cartilage explants ex vivo using Lipofectamine2000 reagent (Thermo Fisher, 11668019). Cartilage was dissected from the day 7 fracture callus of 10 mice as described above, combined, and then finely minced into small pieces. After 24 h in chondrogenic medium, fracture callus explants were transfected with 0.8 μg plasma DNA using 2 μl lipofectamine in 100 μl Opti-MEM medium for 6 h at 37° C. The explants receiving OCT4-SOX2 genes were then transferred back to chondrogenic medium and compared with constructs that remained in chondrogenic medium as a control, or those cultured in osteogenic medium. Cartilage was then harvested 48 h later for mRNA isolation.

Stereology

Quantification of graft composition (cartilage, bone, fibrous, marrow space) was determined using an Olympus CAST system (Center Valley, Pa.) and software by Visiopharm (Hørsholm, Denmark) according to established methodologies. For quantification of the bone and cartilage, 10 μm serial sections, three sections per slide, were taken through the entire leg. Tissue was stained with Safranin-O as described above, and the first section from every 10th slide analyzed such that sections were 300 μm apart. The fracture callus was outlined using low magnification (2×), then tissue composition was quantified in 15% of fracture callus using automated uniform random sampling to meet or exceeds the basic principles of stereology. Cell identity within each random sampling domain was determined at high magnification (20×) according to histological staining patterns and cell morphology. Volume of the specific tissue type (e.g., bone or cartilage composition) was determined in reference to the total fracture callus volume by summing the individual compositions relative to the whole. Marrow space was considered as tissue that fell within a blood vessel or marrow cavity of the new bone. Graphs plot mean±95% confidence interval; JMP software tested for significance using the non-parametric Wilcoxon/Kruskal—Wallis Test ($*P<0.05$).

mRNA Isolation and Quantitative RT-PCR mRNA was isolated from cartilage grafts in 100 μl Trizol. cDNA was reverse transcribed with Superscript III (Invitrogen, 18080), and quantitative RTPCR was performed using SYBR Green and primers. Relative gene expression was calculated by normalizing to GAPDH (ΔCT), then to explants cultured under chondrogenic conditions (ΔΔCT). Fold change was calculated as 2-ΔΔCT. Graphs represent mean±95% confidence interval of biological replicates for the cartilage grafts (n=5). Significance was determined using an ANOVA followed by a post hoc multiple comparison using Tukey-Kramer HSD. ($*P<0.05$, $P<0.005$, $*P<0.0005$).

Results

Mature hypertrophic chondrocytes in the fracture callus express canonical bone markers. We created closed midshaft tibia fractures that remained unstabilized to generate a robust endochondral healing response. In previous studies using this model we detailed the sequence of endochondral repair as follows; cartilage condensation (days 3-5), maturation and mineralization of the cartilage (days 5-14), trabecular bone formation (days 10-14), bone remodeling (day 14+). We focus on the transformation of cartilage into bone during days 7 to 14 of fracture healing. We focus on a specific histological region, the 'transition zone' (TZ), which represents the chondro-osseous junction in the fracture callus. This region can be visualized in the day 10 fracture callus using standard histological staining to distinguish cartilage and bone (FIG. 1). Importantly, histology shows that the transitional phenotype occurs around the invading blood vessels (FIG. 1G-I). Here, proteoglycans are lost from matrix surrounding the hypertrophic chondrocytes and these cells start producing a bone matrix (FIG. 1G-I, white arrows).

Figure 2:
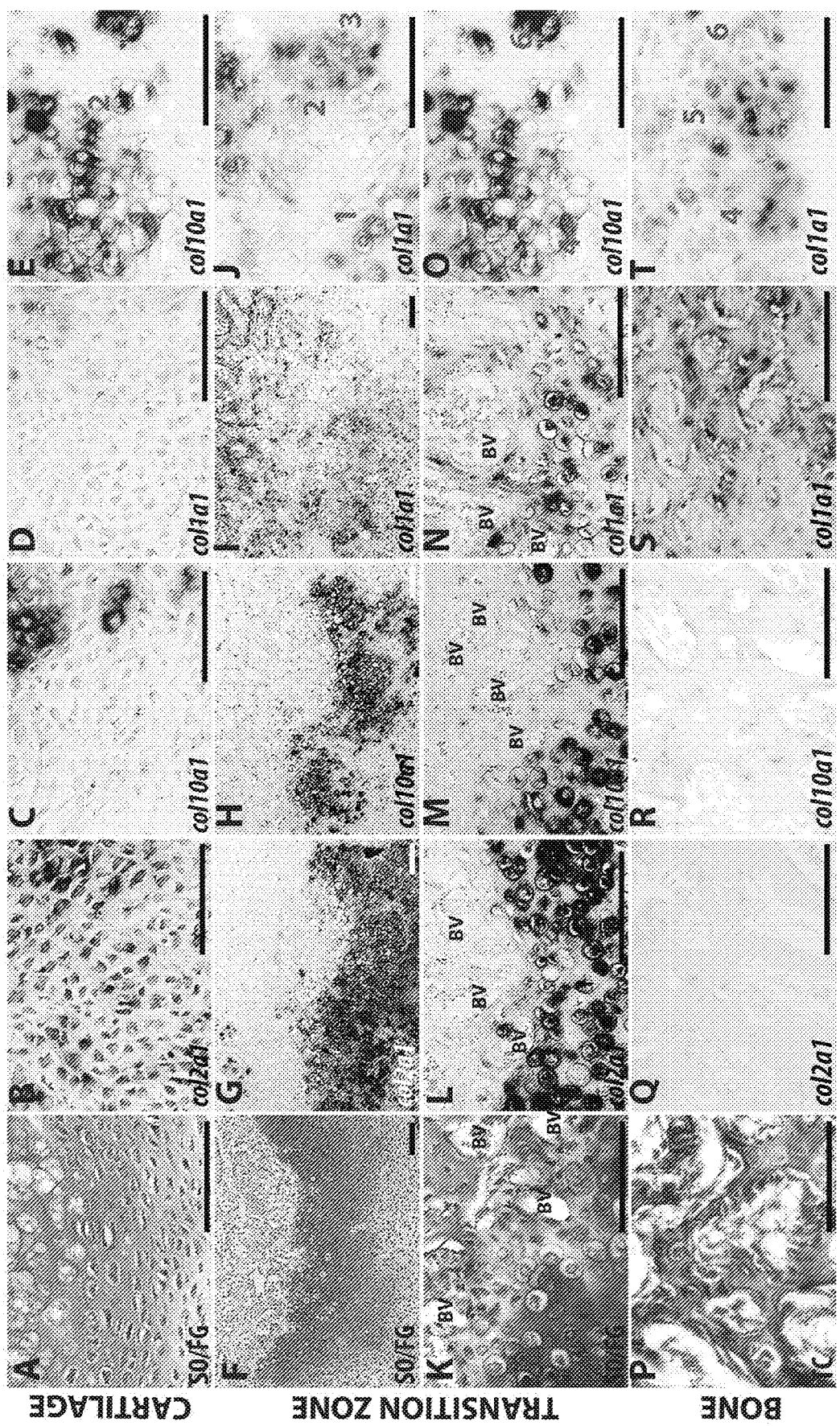
FIGS. 2(A-T) illustrate images showing the maturation of cartilage in the transition zone. Chondrocytes away from the TZ (A-D), compared with hypertrophic chondrocytes (HCs) in the TZ of murine fracture callus (E-O,T) or newly formed bone (P-S). Left column shows cartilage and bone histology stained with either SO/FG (A,F,K) or TC (P). In situ hybridization with Col2a1 (B,G,L,Q), Col10a1 (C,H,M,R) or Col1a1 (D,I,N,S). (E,J,O,T) Col10a1 and Col1a1 staining on adjacent sections 3-5 μm apart. Individual cells were tracked (cells 1-6) to demonstrate that staining does not overlap. Scale bars: 100 μm.
Figure 3:
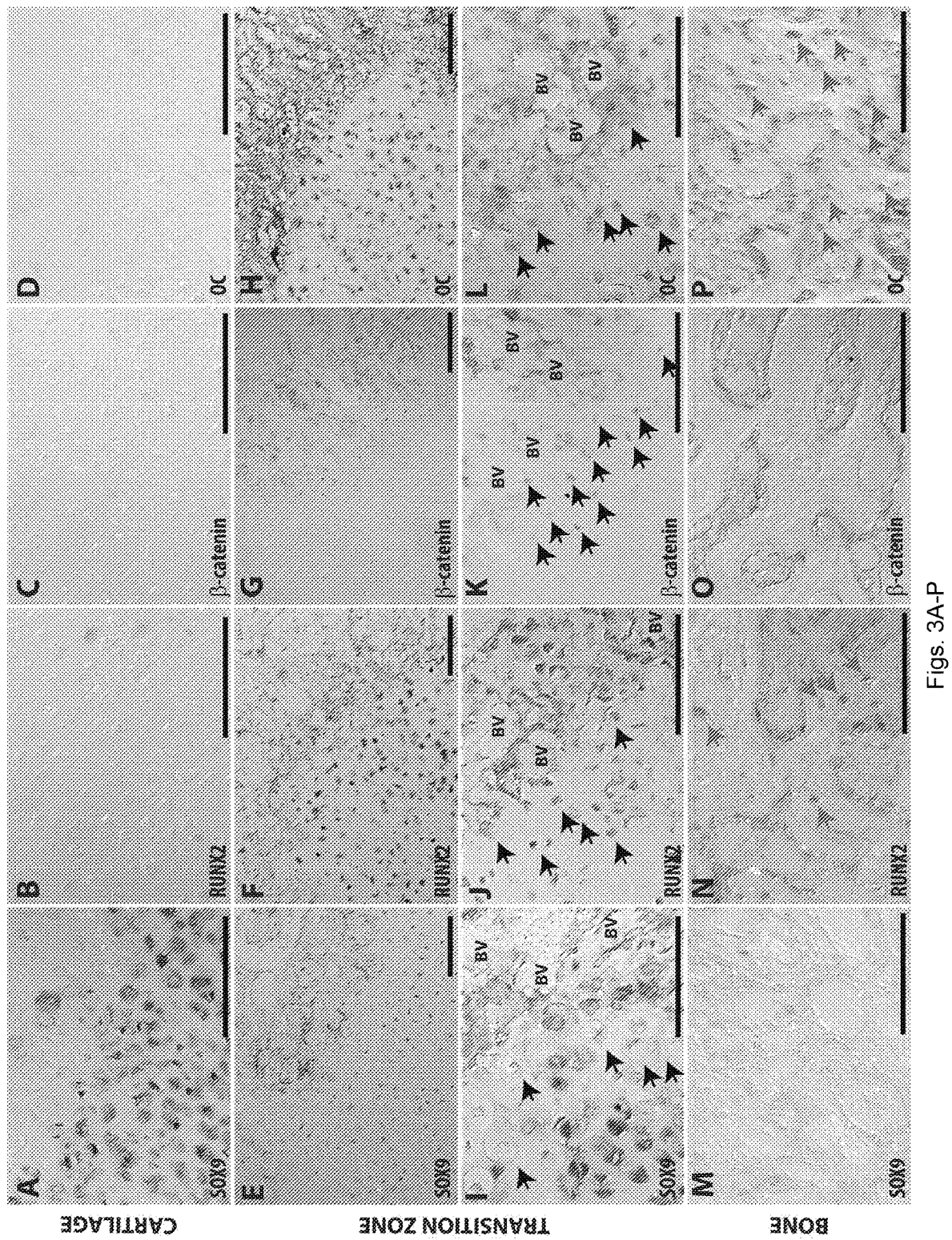
FIGS. 3(A-P) illustrate images showing hypertrophic chondrocytes adjacent to vasculature in the transition zone lose their chondrocyte phenotype and acquire an osteoblast phenotype. Immunohistochemistry in the cartilage away from the TZ (A-D), compared with HCs in the TZ (E-L) or new bone (NB) (M-P). (I-L) Black arrows indicate HCs in TZ that are Sox9 negative (I), and positive for Runx2 (J), β-catenin (K) or Oc (L). (M-P) Red arrows in NB tissue indicate Runx2+ (N) and Oc+ (P) cells. Scale bars: 100 μm.

To provide a detailed characterization of the cellular phenotype in the TZ, we analyzed the spatial expression of the canonical markers of chondrocytes and osteoblasts (FIGS. 2 and 3). The cartilaginous region of the fracture callus was observed after Safranin-O staining (FIG. 2A) along with expression of the canonical chondrocyte markers collagen II (Col2a1; FIG. 2B) and Sox9 (FIG. 3A). As the chondrocytes mature, the cells enlarge to a hypertrophic state (FIG. 2A,K) and express collagen X (Col10a1; FIG. 2H,M). In the TZ, chondrocytes lose chondrogenic signatures (Sox9, Col2a1, Col10a1) and begin expressing bone-specific collagen I (Col1a1) despite maintaining a hypertrophic morphology (FIG. 2L-N, FIG. 3A,E). Through the use of thin (3-5 μm) adjacent sections, we tracked individual cells to demonstrate that expression of Col10a1 and Col11a1 are mutually exclusive (FIG. 2E,J,O,T).

Transcriptional regulation of these 'hypertrophic osteoblasts' has switched from chondrogenic programming (loss of Sox9: FIG. 3I), to osteogenic (appearance of Runx2: FIG. 3J). Expression of Runx2 correlates with nuclear localization of β-catenin, indicating activation of canonical Wnt signaling in hypertrophic chondrocytes in the TZ adjacent to the vasculature (FIG. 3C,G,K). Runx2 and Wnt are required for osteogenesis.

Downstream canonical bone programs—osteocalcin (Oc, also known as BGLAP), osteopontin [Opn (Sppl)] and osterix [Osx (Sp7)]—also appear in these cells that would morphologically be identified as hypertrophic chondrocytes (FIG. 3). Away from the TZ, osteocalcin expression begins as intracellular staining (FIG. 3H), with protein accumulating in the matrix around hypertrophic cells within the TZ adjacent to the vasculature and in the newly formed bone (FIG. 3H,L). Similarly, as shown by in situ hybridization, expression of Opn is initially absent from the immature cartilage but becomes robustly expressed in hypertrophic cells adjacent to the vasculature. Lastly, we evaluate Osx expression using an Osterix(Sp7)-CreERT mouse crossed to the R26R reporter line. For all lineage-tracing experiments, animals were allowed to heal without intervention for 6 days, at which point there is a robust cartilage callus. Recombination is induced from days 6 to 10 by daily intraperitoneal tamoxifen injections and fractured legs harvested at day 14 for analysis. Osx is expressed in the hypertrophic chondrocytes in the TZ in areas around the vasculature, in the osteoblasts and osteocytes of the new bone, and in the bone lining cells of the newly formed trabeculae.

Hypertrophic Chondrocytes Re-Enter the Cell Cycle or Undergo Apoptosis

Figure 4:
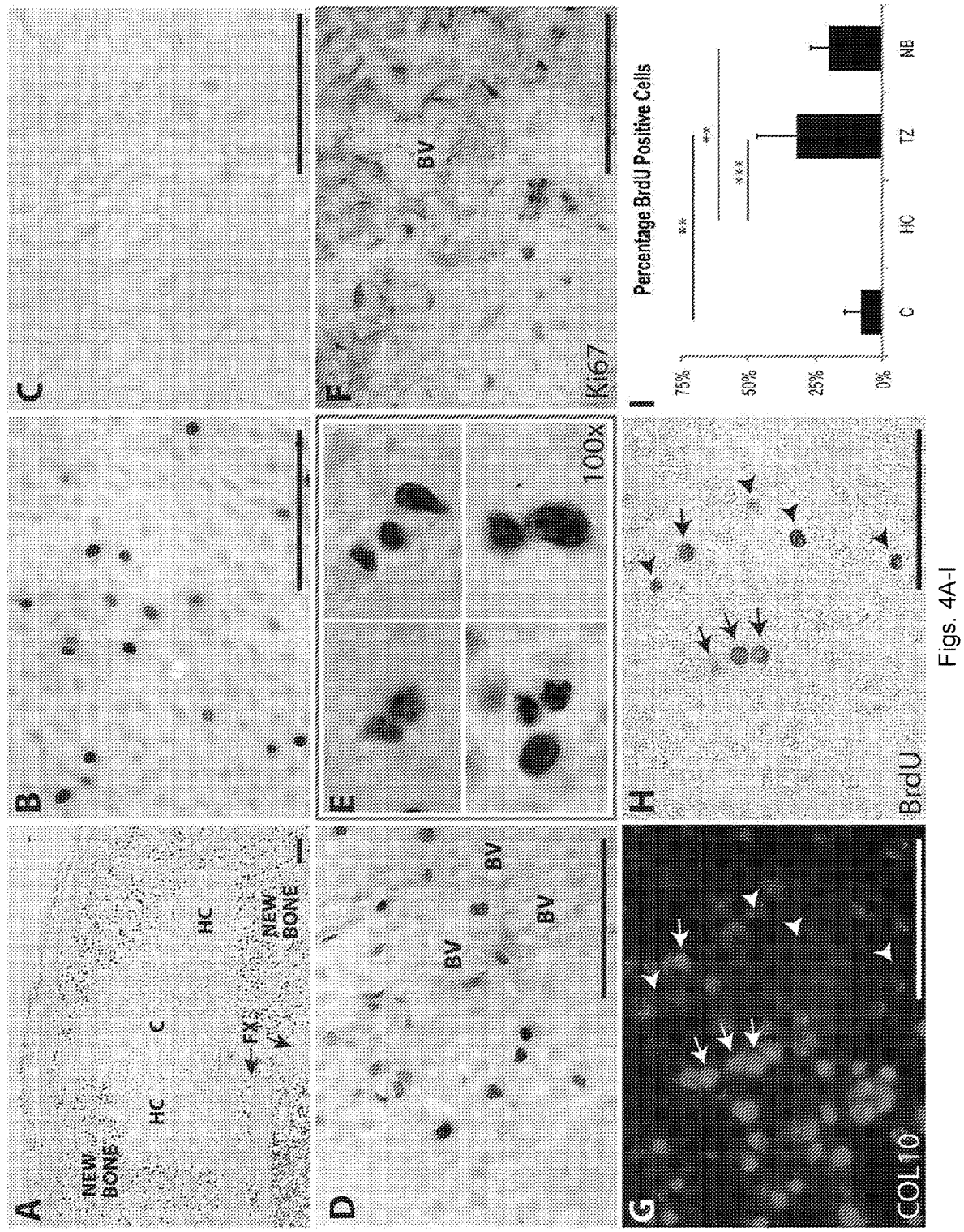
FIGS. 4(A-I) illustrate images and a graph showing hypertrophic chondrocytes adjacent to vasculature in the transition zone re-enter the cell cycle. BrdU detection for entire fracture callus (A), immature chondrocytes away from the TZ (B), HCs away from the TZ (C), HCs in the TZ (D,E). (F,G) Ki67 and collagen X immunohistochemistry in HCs at the TZ. (H) Collagen X is observed to overlap with some of the BrdU+ cells (arrows), but not all (arrowheads). (I) Quantification of BrdU+/BrdU− cells in fracture callus. Scale bars: 100 μm.

Hypertrophic chondrocytes have traditionally been considered as a terminally differentiated, post-mitotic cell. To visualize the pattern of cell division during endochondral fracture repair, we administered BrdU 2 hours prior to the harvest of tibiae 14 days after fracture (FIG. 4). Proliferation occurs in immature chondrocytes in the central portion of the fracture, suggesting that these cells are responsible for expansion of the cartilage callus (FIG. 4B). Consistent with the dogma that hypertrophic chondrocytes are postmitotic, no cell division is observed in the hypertrophic chondrocyte away from the TZ (FIG. 4C). However, hypertrophic cells directly adjacent to the vasculature incorporate BrdU, indicating that they reenter the cell cycle (FIG. 4D,E). Ki-67 (MKI67), a marker of proliferation, was also expressed by hypertrophic cells at the TZ (FIG. 4F). Co-staining for collagen X (FIG. 4G) and BrdU, shows that BrdU+ cells can be either positive (FIG. 4H, arrows) or negative (FIG. 4H, arrowheads) for collagen X. To compare cell proliferation between areas of the fracture callus, the populations of BrdU+ cells within immature cartilage (C), hypertrophic cartilage (HC), TZ and new bone (NB) tissues was determined using stereology (FIG. 4I). There are significantly more dividing cells in the TZ than in either C (P=0.0022) or HC (P=0.0001).

Figure 5:
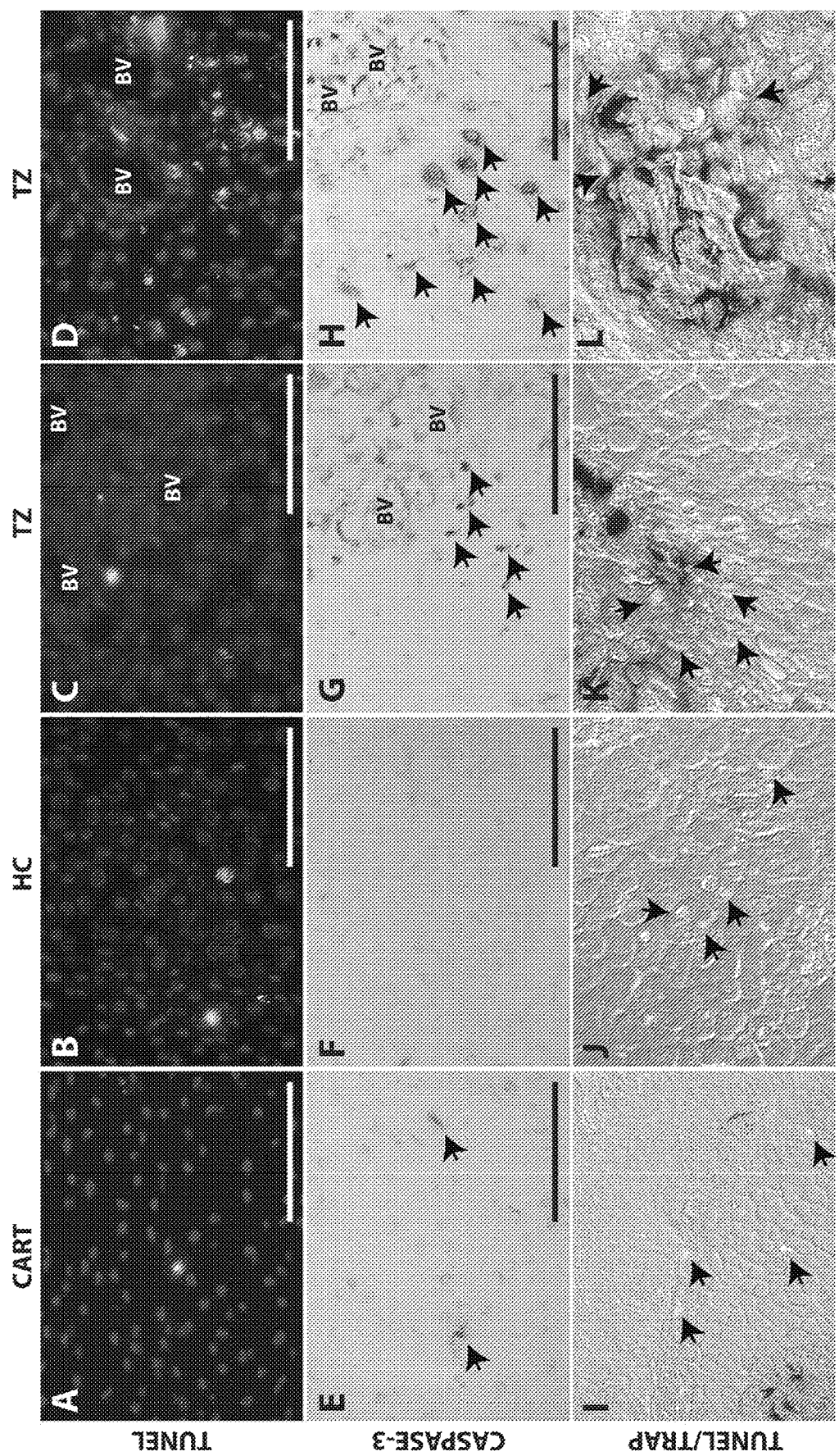
FIGS. 5(A-L) illustrate images showing cell death is not the predominant fate of hypertrophic chondrocytes during endochondral fracture repair. TUNEL staining (A-D), caspase-3 immunohistochemistry (E-H) or co-staining with TUNEL (I-L) to detect dying cells (black arrows) and TRAP to detect osteoclasts (I-L) within immature chondrocytes (A,E,I), HCs away from the TZ (B,F,J), HCs within the TZ (C,G,K) and a region of maximal cell death at the TZ (D,H,L). Scale bars: 100 μm.

To test the classically accepted model that hypertrophic chondrocytes undergo apoptosis, we perform TUNEL staining to identify cells with fragmented DNA and activated caspase-3 immunohistochemistry to indicate cells fated for apoptosis. Minimal evidence of programmed cell death is observed in the immature or hypertrophic cartilage within the fracture callus by either TUNEL (FIG. 5A-C) or caspase-3 staining (FIG. 5E-G). Those cells that are dying are found in close proximity to osteoclasts (FIG. 5I-L), suggesting cell death may be necessary for remodeling of the cartilage to give rise to marrow space. Conversion of cartilage to bone is a continual process that occurs at the edge of the cartilage callus, so the amount of cell death at any given time is expected to be variable; consequently, we included a region of maximal cell death from our analysis of over 20 animals (FIG. 5D,H,L).

Chondrocytes Transdifferentiate to Give Rise to New Bone in the Fracture Callus

Collagen II and aggrecan, the most abundant proteoglycan in the cartilage matrix, are the two classic markers of the chondrocyte. To understand the fate of chondrocytes during endochondral fracture repair, we performed lineage-tracing experiments on cells expressing collagen II and aggrecan by crossing the Ai9 reporter strain to tamoxifen-inducible Col2CreERT and Agc1CreERT mice.

Figure 6:
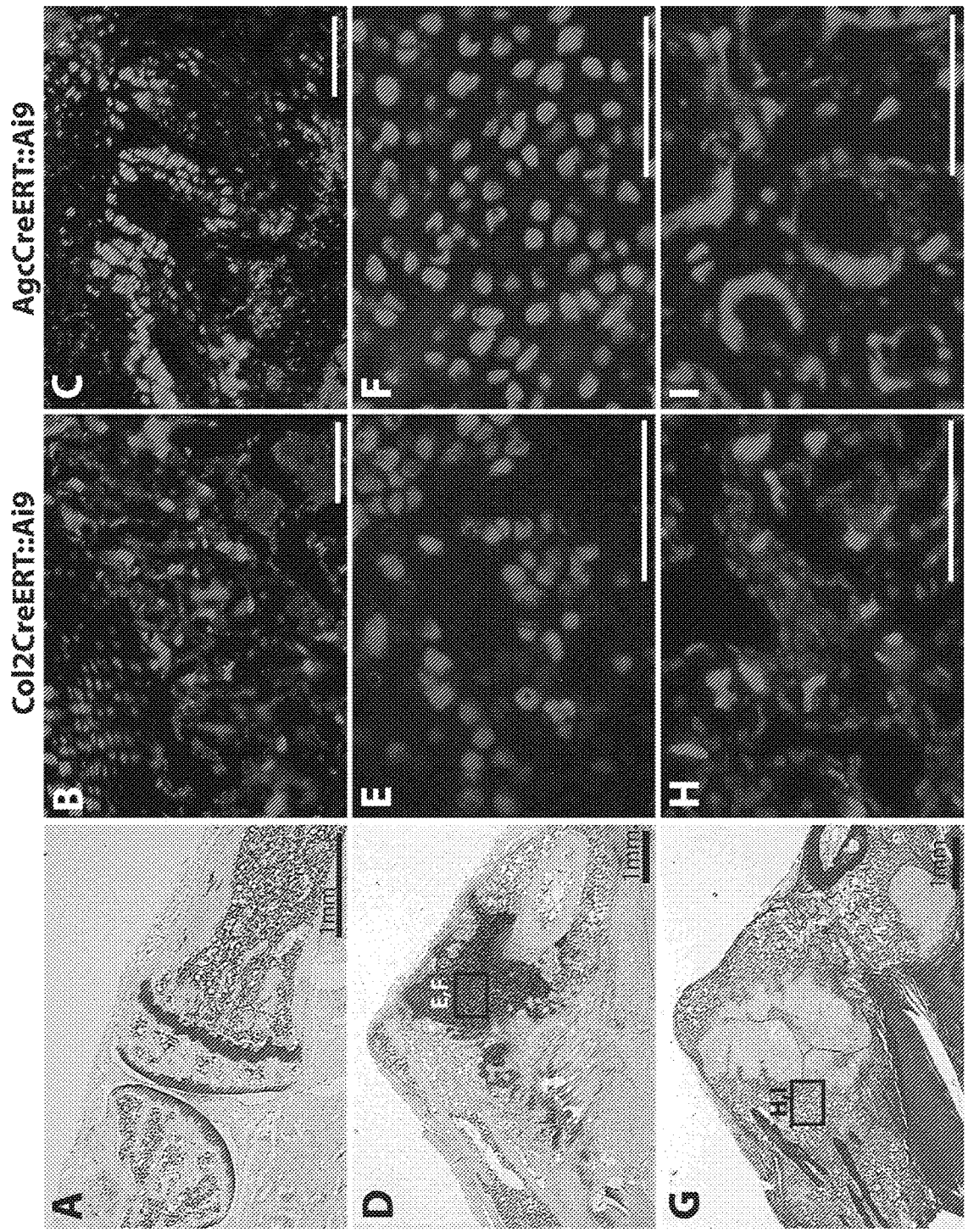
FIGS. 6(A-I) illustrate images showing chondrocytes give rise to osteoblasts and bone lining cells in the newly formed bone during fracture repair. Adult growth plate (A-C), cartilage (D-F) and newly formed bone (G-I) in fracture callus. Col2CreERT::Ai9 (B,E,H) or Agc1CreERT::Ai9 (C,F,I) mice 14 days post-fracture. Scale bars: 100 μm (B,C,E,F,H,I).

Chondrocytes are stochastically labeled in the growth plate (FIG. 6A-C) and fracture callus (FIG. 6D-F) of both the Col2CreERT::Ai9 (FIG. 6B,E,H) and Agc1CreERT::Ai9 mice (FIG. 6C,F,I) indicating effective recombination. We obtained significantly better recombination in chondrocytes in the Agc1CreERT::Ai9 mice (FIG. 6D-F), indicating that it is a more robust genetic tool for analysis of adult regeneration. Together, these mice show chondrocyte-derived cells evident within the matrix (FIG. 6G-I) and lining the surface (FIG. 6I) of the newly formed bone. These data support similar lineage tracing experiments showing that chondrocytes survive and give rise to osteoblasts and osteocytes in the growth plate and bone regenerate.

Hypertrophic Chondrocytes at the Transition Zone Express OCT4, SOX2 and NANOG

Hypertrophic chondrocytes could give rise to osteoblasts by a number of different mechanisms. One possibility is that hypertrophic chondrocytes de-differentiate, or acquire a stemcell-like state, to facilitate a lineage fate switch. Induction of the pluripotency factor Nanog was previously noted during a transcriptional analysis of fracture healing and Oct4A expression was found by immunohistochemistry in hypertrophic chondrocytes during fracture repair.

Here, we aimed to determine the extent to which activation of the core pluripotency-inducing programs [Oct4 (Pou5f1), Sox2, Nanog] is associated with the transformation of chondrocytes to osteoblasts during endochondral repair. Using immunohistochemistry on WT mice (n>12), we find expression of Oct4 and Nanog are low or absent in the immature chondrocytes away from the TZ, whereas Sox2 was expressed in some immature chondrocytes (FIG. 7A-D). Expression of these pluripotency factors becomes more widespread in the hypertrophic chondrocytes around the vasculature in the TZ (FIG. 7I-L). Colocalization of Oct4 and Sox2 is observed within the nuclei of these hypertrophic chondrocytes near the TZ. Within the newly formed trabecular bone, expression of the pluripotent factors is apparent in cells that maintain a hypertrophic morphology (FIG. 7M-P, arrows), but is not observed in cells with osteoblast/osteocyte morphology. Bone lining cells also stain positively for these markers (FIG. 7M-P, black arrows). Expression is not observed in bone outside the TZ, cortical bone or muscle (not shown); but can be observed in the growth plate of adult mice. To understand the lineage of cells expressing pluripotency factors, we performed Oct4, Sox2 and Nanog immunohistochemistry on fractures made in the Agc1CreERT:: Ai9 mice (FIG. 7R-T). The pluripotency programs are active in Ai9+ cells, indicating that these cells were aggrecan-expressing chondrocytes at one point.

Figure 8:
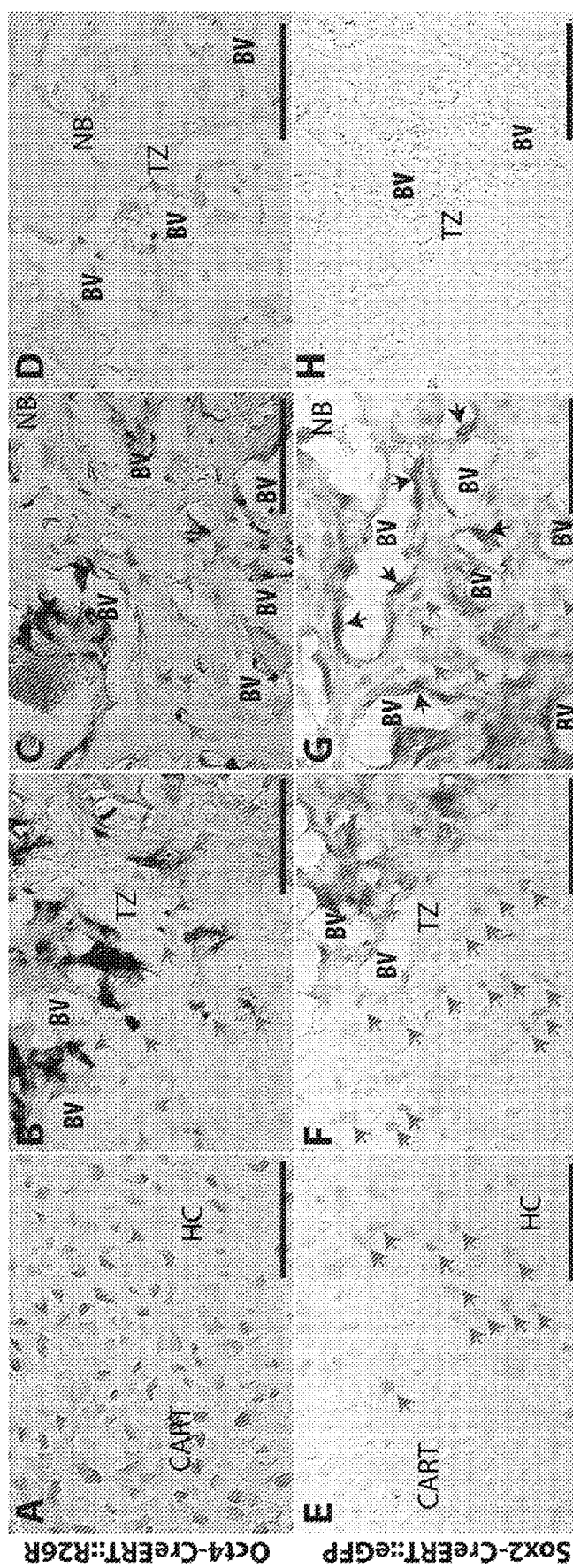
FIGS. 8 (A-H) illustrate images showing transgenic reporter mice for Oct4 and Sox2 demonstrate transformation of chondrocytes into osteoblasts. Oct4-CreERT::R26R (A-D) and Sox2-CreERT::ROSAmT/mG (E-H) mice 14 days post-fracture in cartilage away from the TZ (A,D), TZ (B,E) and NB (C,F). (D) X-gal staining of C57B6. (H) Control with only secondary antibody. Red arrows indicate positive hypertrophic chondrocytes; black arrows, positive bone lining cells. Scale bars: 100 μm.

To map the fate of cells expressing Oct4 or Sox2, we mated the tamoxifen-inducible Oct4-CreERT and Sox2-CreERT mice to the R26R or ROSAmT/mG reporter strains, respectively (FIG. 8). Lineage analysis of Nanogexpressing cells could not be performed because a transgenic mouse with Cre-recombinase under control of the Nanog promoter is not available. At 14 days post-fracture, β-galactosidase staining of calluses harvested from Oct4-CreERT::R26R mice shows no Oct4-expressing cells present in the immature cartilage (FIG. 8A), but Oct4-positive cells are found at the TZ around the new blood vessels and embedded in the newly formed bone (FIG. 8B,C). In the bone matrix further from the TZ, Oct4-expressing cells with both chondrocyte and osteoblast morphology are apparent (FIG. 8B,C).

Figure 7:
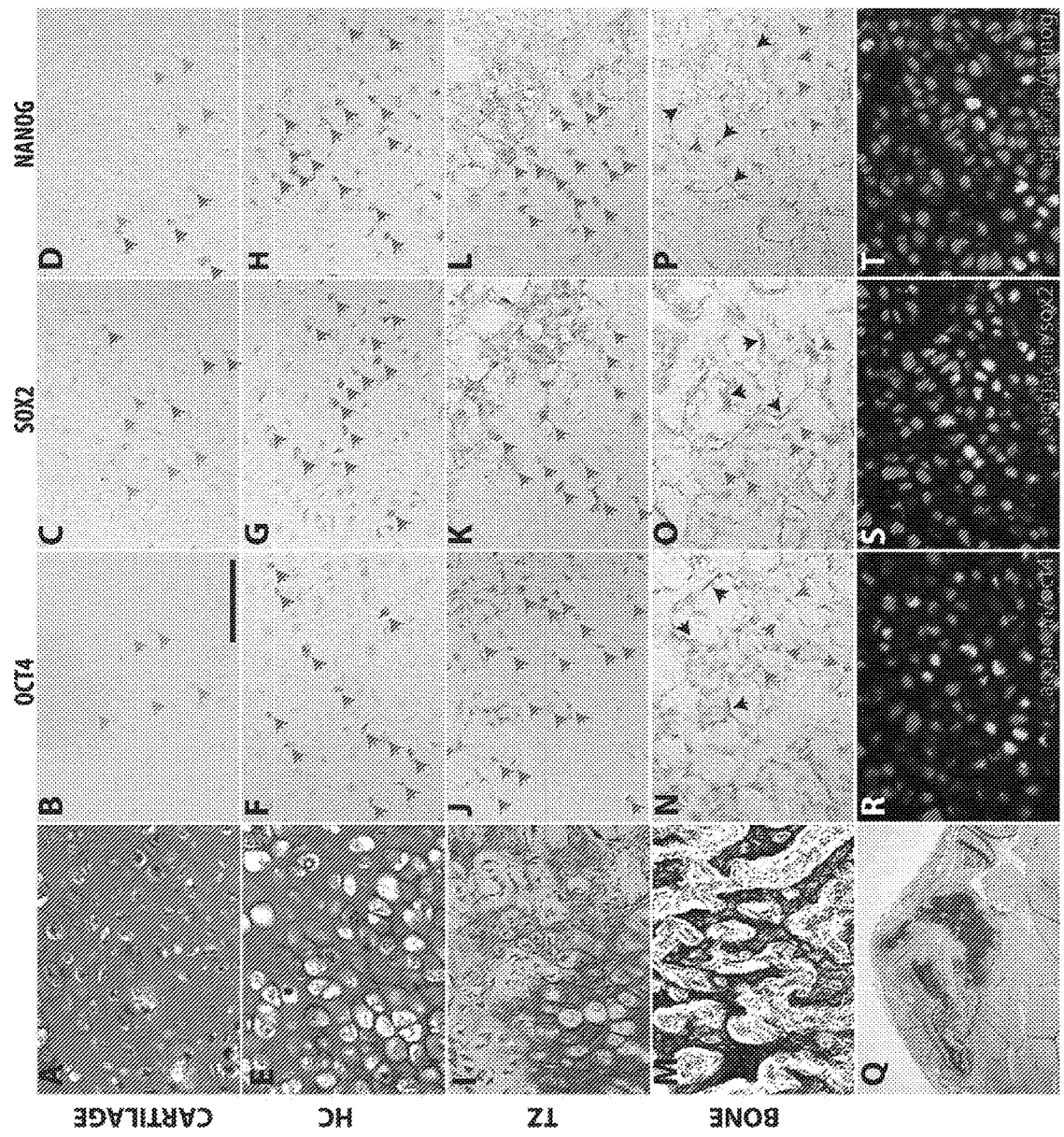
FIGS. 7(A-T) illustrate images showing the expression of pluripotent stem cell programs in the transition zone of the fracture callus. Pluripotent stem cell protein is found in few cells at immature chondrocytes (A-D) but more frequently in HCs near the TZ (E-H) and within the TZ (I-L). (M-P) Within the NB, expression is observed in the HC encased in bone matrix and in bone-lining cells, but not in cells morphologically resembling osteoblasts/osteocytes. (Q) Low magnification of the representative fracture callus on which staining was performed on adjacent sections. (R-T) Cells from the chondrocyte lineage in Agc1CreERT:: Ai9 mice co-stained for Oct4 (R), Sox2 (S), Nanog (T) using an Alexa Fluor 488 secondary antibody.

Similarly, the Sox2-CreERT mouse crossed to the ROSAmT/mG reporter confirms the Sox2 immunohistochemistry results shown in FIG. 7. Owing to strong autofluorescence, GFP-positive cells in Sox2-CreERT::ROSAmT/mG mice are detected by DAB immunohistochemistry. Sox2-CreERT::ROSAmT/mG demonstrates sporadic Sox2 expression in chondrocytes away from the TZ (FIG. 8D). The frequency of Sox2 expression in hypertrophic chondrocytes increases near the TZ (FIG. 8E). In the new bone matrix, Sox2 expression is observed in cells with both hypertrophic chondrocyte and osteoblast morphology (FIG. 8G) and in bone lining cells (FIG. 8G).

SOX2 has a Functional Role in Fracture Healing

Figure 9:
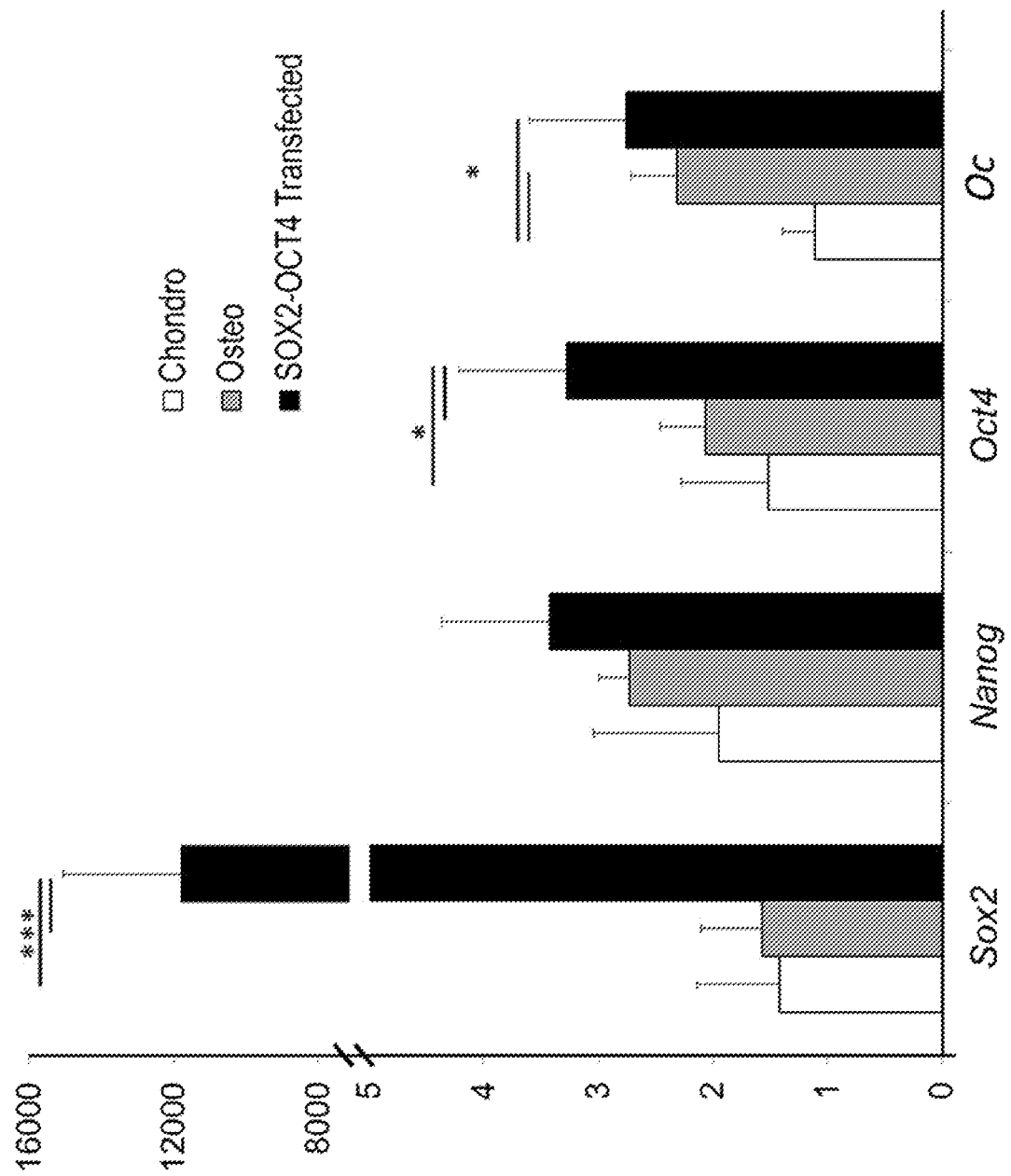
FIG. 9 illustrates a graph showing transfection of OCT4 and SOX2 induces osteocalcin expression in fracture callus cartilage. Relative gene expression analysis of cartilage callus explants cultured in vitro in chondrogenic medium (white), osteogenic medium (gray), or chondrogenic medium with the OCT4-SOX2 transgene (black). Values are means±95% confidence. of n=6.

To test whether expression of pluripotency factors has a functional role in fracture healing we completed gain- and loss-of-function experiments. To test gain-of-function we transfected OCT4 and SOX2 into explanted fracture callus cartilage. Strong expression of Sox2 is observed in the transfected samples when compared with controls, with a more modest, but significant increase in Oct4 expression (FIG. 9). Osteocalcin gene expression was significantly upregulated by both the osteogenic medium and transfection of SOX2 and OCT4, but not chondrogenic medium.

For loss-of-function studies, we compared fracture healing in inducible Sox2 knockout mice (Sox2CreERT/fl) with C57B6 controls, both receiving tamoxifen injections from day 6. Sox2 and Oct4 are effectively lost from the fracture callus of the knockout mice (FIG. 10A,B). Deletion of Sox2 results in significantly decreased total callus size, bone and vasculature volume (FIG. 10C). Similarly, we find a compositional switch from a lower percentage of bone and a higher percentage of cartilage in the Sox2CreERT/f1 mice compared with the control (FIG. 10D).

The Vasculature Coordinates Chondrocyte to Osteoblast Transdifferentiation

Figure 11:
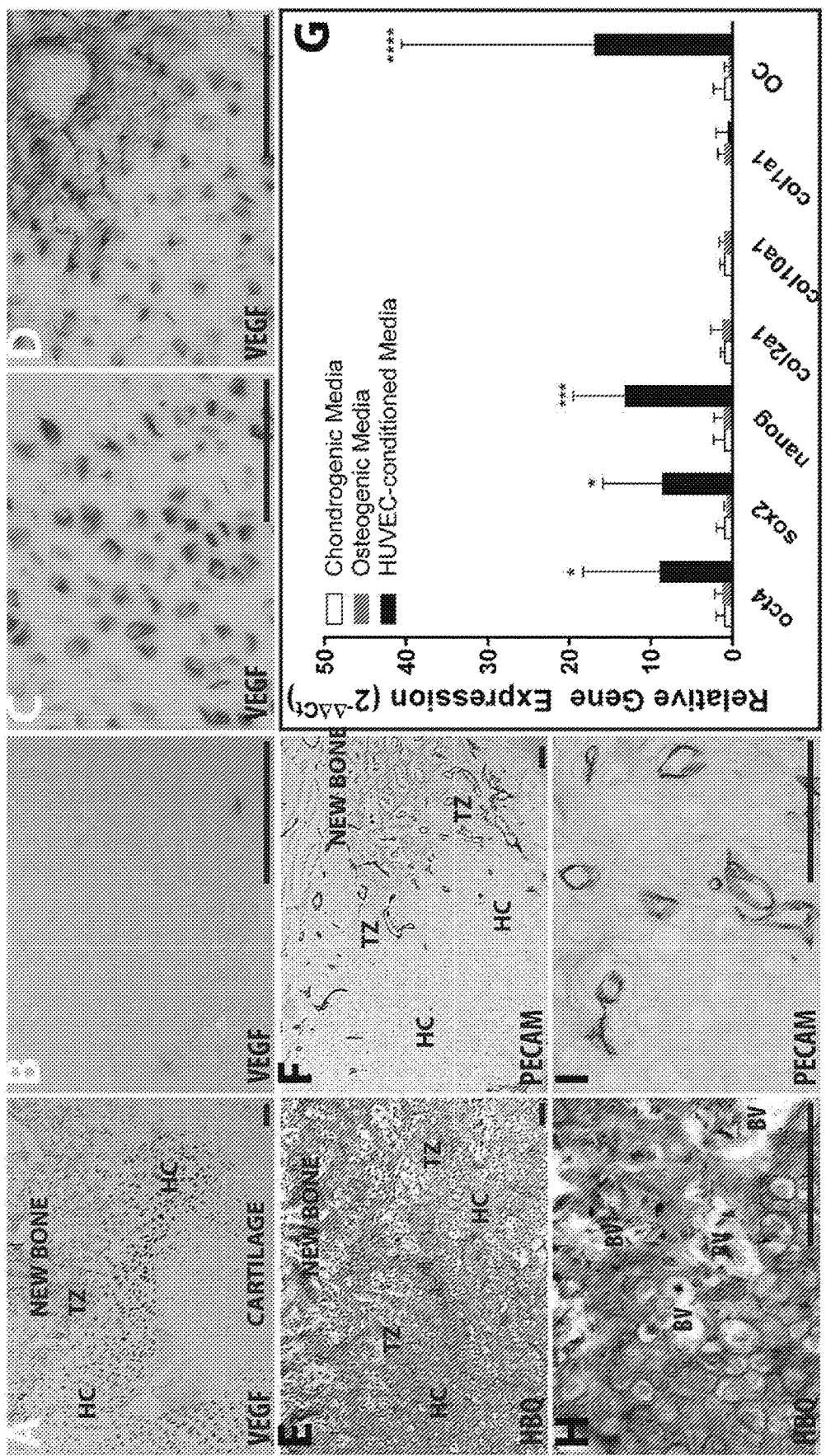
FIGS. 11(A-I) illustrate images and a graph showing hypertrophic chondrocytes recruit vasculature through VEGF expression and vasculature coordinates activation of pluripotent programs. (A-D) Vegf immunohistochemistry (brown) of entire fracture callus (A), immature chondrocytes (B), HCs away from the TZ (C) or HCs in the TZ (D). HBQ (E,H) and Pecam1 (CD31) (F,I) immunohistochemistry (black) on adjacent sections. (G) Relative gene expression of pluripotent, chondrogenic and osteogenic genes for cartilage callus explants cultured in vitro with chondrogenic (white), osteogenic (gray), or HUVEC-CM (black). Values are means±95% confidence of n=4. *P<0.05, *P<0.0005, **P<0.0001. Scale bars: 100 μm.

In hypertrophic chondrocytes, conversion from a chondrogenic to osteogenic genotype (FIGS. 1-3) and expression of the pluripotency factors (FIG. 7) is spatially correlated with vascular invasion (FIG. 11). This is illustrated histologically in the fracture callus by localizing expression of the highly angiogenic vascular endothelial growth factor (Vegf) in the hypertrophic chondrocytes, followed by subsequent invasion of vascular endothelial cells into the TZ. The immature cartilage in the fracture callus is avascular and the chondrocytes do not express Vegf (FIG. 11A,B). As the chondrocytes mature and become hypertrophic, they express Vegf (FIG. 11C) and stimulate vascular invasion [FIG. 11F,I; Pecam1 (CD31) in black]. Vegf is also expressed by the endothelial cells from the invading vasculature and becomes retained in the matrix at the TZ (FIG. 11D). Based on the physical proximity of the blood vessels to the phenotypic changes occurring during the chondrocyte to osteoblast transformation, we hypothesized that the vasculature might serve as a trigger for transdifferentiation.

To test this, we conditioned media with human umbilical vascular endothelial cells (HUVECs) and applied it to fracture callus explants cultured ex vivo. The HUVEC conditioned medium strongly stimulated expression of Oct4, Sox2 and Nanog relative to explants remaining in chondrogenic medium (FIG. 11G). Osteogenic medium does not lead to induction of the pluripotency genes, but both osteogenic and HUVEC conditioned media stimulate osteocalcin gene expression (FIG. 9 and FIG. 11G).

Fate of Chondrocytes in the Fracture Callus

The established model of endochondral ossification suggests that chondrocytes undergo apoptosis and new bone is formed by invading osteoprogenitors. Despite classical support, the only experimental evidence for this model comes from those who conclude that perivascular Osx-CreERT:: R26R cells give rise to trabecular osteoblasts, osteocytes and stromal cells during endochondral ossification. However, as shown here, Osx is robustly expressed by hypertrophic chondrocytes in the fracture callus, indicating that osterix-derived bone may not come exclusively from the vasculature, but could represent a chondrocyte-derived population.

The argument for chondrocyte apoptosis during endochondral ossification comes largely from the data in the growth plate and the suggestion that fracture repair recapitulates aspects of skeletal development. However, since both anatomical structure and microenvironment at the chondro-osseous junction in the growth plate is very different than the fracture callus, it is important to consider that cellular fates may also be different. In this study we show minimal evidence of apoptosis in the TZ during fracture repair using both TUNEL staining and immunohistochemistry for activated caspase-3 (FIG. 4). Importantly, cell death adjacent to osteoclast activity suggests apoptosis aids in conversion of the solid cartilaginous tissue to trabecular bone with marrow space.

In contrast to apoptosis, TZ chondrocytes re-entered the cell cycle, as evident by incorporation of BrdU and expression of Ki67 (FIG. 4). The potential for hypertrophic chondrocytes to undergo cell division in the growth plate has been observed in the chick femur by Roach et al., where they proposed subpopulations of hypertrophic chondrocytes undergo asymmetric cell division to give rise to osteoblasts. More recently, hypertrophic chondrocytes in the growth plate of mice were observed to incorporate BrdU prior to transdifferentiation into osteoblasts. Division of the hypertrophic chondrocyte may explain how these enlarged cells lose volume to acquire the size of an osteoblast. In addition to incorporating BrdU, we provide evidence that TZ chondrocytes activate pluripotency programs, which may help to explain why these cells, unlike the non-dividing hypertrophic chondrocytes away from the TZ, are capable of cell division (FIG. 7).

Chondrocytes Transdifferentiate to Osteoblasts by Activating a Stem Cell-Like State Plasticity of chondrocytes has been demonstrated in a number of studies and, cumulatively, these data suggest that hypertrophic chondrocytes represent a pivotal state between the opposing programs that regulate the chondrogenic versus osteogenic phenotype. Sox9 is essential for transcriptional regulation of chondrogenesis. Osteogenesis is induced by expression of Runx2 and activation of canonical Wnt. Co-expression of Runx2 and β-catenin specifically prevents differentiation toward the chondrogenic lineage by suppressing Sox9 expression. Conversely, ablation of Sox9 in pre-hypertrophic growth plate chondrocytes resulted in acquisition of an osteoblastic phenotype, and overexpression of Sox9 leads to expansion of the hypertrophic zone and delayed ossification.

Downstream, the canonical bone-related genes, osterix (Osx) and osteopontin (Opn), are strongly dependent on Runx2 activity. Homozygous deletion of Runx2 or Osx leads to the complete absence of osteoblasts in mouse embryos, and Osx expression is absent following deletion of Runx2, suggesting that Osx is downstream. Opn, in turn, is transcriptionally regulated by Runx2 and Osx (Ducy et al., 1997; Nakashima et al., 2002). In the fracture callus, we find the hypertrophic chondrocytes in the TZ lose the chondrogenic phenotype (Sox9 expression) and activate osteogenic programs (Runx2, nuclear β-catenin, OC, Opn, Osx, Col1a1) suggesting that these cells are primed for bone formation.

In this example, we found that the hypertrophic chondrocytes acquire plasticity by activating canonical stem-cell programs: Oct4, Sox2 and Nanog. We utilized immunostaining techniques (FIG. 7) complemented by both Oct4 and Sox2 murine reporter systems (FIG. 8) to demonstrate their expression in cells in the TZ. Importantly, by performing immunohistochemistry on fracture calluses harvest from Agc1-CreERT::Ai9 mice, we confirmed that these proteins are observed in cells that were chondrocytes (FIG. 7R-T). We have shown selective hypertrophic chondrocytes in the TZ exhibit positive immunostaining for Oct4A. We found expression of Oct4 in the TZ of the fracture callus, but we used an Oct4 antibody that does not distinguish between isoforms (FIG. 7) because this reflects data obtained with the Oct4-CreERT:: R26R transgenic system used for lineage tracing (FIG. 8). However, Oct4 is localized in the nucleus along with Sox2, and current understanding of Oct4 biology is that only Oct4A localizes to the nucleus.

Within the literature, it is well established that Oct4, Sox2 and Nanog maintain pluripotency in embryonic stem cells and can reprogram terminally differentiated somatic cells into a stem-cell like state. Their role in normal adult tissues remains largely unknown and their activation is currently associated with cancer pathogenesis. Tumors positively genotyped for Oct4, Sox2, or Nanog are associated with a poor prognosis and increased metastasis by enabling cancerous cells to undergo sustained proliferation and evade cell death, suggesting that these genes may confer a stem-like state onto the cancer cells.

Oct4 expression and function in healthy adult tissue is somewhat contentious because of the gene's multiple transcripts and alternative splicing. Oct4A is the isoform associated with pluripotency. Oct4B, another well-known isoform, is not believed to be involved in canonical pluripotency programs and, instead, has been reported to be associated with the cell stress response. One study suggested that Oct4 does not play a role in normal homeostasis since deletion had no effect on adult stem cell populations in the intestinal epithelium, bone marrow, hair follicle, brain or liver. However, fracture healing is not a homeostatic process. Instead, it is a regenerative process that is now understood to involve transformation of chondrocytes to osteoblasts.

Figure 10:
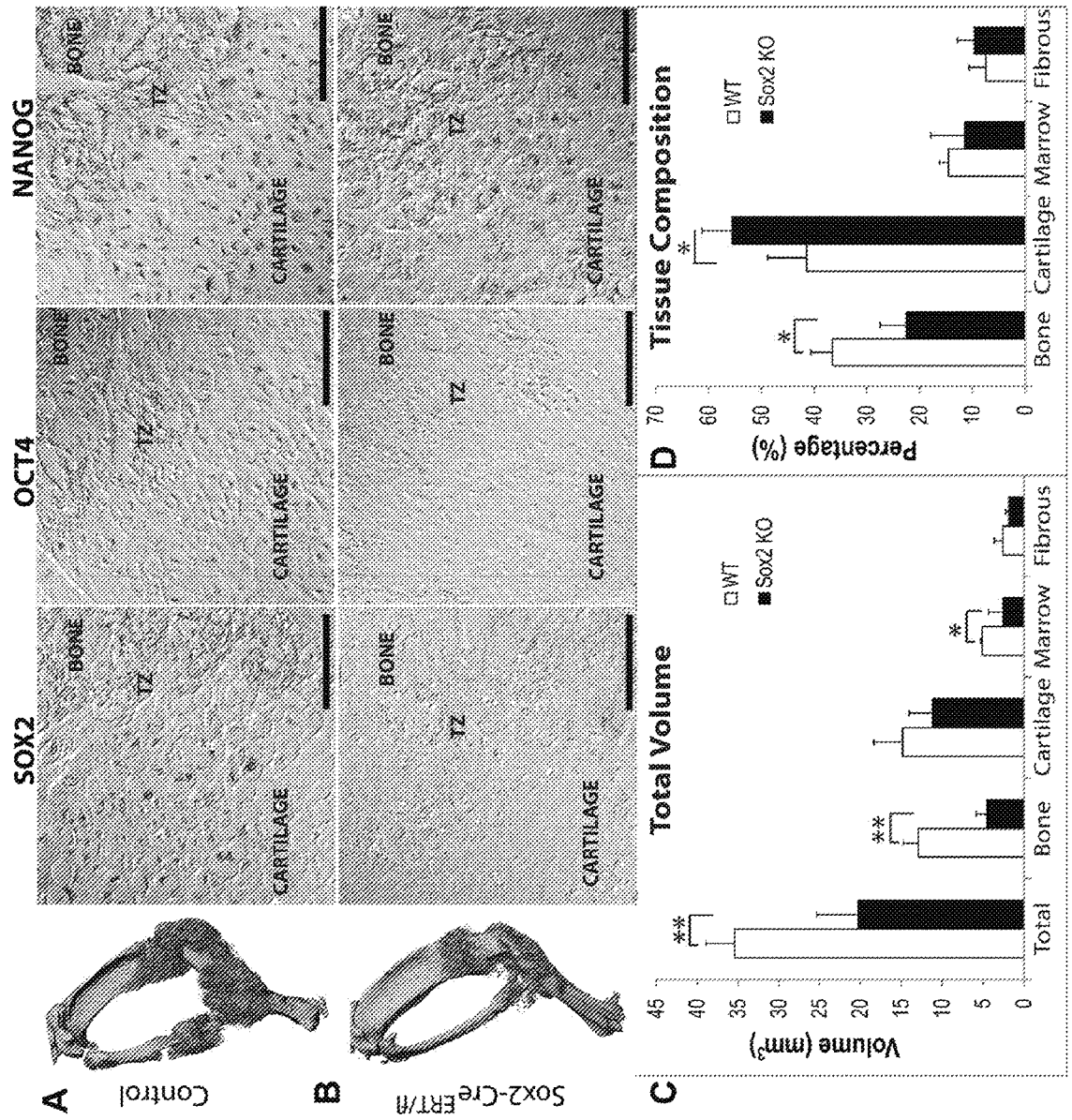
FIGS. 10(A-D) illustrate images and a graphs showing conditional deletion of Sox2 compromises fracture healing. (A,B) μCT shows smaller callus size and immunohistomistry shows reduced expression of Sox2 and Oct4, but not Nanog. Tamoxifen was administered on days 4-7, 10 and 12 days post-fracture in (A) C57B6 control or (B) Sox2-CreER/ fl mice. Histomorphometric quantification of total tissue volumes (C) or tissue composition (D). Values are means±95% confidence of n=5. *P<0.05, **P<0.01. Scale bars: 100 μm.

In contrast to Oct4, Sox2 has been localized to various adult stem cell niches and suggested to have a functional role in maintaining multipotency. In this example, we demonstrated a functional role of Sox2 during fracture healing through a significant decrease in fracture callus and bone formation following conditional deletion of the protein from days 4 to 12 during endochondral repair (FIG. 10). Sox2 was first suggested to play a role in maintaining the multipotency and self-renewal capacity of stem cells in the adult hippocampus. Subsequently, Sox2-positive cells have been identified in several epithelial tissues, including stomach, cervix, anus, testes, lens and multiple glands. Lineage tracing experiments demonstrated that these Sox2-expressing cells represent an adult stem cell population with both self-renewal and differentiation potentials. Sox2 has also been associated with continuous eruption of the murine incisor. The labial cervical loop of the mouse incisor contains a pool of Sox2-expressing cells that are capable of giving rise to all the epithelial lineages of the tooth, including ameloblasts, which produce the enamel Less is known about the post-natal role of Nanog outside tumorigenesis, but it was previously identified as a transiently expressed gene in a transcriptional analysis of fracture healing and is involved in bone regeneration by its contribution to marrow stromal cell maintenance and differentiation. More recently, Nanog was also shown to regulate cell division in stratified epithelia in adult organisms.

Role of the Vasculature in the Transformation of Chondrocytes to Osteoblasts

An intact vasculature is essential for bone fracture healing. The delayed and non-union rate is 10-20% in the overall population, but it increases to almost 50% in the presence of vascular injuries. However, the reason for this is unknown. Vascular invasion of the cartilage callus is an important step during endochondral repair and fracture healing is significantly delayed when the vasculature is disrupted. Previous studies suggest that the endothelial cells enable degradation of the cartilage matrix by producing MMP-9, facilitate mineralization of the cartilage matrix by secreting BMPs and regulate deposition of collagen I.

Results from our study show the vasculature has a signaling role in regulating transformation of chondrocytes to osteoblasts. Paracrine factors secreted from the vascular endothelial cells may trigger the chondrocyte to osteoblast transformation by activating the pluripotent stem cell programs, initiating cell division and/or stimulating the bone phenotype. This model is supported by immunohistochemical analysis of the expression of Sox2, Oct4 and Nanog within the TZ and in vitro data demonstrating upregulation of these genes in cartilage explants cultured with HUVEC conditioned medium (FIGS. 4,7,11).

Model of Endochondral Ossification During Bone Fracture Healing

Figure 12:
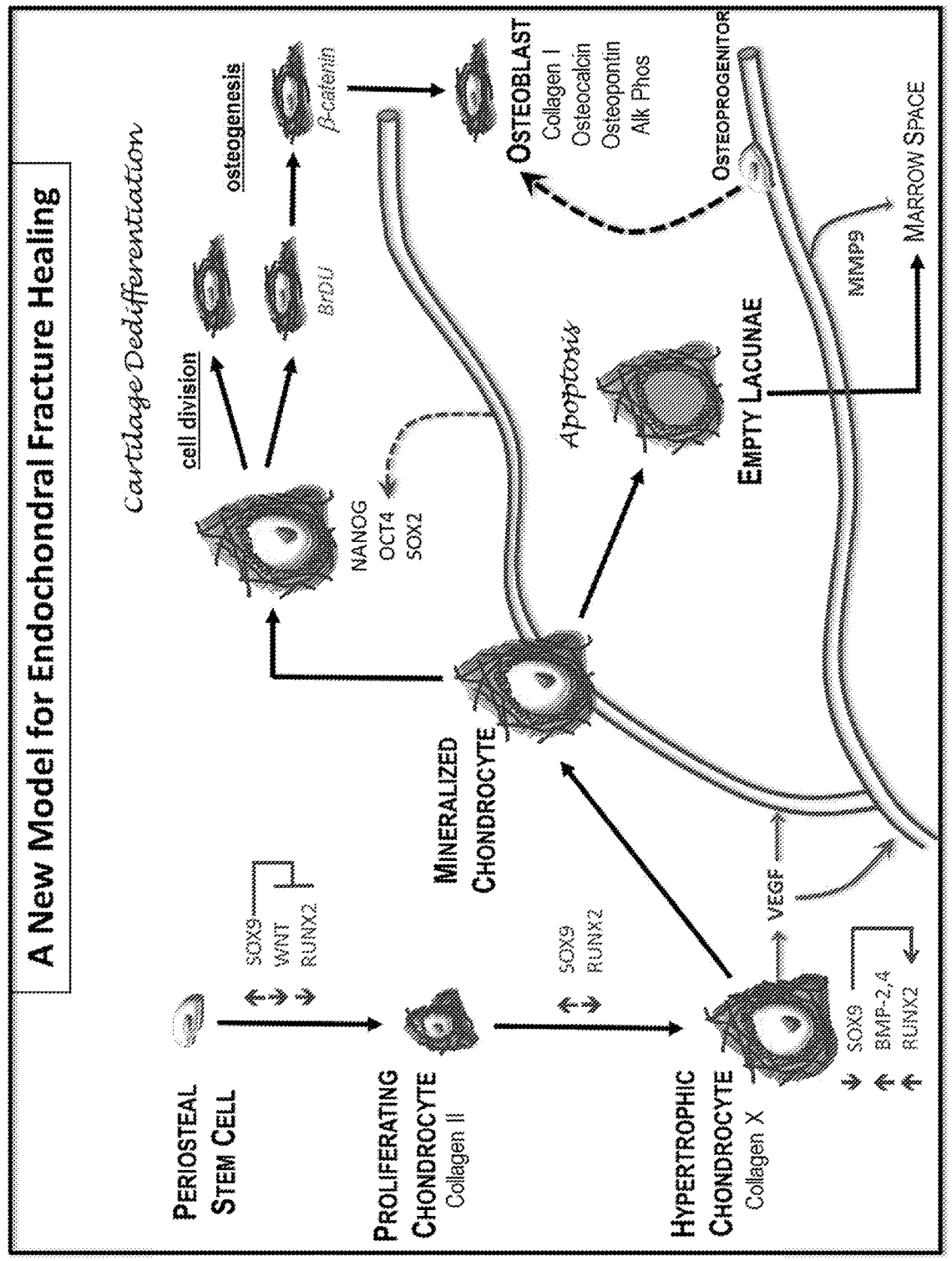
FIG. 12 illustrates a schematic of a model for endochondral ossification during fracture healing. Local osteochondral progenitors from the periosteum and endosteum are the stem cells that differentiate to form bone and cartilage in the fracture site. To generate the cartilage callus, osteochondral progenitors differentiate into chondrocytes that proliferate to generate the early soft callus. Chondrocytes within the callus mature to hypertrophy and express angiogenic factors that result in vascular invasion. Mineralization of the hypertrophic cartilage occurs in the TZ where blood vessels have invaded. Some hypertrophic chondrocytes undergo cell death to facilitate remodeling of the solid cartilage callus and create marrow space within the trabecular bone. Other hypertrophic chondrocytes regain some stem cell-like properties by expressing the pluripotent transcription factors OCT4, SOX2 and NANOG. These large cells re-enter the cell cycle, divide and then transform into osteoblasts. The identity and origin of the signal that triggers the chondrocyte-to-osteoblast transformation remains unclear. Both the vasculature and cell autonomous signals from the hypertrophic chondrocyte may facilitate this change (dotted arrows). This model does not exclude previously proposed systems in which osteoblasts in the newly formed bone are derived from osteoprogenitors that are brought in by the invading vasculature.

Taken together with recent studies, this example shows that chondrocytes are a major precursor of the osteoblasts/osteocytes during endochondral bone repair. Importantly, this example shows mechanisms through which chondrocyte-to-osteoblast transformation occurs, and we propose a new model for endochondral fracture repair in which the hypertrophic chondrocytes regain some stem cell-like functionality to facilitate the lineage change (FIG. 12). While our data does not demonstrate that chondrocytes regain multipotency, we do show that activation of pluripotency programs has a functional role during fracture healing and propose that this allows for epigenetic remodeling to switch off chondrogenic programs and induce osteogenic programs.

EXAMPLE 2

Accelerate Endochondral Ossification Through Activation of a Stem-Cell Like State in Hypertrophic Chondrocytes Example 1 shows that stem cell programs are activated in chondrocytes in the fracture callus, that genetic deletion of Sox2 impairs fracture healing, and that transfection of fracture callus cartilage explants with Sox2 and Oct4 upregulates osteocalcin gene expression. Taken together these data support the idea that acquisition of a stem cell like state has a functional role in endochondral ossification and that therapeutically targeting this step of fracture healing could accelerate conversion of cartilage to bone. In this example, we show the upstream signal(s) that affect expression of the stem cell transcription factors, and subsequently test two independent therapeutic strategies to promote this state.

Conversion of cartilage to bone histologically corresponds with vascular invasion (FIGS. 11(A-B)). Hypertrophic chondrocytes themselves mediate this angiogenesis through expression of VEGF17-20 and PlGF21. Previously, we have shown that culturing fracture callus cartilage explants in human umbilical vascular endothelial cell-conditioned media (HUVEC-CM) induced mineralization of the cartilage. Using the same HUVEC-CM, we now show that endothelial cells strongly induce expression of the pluripotency genes in the fracture callus cartilage in a BMP-independent manner (FIG. 11).

Furthermore, in embryonic stem cells leukemia inhibitory factor (LIF), an interleukin 6 (IL6) family member, maintains pluripotency by inducing expression of Sox2 and Nanog. LIF binds to the GP130 and LIF co-receptors, which phosphorylates the JAK/STAT pathway to turn on expression of Klf4. Klf4 directly induces expression of Sox2. In parallel, LIF activates phosphoinositide-3 kinase to induce expression of the transcription factor Tbx3 and subsequently Nanog. Together Sox2 and Nanog converge to regulate Oct4. We have found expression of LIF, GP130, Tbx3 and Klf4 in the hypertrophic chondrocytes in the transition zone (FIG. 13), indicating that these pathways are involved in regulating transformation. The functionality of LIF was also tested through ex vivo stimulation of fracture callus cartilage; we find that exogenous delivery of LIF strongly activates expression of pluripotency genes (FIG. 14A) and that we can knock down expression of these genes through a morpholino to Klf4 (FIG. 14B).

Together these data indicate that induction of the pluripotency genes in fracture callus chondrocytes happens in response to soluble factors from endothelial cells, or through LIF, supporting that these a novel therapeutic candidates for stimulating a stem cell like state during endochondral bone regeneration.

Rates of Endochondral Bone Formation Following Addition of Either LIF or Endothelial Cells to MSC-Derived Chondrocytes We have previously created MSC-derived cartilage pellets and implanted them into a segmental defect in a mouse to demonstrate that they undergo endochondral bone formation. Here our objective is to accelerate endochondral bone formation from MSC-derived chondrocytes by stimulating a stem cell like state in these pellets through addition of endothelial cells or LIF-delivery.

We use both in vitro and in vivo models to test osteogenesis of the MSC-derived chondrocytes following addition of endothelial cells or LIF-delivery. The same outcome measures will be used for all treatments to understand how they compare to each other, and to chondrocytes alone.

Hypertrophic Chondrocyte and Endothelial Cell Bi-Layer Pellets (In Vitro)

Human bone marrow derived MSCs is collected from young healthy patients through our IRB approved protocol or purchased from a commercial source. MSC pellets are created by centrifuging 200,000 cells at 500×g and culturing in vitro for 3 weeks in non-cell adherent plates in standard chondrogenic media containing transforming growth factor-β (TGFβ). HUVECs are added at a 1:4 ratio to the circumference of the pellet to create a bi-layered construct; conceptually similar the stage of fracture healing that vascular invasion begins.

In vitro osteogenesis of the co-cultured pellets is compared to chondrogenic pellets maintained in standard chondrogenic media, osteogenic media, or the basal HUVEC medium and quantified using a complete molecular and cellular characterization. To determine matrix composition we quantify mineral content (Cayman's Calcium assay), sulfated proteoglycans (DMMB assay), DNA content (Hoechst), and collagen content (hydroxyproline assay) as described previously. Pellets are also processed for qRT-PCR and chondrogenic (Col2a1, ACAN, Col10a1), osteogenic (osteocalcin, osteopontin, osterix, Col1a1), angiogenic (VEGFa), pluripotency (Sox2, Oct4, Nanog) and LIF genes will be assayed. Histology and immunohistochemistry will permit examination of matrix mineralization (Alizarin Red), chondrogenic phenotype (collagen II, collagen X), osteogenic phenotype (osteocalcin, Runx2), and angiogenesis (PECAM, VEGF).

Hypertrophic Chondrocytes with LIF-Microparticles (In Vitro)

We have previously defined a working concentration of LIF (2,000 units/ml, EMD Millipore ESG1106) that stimulates stem cell expression following 48 hrs of culture. (FIG. 14A) The goal is to deliver LIF to MCS-derived chondrocytes using the gelatin microparticle system. TGFβ and LIF have an affinity to gelatin, and the factors are released in response to cell-secreted collagenases. Temporally-controlled delivery of bioactive factors can be achieved by utilizing microparticles with different presentation kinetics by modulating the crosslinking density of gelatin, which affects their susceptibility to enzymatic degradation. TGFβ is delivered first through gelatin microparticles capable of relatively rapid presentation of the growth factor to induce chondrogenesis, and LIF subsequently presented over a more sustained time period using gelatin with increased crosslinking. This system will promote early differentiation of MSCs to chondrocytes, and then delayed LIF delivery will activate the stem cell genes.

The cellular and molecular characterization of LIF-containing pellets is done using the same outcome measures described for chondrocyte-HUVEC co-cultured pellets. MSC pellets cultured with TGFβ-containing gelatin microparticles only will be the control. In a second control, the same pellets receive 5 nM β-glycerol phosphate (βGP) supplementation to the basal chondrogenic media starting at 2 weeks to enable mineralization. The LIF-containing pellets are cultured in either chondrogenic conditions or with addition of βGP at week 2. Pellets are harvested after 1, 2, 3, and 4 weeks.

In Vivo Bone Regeneration

Following comprehensive characterization and optimization of these pellet systems in vitro, we will test our murine model of non-union to determine functionality in a clinically relevant system. Briefly, the tibia is externally stabilized a murine-sized Ilizarov apparatus and a critical sized segmental defect generated mid-diaphysis by osteotomy. The chondrogenic control pellets used in vitro and tested previously is compared to the cartilage-HUVEC bi-layered pellets and LIF-containing pellets that induce the strongest stimulation of the stem cell programs. Two pellets are press-fit into the defect, the muscle and skin closed, and the animal allowed to heal for 2, 4, or 8 weeks. At each time point tibia is harvested and processed for expression of the chondrogenic, osteogenic, pluripotency factors by RT-PCR.

To quantify the rate of bone formation we determine cell proliferation within the regenerate (injecting BrdU 2-hrs prior to harvest), rate of mineral deposition using calcein and alizarin red injections one week apart, and bone/cartilage composition by histomorphometry. We can quantify bone mineral density (BMD), bone volume and trabeculation. In addition to osteogenesis is used to evaluate vascularity using PECAM immunohistochemistry to identify the vasculature and stereology to quantify capillary surface density and marrow space. Finally, we can assess integration and regenerate strength using 3-point bending.

Based on our preliminary studies we believe that co-culture of the MSC-derived chondrocytes with either HUVECs or LIF-delivery can activate the stem cell program in these chondrocyte and we expect that this can then accelerate osteogenesis in vitro and in vivo. Since a key step in endochondral ossification is vascular invasion, and we see robust tubule formation in the HUVEC-chondrocyte bi-layer pellets, we anticipate these pellet will demonstrate faster osteogenesis and enhanced angiogenesis relative to the chondrogenic control and LIF-system. If this is true we will find a higher composition of bone at earlier time points, a larger mineralization band, increased BMD, and increased capillary surface density with more trabeculation in the bi-layer pellets in vivo.

Stimulate Fracture Repair With LIF

LIF is an appealing therapeutic molecule for direct application during fracture repair. The objective is to determine if LIF-injections can accelerate fracture healing when delivered to the cartilage phase of endochondral repair.

We utilized a fracture repair model that promotes robust endochondral ossification and has been well characterized at a molecular and cellular level by our group. Fractures are made by inserting a sterilized stainless steel insect pin into the intramedullary canal of the tibia proximally through the femoral head (FIG. 15A). The pin will be placed half way down the diaphysis, position confirmed by fluoroscopy, then a mid-shaft osteotomy created, and the pin pushed through to provide partial stability. This fracture model heals robustly 28-days post-injury (FIG. 15B).

LIF is injected into the fracture gap by fluoroscopy-assisted placement with a Hamilton syringe to deliver 10 μl of 2,000 units/ml of LIF in PBS. LIF will be delivered at day 10 with a single injection, or with five daily injections on days 8-12 post-fracture. These time points were chosen because maximal conversion of cartilage occurs between days 10-18 post fracture and we aim to shift conversion earlier to accelerate bone repair. We will confirm activation of the pluripotency programs (Sox2, Oct4, Nanog) in vivo by harvesting the fracture callus for qRT-PCR and immunohistochemistry to determine the effect of single versus 5-day dosing of LIF (2 hrs, 12 hrs, 48 hrs, 5 days, and 7 days following the first injections). Bone healing is quantified at days 12, 14, 18, 21, and 28 post-fracture using histomorphometry, βCT, and biomechanics and compared to PBS-only injections.

We anticipate that LIF delivery will accelerate endochondral fracture repair as determined by an increased percentage of bone in the fracture callus, increased BMD, and increased strength at days 12, 14, and 18. We don't expect to see changes at days 21 and 28 since the mouse can robustly heal the tibia in this model 28 days after surgery, but we include these time points to ensure healing isn't delayed.

While we propose the use of LIF therapeutically, IL6 could be an appropriate alternative. Delayed fracture repair has previously been described following genetic deletion of IL6. Mechanistically, IL6 is both a proinflammatory cytokine and an anti-inflammatory cytokine. We have previously found that a robust proinflammatory response is essential during the early phase of repair, and that appropriate fracture healing subsequently requires resolution through an anti-inflammatory response.

Additionally, we propose using the simplest mechanism for local delivery of LIF through injection. We have used injection to effectively deliver multiple therapeutic agents, including BMP46. We believe simple injection is appropriate in this system because our in vitro data and model suggest that we only need a temporary activation of the pluripotency genes to facilitate chondrocyte to osteoblast transdifferentiation.

Promote Endochondral Repair With Therapeutic Activation of Canonical Wnt Signaling in Cartilage Callus Canonical Wnt signaling is essential for bone formation. Wnts are a large family of secreted factors that stimulate bone formation through Frizzled and the low density lipoprotein receptor related protein (LRP5 or LRP6) co-receptors, which leads to activation of β-catenin. Regulation of osteogenesis comes from molecular interaction of the transcription factors runx2 and β-catenin, which actively suppress sox9 to inhibit chondrogenesis. Extensive work has been done using conditional knock out mouse models to establish the role and timing of Wnt during development. Inhibiting β-catenin activity in the osteoblast lineages leads to decreased bone mass and increased chondrogenesis, while blocking inhibitors of Wnt through DKK53 or sclerostin, increases bone formation and bone mass.

While the developmental role of canonical Wnt has been demonstrated, significantly less is known about its role during fracture healing. Fracture studies in Wnt deficient mice suggest impaired healing compared to wild type littermates, and a therapeutic benefit has been shown when canonical Wnt signaling was stimulated by adding a monoclonal antibody to the Wnt inhibitor DKK. However, the therapeutic effect of activating Wnt was determined immediately post-injury and therefore predominantly influenced intramembranous healing.

During endochondral fracture repair we show both runx2 and β-catenin (FIG. 16A) are expressed in hypertrophic chondrocytes at the transition zone. Further, culture in HUVECCM is sufficient to mineralize cartilage callus explants in vitro, and now we have evidence that HUVEC-CM activates canonical Wnt signaling using 293 cells transfected with Super TopFlash luciferase (FIG. 16B). Together these data show Wnt is involved in transdifferentiation by activating an osteogenic phenotype in chondrocytes. Supporting this idea is work demonstrating chondrocyte specific deletion of β-catenin results in ectopic cartilage, while overexpression in chondrocytes activates canonical bone programs.

Based on our preliminary data, we believe activation of Wnt in the cartilage phase of bone healing holds promise as a treatment for fracture non-union. In this example, we will test a novel water-soluble Wnt agonist as therapeutic activator of endochondral ossification. Therapeutic consideration of Wnt ligands has previously not been possible because Wnts are lipid soluble; therefore, producing large quantities of protein in a cost-effective manner is not possible. Consequently, current therapeutic strategies to stimulate Wnt signaling utilize indirect techniques that block inhibitors of Wnt (e.g. DKK and sclerostin).

Here, we utilize a Wnt agonist, Wnt Surrogate (WntS). WntS is an engineered mimetic that directly activates the Wnt pathway and is easily mass-produced, overcoming translational barriers. Extensive efficiency studies have been performed to validate WntS as an agonist the canonical Wnt pathway. Specifically, the WntS binds Frizzled receptors 1,2,5,7, and 8; enhances nuclear accumulation of β-catenin; promotes cell proliferation; and up-regulates Wnt target genes and lineage-specific markers in a Wnt-like manner (FIG. 17).

Characterize and Optimize Osteogenic Effect of Wnt Surrogate In Vitro

While the Wnt Surrogate (WntS) has been extensively validated for activation of the canonical Wnt pathway (FIG. 17), it has not been tested in vivo and its effects on intramembranous and endochondral bone formation are unknown. The objective is to understand and optimize the osteogenic potential of WntS using in vitro models of intramembranous and endochondral ossification. Intramembranous ossification (in vitro): Intramembranous bone forming potential will be tested in vitro through osteogenesis of the pre-osteoblast cell line MCT3T-E1-subclone 4 and human bone marrow-derived MSCs. We will test a therapeutic range of the Wnt Surrogate between 0.2-50 nM in the media and compare osteogenesis to BMP, positive Wnt controls (Wnt3a ligand and GSK inhibitor SB216763), or negative control (basal medium). Activation of the Wnt pathway will be confirmed by qRT-PCR to axin2. Osteogenesis will be measured by osteogenic gene expression (col1a, osteocalcin, osteopontin), alkaline phosphatase activity, and mineralization (Cayman's Calcium assay and/or Alizarin Red). We will also quantify cell proliferation (DNA assay) and normalize osteogenic data to cell number. After we optimize WntS dosing we will demonstrate pathway specificity by adding limited dilutions of DKK to the media and measure changes to oteogenesis and cell proliferation. After completing preliminary WntS dosage studies we now demonstrate that 0.2 nM WntS activates axin2 gene expression and is osteogenic for both MCT3Ts and MSCs. (FIG. 18).

Endochondral Ossification (In Vitro)

Figure 19:
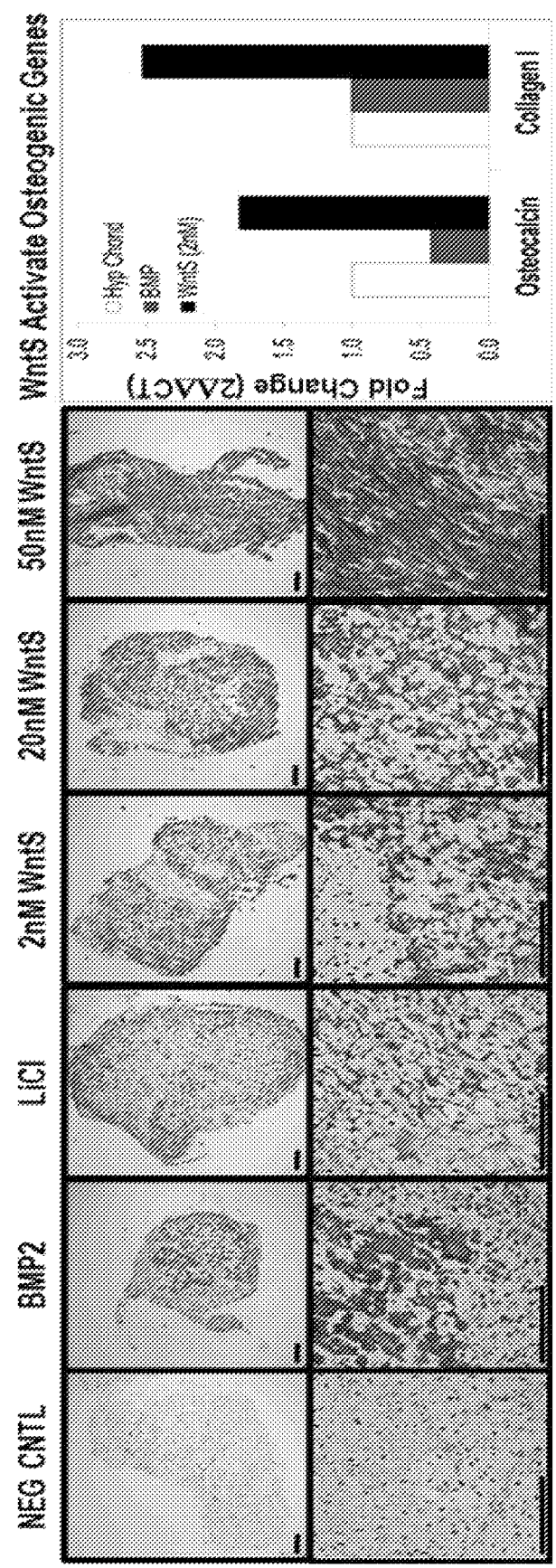
FIG. 19 illustrates images and a graph showing WntS promotes osteo-genesis in cartilage explants. Alizarin red staining on fracture callus cartilage explants treated with a range of WntS compared to BMP or chondrogenic control media. qRT-PCR gene expression demonstrates 2 nM WntS upregulates osteocalcin and col1. Scale=100 μm.

We have developed a fracture callus explant system that allows us experimentally test endochondral ossification in vitro. Using this system, we will deliver WntS to the cartilage callus (0.2-50 nM) and compare to BMP, positive Wnt controls (Wnt3a ligand and SB216763), and negative control (basal medium, or medium plus DKK inhibitor). Downstream activation of axin2 will be confirmed, along with analysis of the chondrogenic, osteogenic, angiogenic, and pluripotency genes by qRT-PCR. We will quantify cell number, proteoglycan content, and mineralization by digesting the pellets in papain and using the PicoGreen, DMBM, and Cayman's calcium assay as described previously. We will also embed some replicates for histology in order visualize mineralization (alizarin red) and collagen I, osteocalcin, Ki67 (proliferation), VEGF, Sox2, and LIF by immunohistochemistry. We found that WntS can mineralize cartilage explants and activate osteogenesis (col1, osteocalcin), but may require a higher dose than intramembranous ossification (FIG. 19).

We have validated the osteogenic capacity of the WntS and determined effective therapeutic ranges for delivery during either intramembranous or endochondral ossification. We found that serum inhibited WntS activity. To overcome this issue we now use FBS-free defined medium.

Controlled Release Hydrogel for Delivery of Wnt Surrogate

Aberrant Wnt activation can be oncogenic; consequently, the objective is to develop a system for controlled and local delivery of the Wnt Surrogate. During normal murine fracture healing, maximal conversion of cartilage to bone occurs from days 10-18 post-fracture. To align with this timing, we can use an injectable hydrogel to deliver 1 mg WntS/day for a minimum of one week. This concentration was chosen because 50 nM WntS demonstrated maximal mineralization of cartilage explants (FIG. 18), we can inject 20 μl of the hydrogel into the fracture, and we expect some decrease efficiency in vivo.

To do this we will utilize calcium-crosslinked oxidized alginate hydrogels for controlled release of the WntS. WntS is engineered with 31 positively (Arg/Lys) and 23 negatively (Asp/Glu) charged amino acids, with a partial crystal structure predicting net positive charge based. Consequently, ionic interactions between the positively charged WntS and the negatively charged alginate produces controlled release. In addition, the aldehyde groups of oxidized alginate and amine groups of Wnt form unstable imine bonds, aiding in retention within the gels (FIG. 20A). Following preliminary studies, we have determined that 4 wt % calcium-crosslinked alginate hydrogels with 5% oxidation efficiency provide the appropriate form factor for injection into the fracture callus. Furthermore, we have optimized physical degradation of the alginate gel such that this hydrogel composition results in ~40% degradation within a week (FIG. 20B).

In addition to characterizing the physical degradation more completely, we will also quantify release and retention of WntS from the alginate hydrogel using quantitative infrared red western blot and a validated antibody to WntS with a LI-COR scanner. We will also utilize the TopFlash reporter assay shown above (FIG. 16B) to correlate release kinetics with in vitro Wnt activity and test the ability of the WntS-alginate hydrogel to promote in vitro bone formation using the intramembranous and endochondral assays.

We expect that 1 mg WntS/day for a minimum of one week can effectively promote bone formation in vitro and in vivo, and that we can effectively achieve this using the 4 wt % calcium alginate hydrogels with 5% oxidation that we developed.

Wnt Signaling During Normal Endochondral Ossification

There is limited data regarding the spatiotemporal expression of Wnt signaling during endochondral fracture repair, and it hasn't been studied specifically as mediator of chondrocyte to bone transdifferentiation. Consequently, we will make fractures in as described above (FIG. 15) in C57/B6 mice and perform qRT-PCR, in situ hybridization, and immunohistochemistry for Wnt ligands and the Frizzled receptors at days 5, 7, 10, 14, 18, and 21 post fracture. We will also cross our existing Axin2-eGFP mouse with our Agc1-CreERT::Ai9 mouse to allow us to look for axin2 expression in lineage labeled chondrocytes following fracture. These data will serve as the control for WntS injected animals, inform WntS delivery timing, and provide new data on Wnt during endochondral repair.

Bone Healing Following WntS Delivery

The alginate hydrogel was partially chosen for its ability to be injected in situ adjacent to the healing bone without disrupting the fracture callus, yet providing controlled delivery. We will use a Hamilton syringe to inject 20 μl alginate hydrogel, either alone or loaded to deliver 1 mg/day WntS, at 8 days post-fracture. The goal is to accelerate osteogenesis in the cartilage callus by activating Wnt signaling. We will test this by looking for axin2 expression either by RT-PCR or using the Axin2-eGFP reporter mouse at 10, 14, 18, and 21 days post-fracture. At these time points we will also quantify osteogenic (col1, osteocalcin), chondrogenic (col2, col10), angiogenic (Vegf-α), proliferative (Ki67), pluripotency (Sox2, Oct4, Nanog) and Lif gene expression. We will perform histomorphometry, μCT and biomechanics to quantify bone formation and quality 10, 14, 18, 21, and 28 days post-fracture. To ensure safety of WntS we will run complete CBCs, RT-PCR for pro-inflammatory cytokines on the spleen (considered homologous with circulatory system in mice), and collect intestine to confirm no tumor formation.

EXAMPLE 3

In this Example, we investigated the therapeutic potential of delivering the cholinergic agonist, carbachol, for fracture repair. This example is motivated by our data demonstrating a functional role of the cholinergic nerve in bone regeneration. Preliminary work suggests that neuronal signaling may have a role in fracture healing. Furthermore, these data suggest that the FDA-approved cholinergic agonist Carbachol may have therapeutic potential to improve fracture healing.

Methods

All procedures were performed on adult male wild type (C57BL/6) mice. We created unstable tibia fractures through three point bending and surgically resected nerves proximal to the fracture (either the sciatic nerve, femoral nerve, or both) and compared them to mice who received sham procedures. We injected Carbachol (Cch), a synthetic acetylcholine analogue, into the callus during the cartilaginous phase of healing and compared them to controls that were injected with Dulbecco's Modified Eagle's medium (DMEM) alone. Bone mineral density (BMD) and bone volume were quantified using micro-computed tomography (μCT) analysis. Following μCT the tibiae were processed for histology and stained using the Hall Brunt Quadruple stain (HBQ). The tissue composition was quantified using stereology on an Olympus Cast system.

FIGS. 21(A-C) illustrate changes to muscarinic receptor, neural cell marker, and nerve growth factor expression during endochondral fracture repair. qRT-PCR analysis of tibia fracture calli harvested 7, 10, and 14 days post-fracture reveals that nerve growth factor (NGF) is highly expressed at 7 days post-fracture, suggesting active neural recruitment to the fracture site at this time point (A). A significant increase in muscarinic receptor (B) and neural cell marker (C) expression by day 14 post-fracture suggests successful innervation of the fracture callus. N=2.

FIGS. 22(A-H) illustrate nerve resection leads to changes in osteogenic gene expression and fracture callus composition the femoral, sciatic, or both nerves were resected in adult C57BL/6 mice followed by tibia fracture. Controls were fractured and received a sham surgical procedure. (A) qRT-PCR analysis of fracture calli harvested 14 days post-fracture reveals significant down regulation of chondrogenic, osteogenic, and angiogenic genes (n=2). (B,C) Despite gene expression changes, stereological assessment of changes in bone and cartilage callus composition were not as high as expected, showing only a trend towards less bone. Interestingly, there was significantly less marrow space/vascularity in the callus, emphasizing the close relationship between innervation and vascularization. (D) Resecting the nerve leads to a signficant upregulationg of NGF. (E-H) HBQ histology of the fracture callus (outlined in green). Bone=red; Cartilage=blue.

FIGS. 23(A-F) illustrate lower bone mineral density and bone volume in sciatic and dual nerve resection groups assessed by uCT representative μCT images of tibia fractures (A-D) and μCT analysis for bone mineral density and bone composition (E,F). * indicates p<0.05.

FIGS. 24(A-B) illustrate plots showing the temporal therapeutic delivery of NGF to improve bone fracture healing in mice. (A) Timeline of experimental delivery of NGF to bone fracture site for two different post-fracture time ranges. (B) NGF expression decreases over time post-fracture.

FIG. 25 illustrates a plot showing a more delayed therapeutic delivery of NGF was more effective in activating bone healing. Compared to delayed NGF delivery at 4-6 days following fracture induction, delayed NGF delivery at 7-9 days post-fracture showed more robust activation of selected bone healing markers.

We found trends in both the μCT and stereology data indicating that resecting the sciatic nerve, either alone or in combination with a femoral nerve resection decreases BMD compared to sham procedures. Conversely, μCT data trends indicate that Cch-injected tibias have higher BMD than controls. These findings are significant because they implicate neuronal signaling in fracture healing and suggest that an acetylcholine analogue could have therapeutic potential in treating hypertrophic non-unions non-surgically.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:

1. A method of inducing bone formation, bone repair, and/or bone regeneration in a subject in need thereof, the method comprising:
   administering to chondrocytes of the subject a therapeutically effective amount of:
   (i) leukemia inhibitory factor (LIF) to induce transdifferentiation of the chondrocytes to osteoblasts; and optionally at least one of
   (ii) Wnt Surrogate (WntS); or
   (iii) carbachol, wherein the chondrocytes are in the subject at a site of bone fracture, bone disease, bone injury, or bone abnormality, and wherein the LIF, and optionally at least one of the WntS and carbachol is injected directly into the site of bone fracture, bone disease, bone injury, or bone abnormality.

2. The method of claim 1, administering to chondrocytes of the subject
   (i) LIF;
   (ii) WntS; and
   (iii) carbachol.

3. The method of claim 1, wherein the LIF induces a pluripotency like state that primes the chondrocytes for differentiation to osteoblasts.

4. The method of claim 1, wherein the WntS promotes differentiation of the chondrocytes to osteoblasts.

5. The method of claim 1, wherein the chondrocytes comprise hypertrophic chondrocytes.

6. The method of claim 5, wherein the LIF, the WntS, and/or carbachol is injected directly into soft cartilage callus at a bone fracture site.

7. The method of claim 5, wherein the bone injury comprises at least one of a delayed union fracture, nonunion fracture, hypertrophic nonunion, or growth plate disorder.

8. The method of claim 1, wherein the chondrocytes are provided in at least one of a cartilage graft or tissue engineered construct.

9. The method of claim 1, wherein LIF, the WntS, and/or carbachol is provided in a delivery vehicle that provides controlled release of LIF, WntS, and/or carbachol to the chondrocytes, the controlled release comprising at least one of a delayed, sustained, gradient, temporal, patterned, or spatial release.

10. A method of treating at least one of a delayed union bone fracture, nonunion bone fracture, or hypertrophic bone nonunion in a subject in need thereof, the method comprising:
    administering to soft cartilage callus at a site of the bone fracture or bone nonunion a therapeutically effective amount of:
    (i) leukemia inhibitory factor (LIF) to induce transdifferentiation of chondrocytes to osteoblasts; and at least one of
    (ii) Wnt Surrogate (WntS); or
    (iii) carbachol, wherein the LIF, and at least one of (WntS), and carbachol are injected directly into soft cartilage callus at the site.

11. The method of claim 10, administering to the subject:
    (i) LIF;
    (ii) WntS; and
    (iii) carbachol.

12. The method of claim 10, wherein LIF induces a pluripotency like state of the chondrocytes of the soft callus that primes the chondrocytes for differentiation to osteoblasts.

13. The method of claim 10, wherein the WntS promotes differentiation of chondrocytes to osteoblasts.

14. The method of claim 10, further comprising administering to the subject at least one of a cartilage graft or tissue engineered construct.

15. The method of claim 10 wherein LIF, WntS, and/or carbachol is provided in a delivery vehicle that provides controlled release of the LIF, the WntS, and/or carbachol to the soft cartilage callus the controlled release comprising at least one of a delayed, sustained, gradient, temporal, patterned, or spatial release.

* * * * *